(12) United States Patent
Li et al.

(10) Patent No.: US 12,390,460 B2
(45) Date of Patent: *Aug. 19, 2025

(54) TREATMENT FOR OBESITY

(71) Applicants: 1GLOBE BIOMEDICAL CO., LTD., Beijing (CN); 1GLOBE HEALTH INSTITUTE LLC, Norwood, MA (US)

(72) Inventors: Chiang J. Li, Cambridge, MA (US); Zoltan Derdak, Attleboro, MA (US); Darko Stevanovic, Jamaica Plain, MA (US); Jifeng Liu, Winchester, MA (US)

(73) Assignees: 1GLOBE BIOMEDICAL CO., LTD., Beijing (CN); 1GLOBE HEALTH INSTITUTE LLC, Norwood, MA (US)

( * ) Notice: Subject to any disclaimer, the term of this patent is extended or adjusted under 35 U.S.C. 154(b) by 1051 days.

This patent is subject to a terminal disclaimer.

(21) Appl. No.: 17/276,821

(22) PCT Filed: Sep. 18, 2019

(86) PCT No.: PCT/US2019/051788
§ 371 (c)(1),
(2) Date: Mar. 17, 2021

(87) PCT Pub. No.: WO2020/061231
PCT Pub. Date: Mar. 26, 2020

(65) Prior Publication Data
US 2021/0275523 A1  Sep. 9, 2021

Related U.S. Application Data

(60) Provisional application No. 62/732,650, filed on Sep. 18, 2018.

(51) Int. Cl.
*A61K 31/496* (2006.01)
*A61K 31/427* (2006.01)
(Continued)

(52) U.S. Cl.
CPC .......... *A61K 31/496* (2013.01); *A61K 31/427* (2013.01); *A61K 31/4439* (2013.01);
(Continued)

(58) Field of Classification Search
CPC ................ A61K 31/496; A61K 31/427; A61K 31/4439; A61K 45/06; A61P 3/04; A61P 3/10

See application file for complete search history.

(56) References Cited

U.S. PATENT DOCUMENTS 6,268,391 B1 * 7/2001 Dickerson ............ C07D 231/12
548/151
8,299,106 B2 * 10/2012 Li ........................ A61K 31/427
514/365

(Continued)

FOREIGN PATENT DOCUMENTS

WO  WO2008100977 A2  8/2008
WO  WO2008145398 A1  12/2008
(Continued)

OTHER PUBLICATIONS

Rana Malek & Stephen N. Davis (2016) Tyrosine kinase inhibitors under investigation for the treatment of type II diabetes, Expert Opinion on Investigational Drugs, 25:3, 287-296 (Year: 2016).*

(Continued)

*Primary Examiner* — Clinton A Brooks
*Assistant Examiner* — Izabela Schmidt
(74) *Attorney, Agent, or Firm* — Milstein Zhang & Wu LLC; Duan Wu, Esq.

(57) ABSTRACT

The invention provides novel methods of treating or preventing obesity or overweight and closely associated comorbidities therewith in a mammalian subject including human.

11 Claims, 16 Drawing Sheets

(51) Int. Cl.
  *A61K 31/4439* (2006.01)
  *A61K 45/06* (2006.01)
  *A61P 3/04* (2006.01)
  *A61P 3/10* (2006.01)
(52) U.S. Cl.
  CPC ............... *A61K 45/06* (2013.01); *A61P 3/04* (2018.01); *A61P 3/10* (2018.01)

(56) References Cited

U.S. PATENT DOCUMENTS

| | | |
|---|---|---|
| 9,795,595 B2 | 10/2017 | Li et al. |
| 2009/0202529 A1 | 8/2009 | Threadgill et al. |
| 2010/0285006 A1 | 11/2010 | Li et al. |
| 2014/0275033 A1 | 9/2014 | Li et al. |
| 2016/0311770 A1 | 10/2016 | Fett et al. |
| 2016/0368870 A1 | 12/2016 | Madanahalli Ranganath Rao et al. |
| 2018/0022743 A1 | 1/2018 | Li et al. |
| 2018/0230141 A1 | 8/2018 | Nonoyama et al. |
| 2019/0055235 A1 | 2/2019 | Brown et al. |

FOREIGN PATENT DOCUMENTS

| | | |
|---|---|---|
| WO | WO2015022437 A1 | 2/2015 |
| WO | WO2016176420 A1 | 11/2016 |
| WO | WO2018005444 A2 | 4/2018 |

OTHER PUBLICATIONS

Fei Gao, Zhi Jian Wang, Hua Shen, Shi Wei Yang, Bin Nie, Yu Jie Zhou; J Diabetes Investig 2018; 9: 44-54 (Year: 2018).*
Flegal KM, Kit BK, Orpana H, Graubard BI. Association of all-cause mortality with overweight and obesity using standard body mass index categories: a systematic review and meta-analysis. JAMA. Jan. 2, 2013;309(1):71-82 (Year: 2013).*
Klatsky AL, Zhang J, Udaltsova N, Li Y, Tran HN. Body Mass Index and Mortality in a Very Large Cohort: Is It Really Healthier to Be Overweight? Perm J. 2017;21:16-142. doi: 10.7812/TPP/16-142. (Year: 2017).*
Fountas A, Diamantopoulos LN, Tsatsoulis A. Tyrosine Kinase Inhibitors and Diabetes: A Novel Treatment Paradigm? Trends Endocrinol Metab. Nov. 2015;26(11):643-656. doi: 10.1016/j.tem.2015.09.003. Epub Oct. 19, 2015. Erratum in: Trends Endocrinol Metab. Jan. 2016;27(1):65. (Year: 2015).*
M.P. Coghlan, D.M. Smith; Introduction to the Kinases in Diabetes Biochemical Society focused meeting: are protein kinases good targets for antidiabetic drugs?. Biochem Soc Trans Apr. 1, 2005; 33 (2): 339-342. (Year: 2005).*
Keiko Ono, et al., Rapid Amelioration of Hyperglycemia Facilitated by Dasatinib in a Chronic Myeloid Leukemia Patient with type 2 Diabetes Mellitus, Internal Medicine, 2012, vol. 51, I (Year: 2012).*
Stella et al; Prodrugs: Challenges and Rewards, Part 1, 2007 (Year: 2007).*
Dharmalingam M, Yamasandhi PG. Nonalcoholic Fatty Liver Disease and Type 2 Diabetes Mellitus. Indian J Endocrinol Metab. May-Jun. 2018;22(3):421-428 (Year: 2018).*
ISA(US), International Search Report and Written Opinion for PCT/US19/51788, Feb. 20, 2020, USA.
Winder W.et al., "Can patients with type 2 diabetes be treated with 5'-AMP-activated protein kinase activators?" Diabetologia. (2008) 51:10, 1761-1764.
Cameron, K. et al., "Discovery and Preclinical Characterization of 6-Chloro-5-[4-(1-hydroxycyclobutyl)phenyl]-1H-indole-3-carboxylic Acid . . . " J. Med. Chem. 2016, 59, 8068-8081.
IP Australia, Examination report No. 1 in equivalent Australian Application No. 2019343922, mailed Jan. 6, 2023.
Chinese Patent Office, Search Report in equivalent Chinese applictaion No. 201980061265.3, mailed 124 Jan. 2022.
EPO, European search report in equivalent European Application 19862078.3, mailed May 17, 2022.
Japanese Patent Office, first Office action in equivalent JP application 2021-539500, mailed Sep. 19, 2023.
New Zealand IP Office, first Office action in equivalent NZ Application 774374, mailed Feb. 1, 2024.
Rospatent, office action in equivalent Russian Patent Application No. 202110715904, mailed Oct. 10, 2023.
IP Office of Singapore, first Written Opinion in equivalent Singaporian applictaion No. 11202102683X, Sep. 5, 2022.
IP Office of Singapore, second Written Opinion in equivalent Singaporian applictaion No. 11202102683X, Jul. 15, 2024.
Taiwan IP Bureau, first Examiner report in equivalent Taiwan Patent application No. 108133699, Jun. 5, 2023.

* cited by examiner

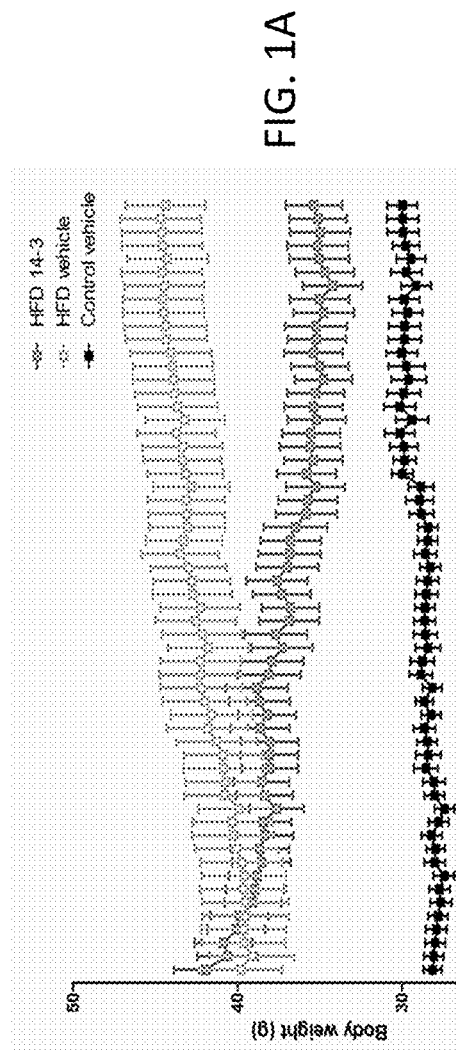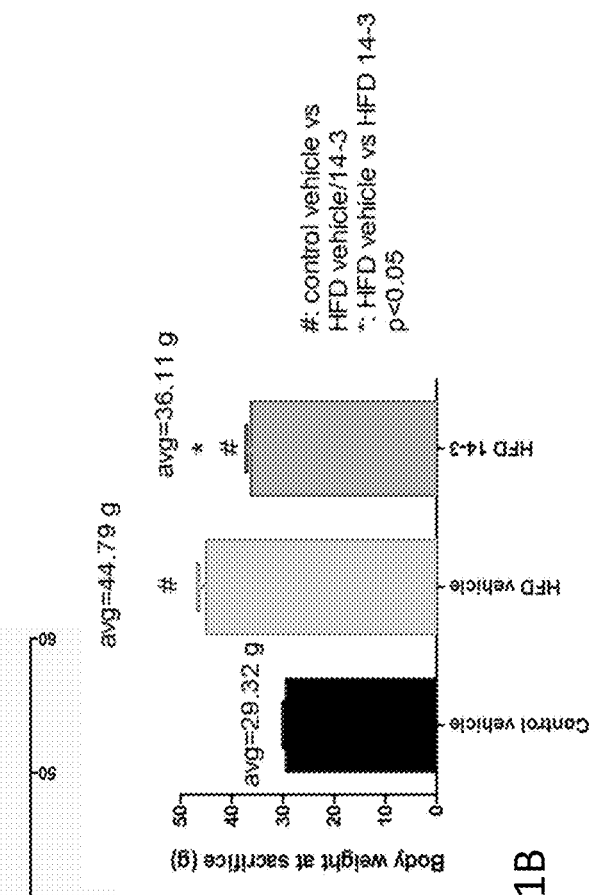

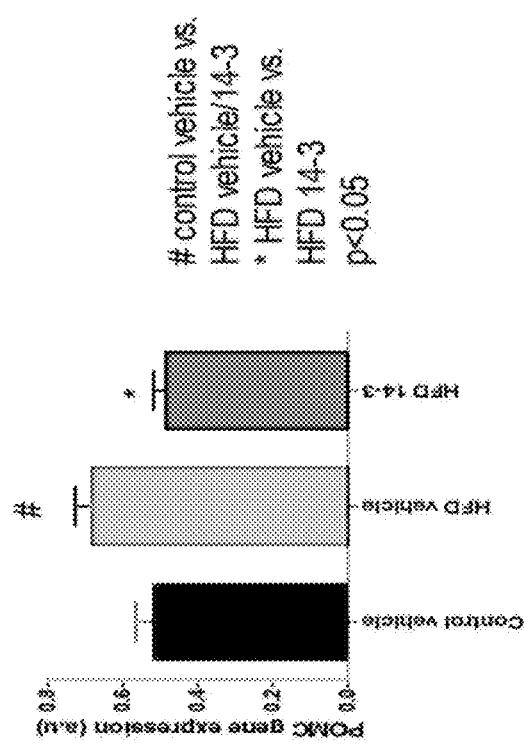
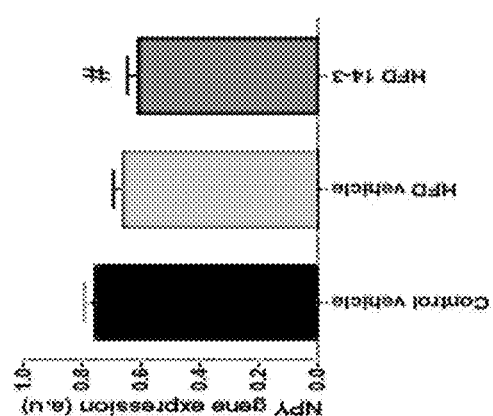
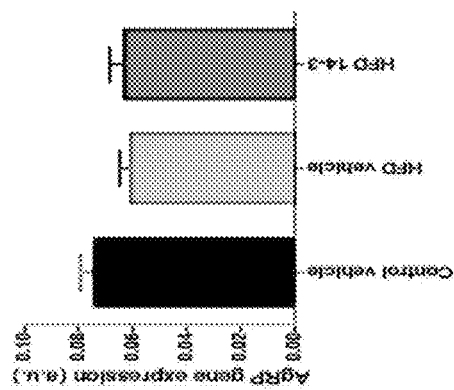
FIG. 2B

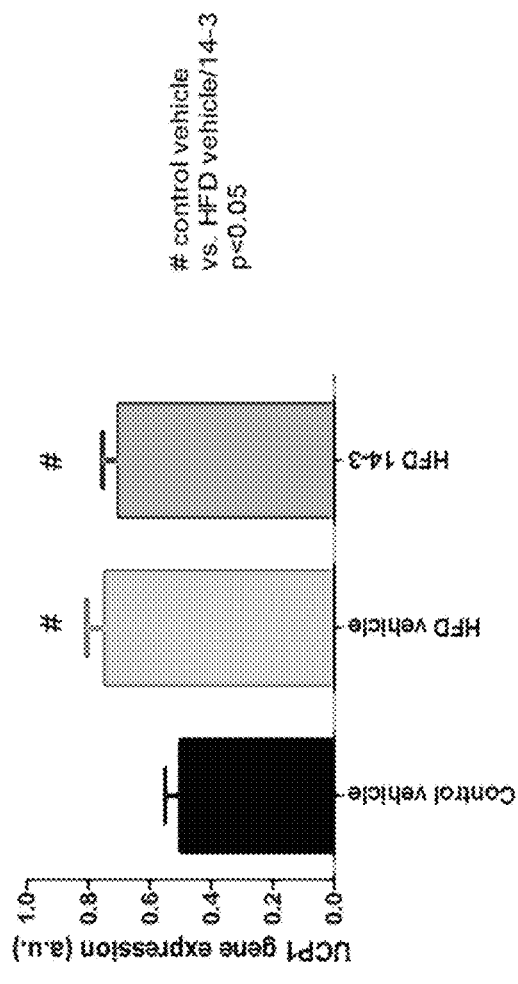
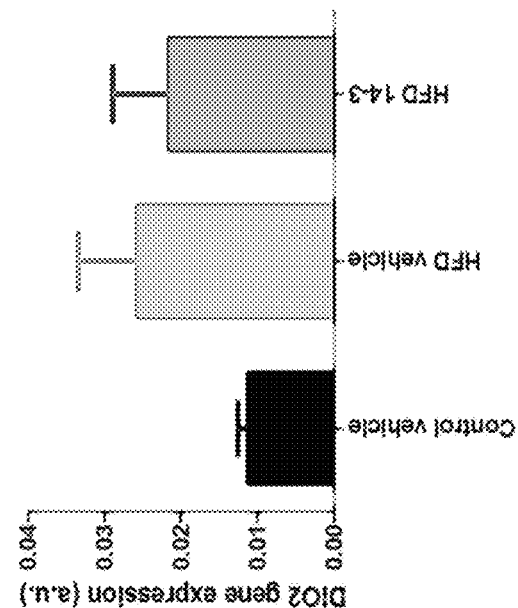
FIG. 2C

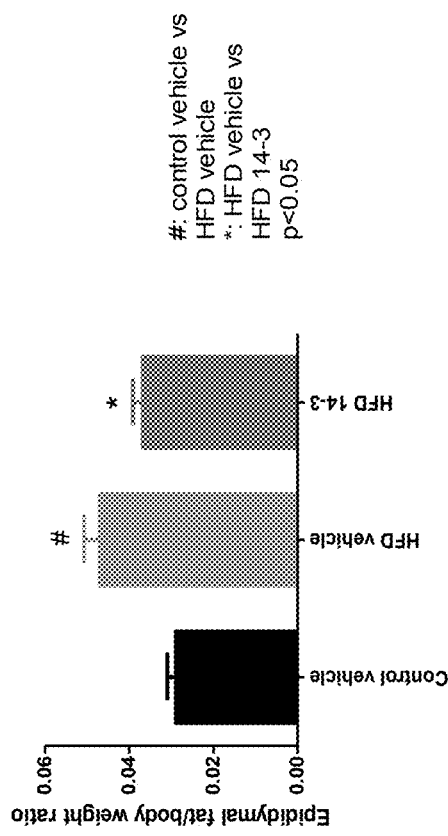
FIG. 3A
FIG. 3B
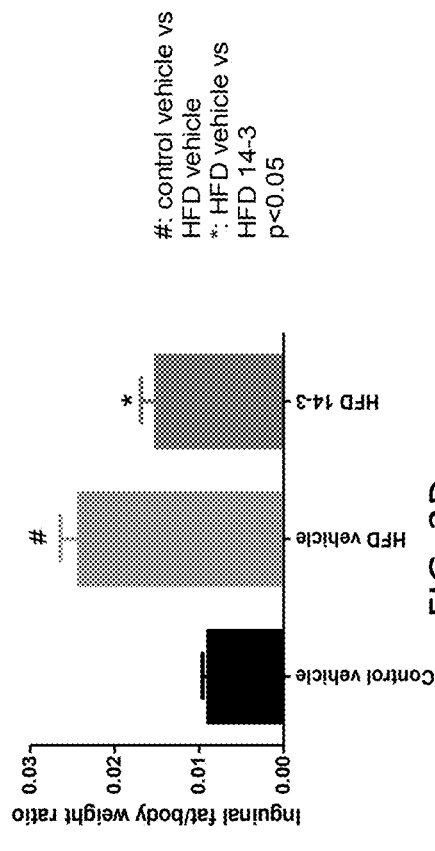
FIG. 3C
FIG. 3D
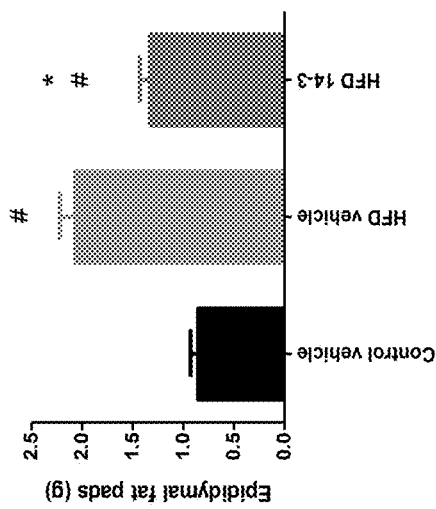
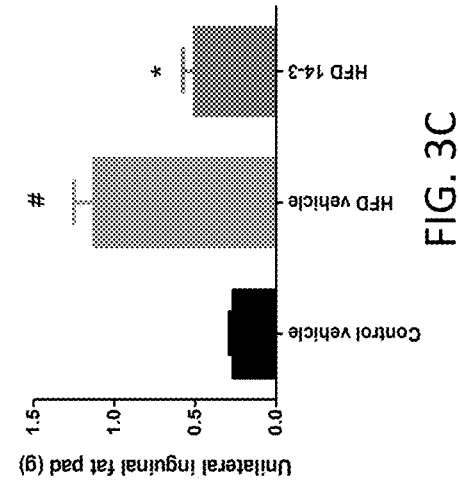

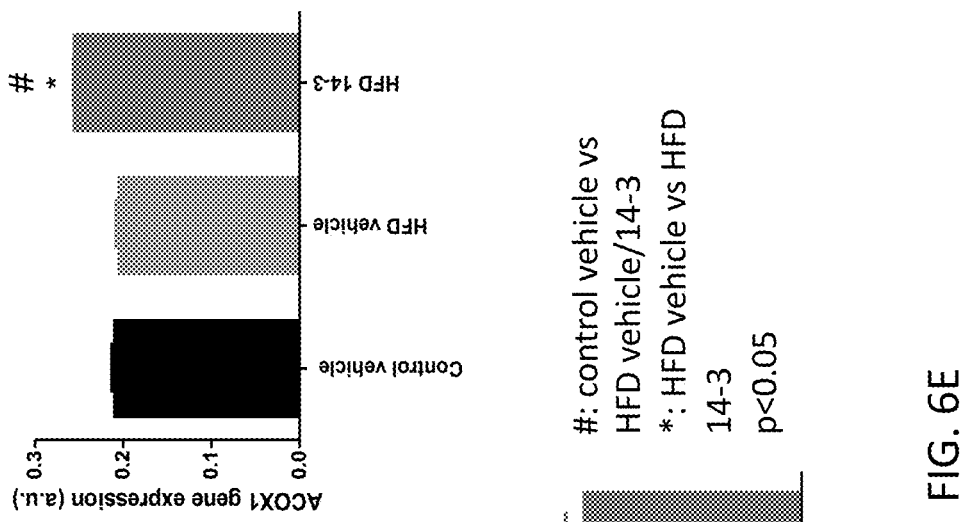
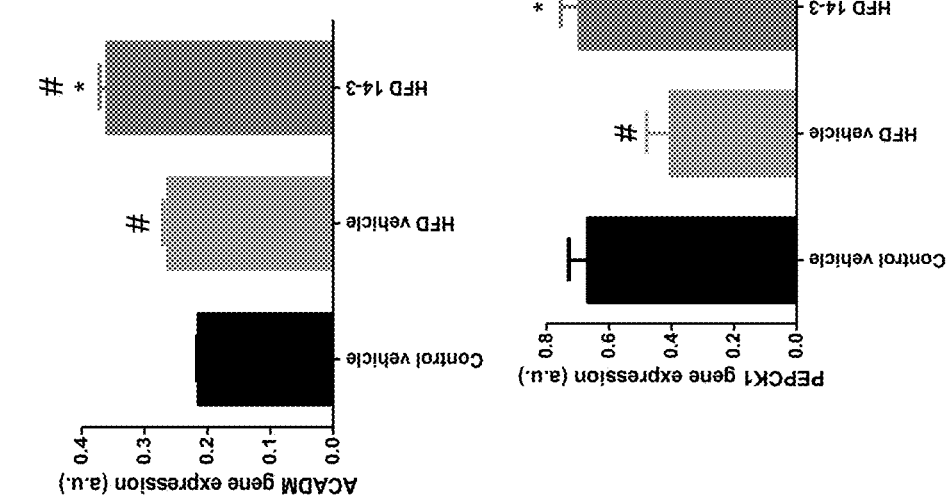
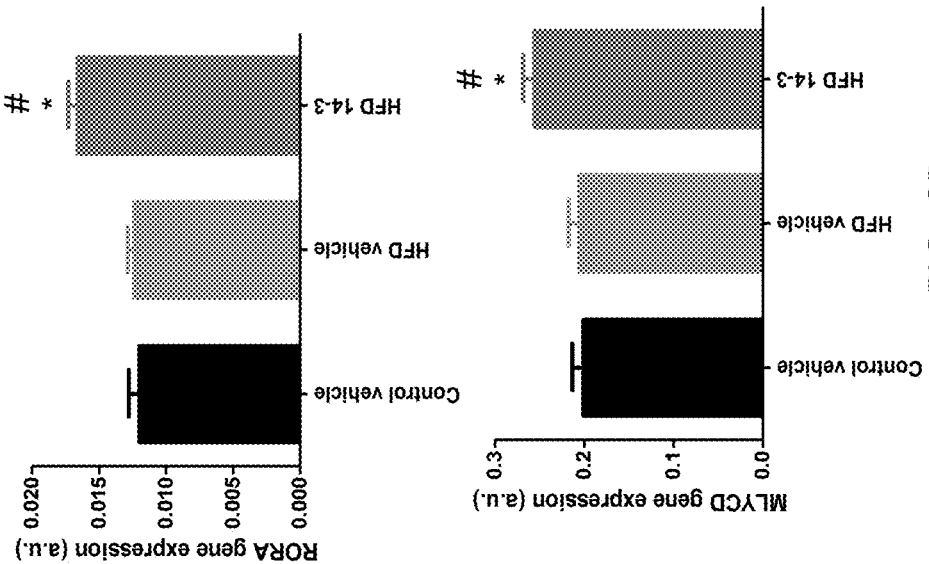
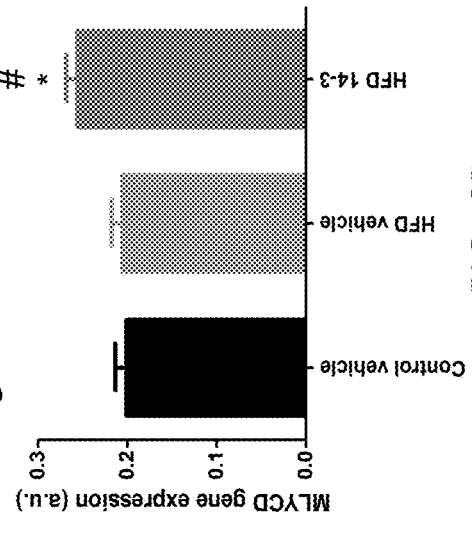

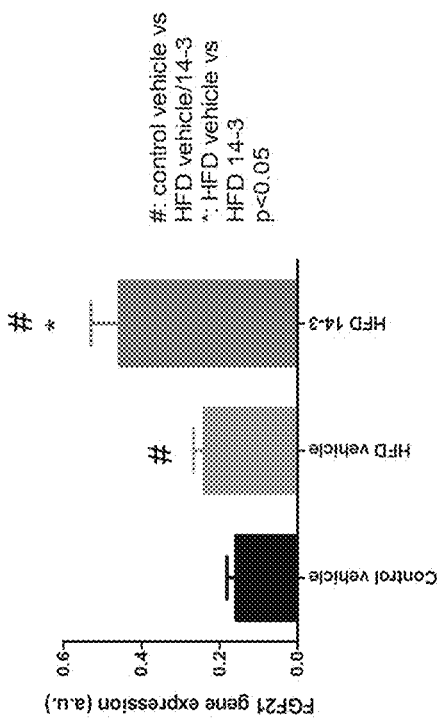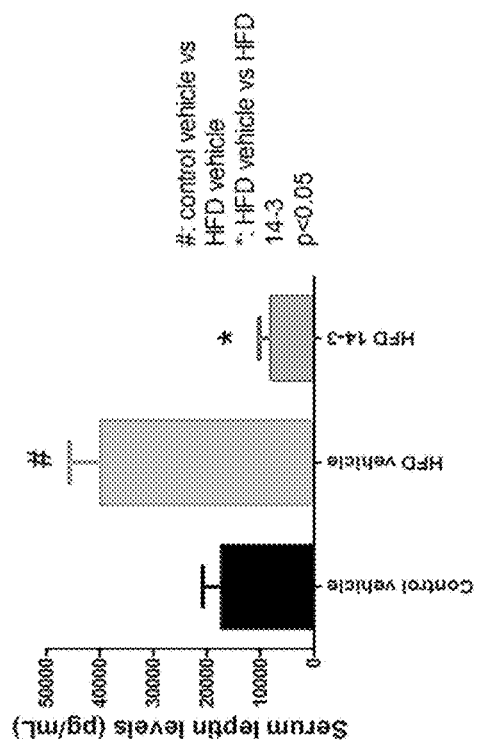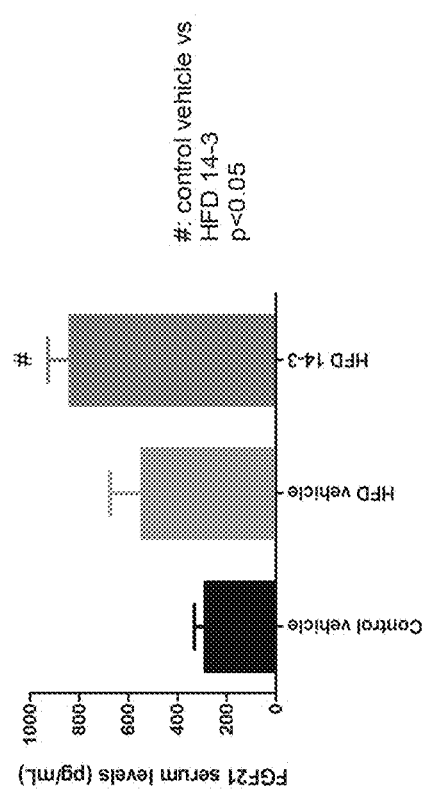
FIG. 7A
FIG. 7B
FIG. 7C

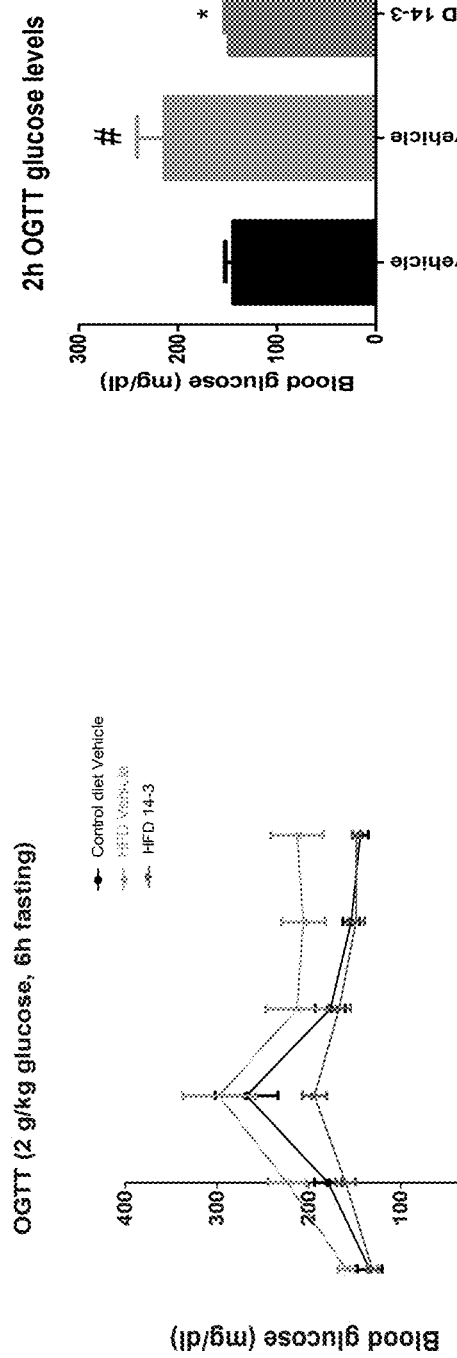
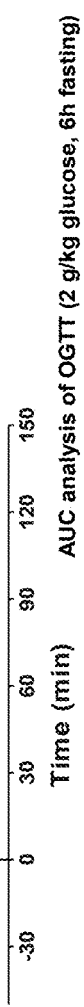
FIG. 9A
FIG. 9B
FIG. 9C

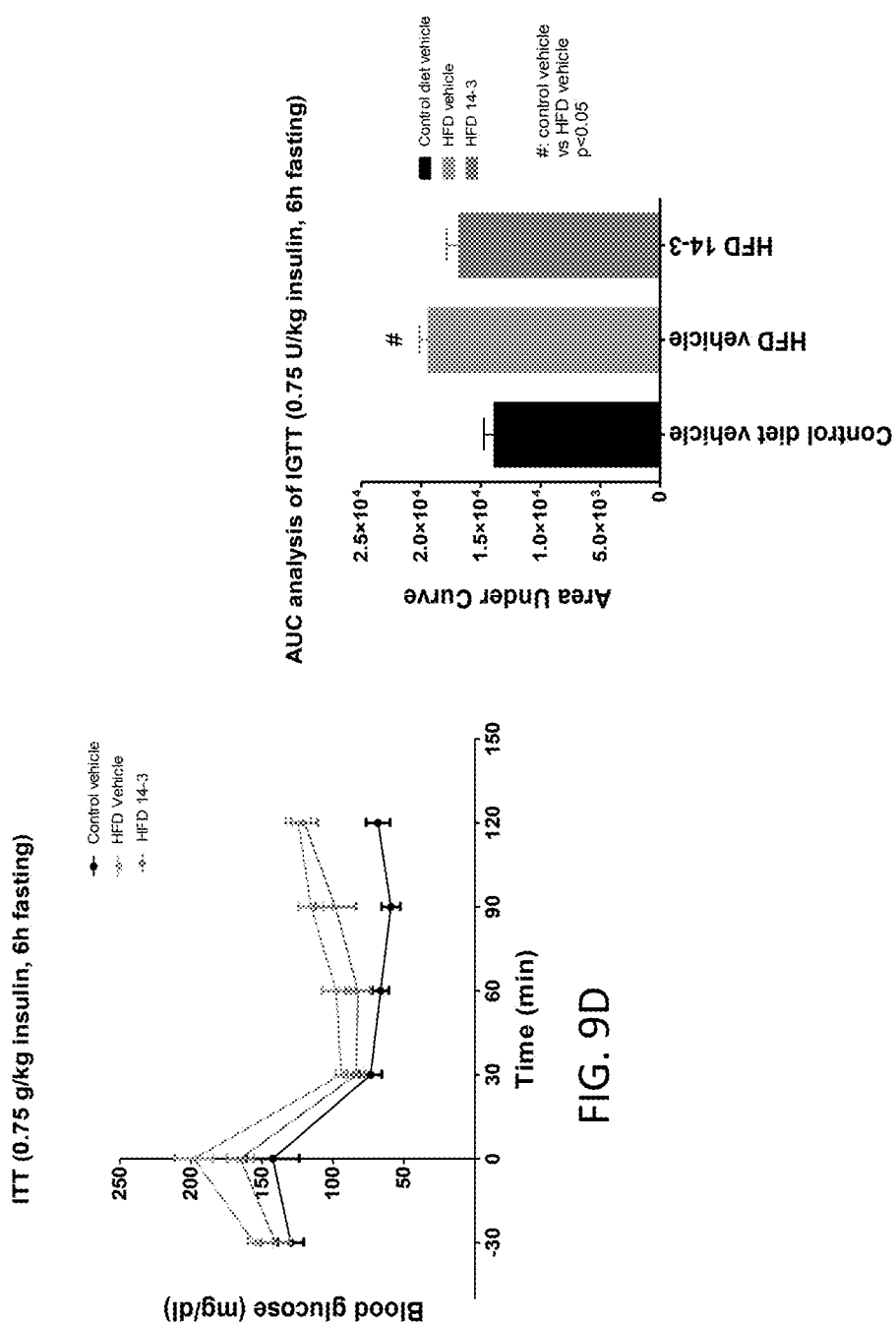

TREATMENT FOR OBESITY

CROSS-REFERENCE TO RELATED APPLICATIONS

This application is a national phase application under 35 U.S.C. 371 of international application PCT/US19/51788, filed Sep. 18, 2019 which claims priority to and the benefit of U.S. provisional patent application Ser. No. 62/732,650, filed Sep. 18, 2018, which application is incorporated herein by reference in its entirety.

TECHNICAL FIELD

The invention generally relates to methods of treating obesity and obesity-related conditions and disorders in a subject and related compositions thereof.

BACKGROUND OF INVENTION

Worldwide, obesity has become a major threat to public health, and as a result, it has brought enormous financial burden to many families and countries. It is estimated that there are about 600 million obese adults worldwide with Body Mass Index (BMI)≥30 $kg/m^2$. Childhood obesity is particularly concerning, as this is often an ignored condition that can lead to long-term health issues. In U.S. alone, adult obesity rates have increased substantially in the last several decades.

Obesity is a well-established risk factor of associated diseases, including type II diabetes mellitus, cardiovascular diseases, non-alcoholic fatty liver disease (NAFLD), the metabolic syndrome, polycystic ovary syndrome (PCOS), obstructive sleep apnea, osteoarthritis, and several forms of cancer (endometrial, esophageal, gastric, liver, kidney, multiple myeloma, meningioma, colorectal, gallbladder, breast, etc.). In societies where stereotypical views of obesity are prevalent, overweight people also face a myriad of psychological and social challenges, and often suffer from low self-esteem, prejudice and discrimination.

A clinically significant weight loss (>5%) can: reduce risk factors for cardiovascular diseases (CVD), delay or prevent the development of various cancers and type II diabetes, and ultimately improve quality of life. However, most patients fail to achieve sustained and clinically significant weight loss with current therapies.

Currently, bariatric surgery represents the most effective treatment for obesity, although it has substantial limitations, which include the irreversibility of the procedure, perioperative risks including bleeding, anastomotic leakage, infection, internal herniation, nutritional deficiencies, postprandial hypoglycemia, death, and high financial cost.

There are continued unmet needs for effective treatment and/or prophylaxis for obesity and closely related conditions/disorders.

SUMMARY OF THE INVENTION

The present invention addresses these needs. The invention provides for novel method of using a compound of the invention (embodiments described in detail below). In one aspect, the invention provides methods for treating or preventing obesity or overweight in a mammal including a human, comprising administering to a mammalian subject in need thereof: a therapeutically effective amount of a pharmaceutical composition comprising the compound of the invention, or an enantiomer, diastereomer, tautomer, or pharmaceutically acceptable salt, solvate, ester or pro-drug thereof that is effective in the treatment or prevention of obesity or overweight thereof in a mammal including a human, and a pharmaceutically acceptable excipient, carrier, or diluent.

In another aspect, the invention provides methods for treating or preventing type II diabetes mellitus in a mammal including a human, comprising administering to a mammalian subject in need thereof: a therapeutically effective amount of a pharmaceutical composition comprising the compound of the invention, or an enantiomer, diastereomer, tautomer, or pharmaceutically acceptable salt, solvate, ester or pro-drug thereof that is effective in the treatment or prevention of type II diabetes mellitus thereof in a mammal including a human, and a pharmaceutically acceptable excipient, carrier, or diluent.

In another aspect, the invention provides methods for treating or preventing the metabolic syndrome in a mammal including a human, comprising administering to a mammalian subject in need thereof: a therapeutically effective amount of a pharmaceutical composition comprising the compound of the invention, or an enantiomer, diastereomer, tautomer, or pharmaceutically acceptable salt, solvate, ester or pro-drug thereof that is effective in the treatment or prevention of the metabolic syndrome thereof in a mammal including a human, and a pharmaceutically acceptable excipient, carrier, or diluent.

In one aspect, the invention provides a method for reducing, ameliorating, or eliminating morbidity or mortality including at least a symptom or indication known to be associated with obesity or overweight, such as excessive weight, excessive fat, an elevated BMI≥30 $kg/m^2$ or 25 $kg/m^2$.

In one aspect, the invention provides a method for reducing, ameliorating, or eliminating morbidity or mortality at least a symptom or indication known to be associated with type II diabetes mellitus, such as insulin resistance, frequent urination, increased thirst, and increased hunger.

In one aspect, the invention provides a method for reducing, ameliorating, or eliminating morbidity or mortality at least a symptom or indication known to be associated with the metabolic syndrome such as elevated blood pressure, elevated fasting plasma glucose, high serum triglycerides, low high-density lipoprotein (HDL) levels, and elevated waist circumference.

In one feature, the methods of the invention further include an additional step of administering an additional agent selected from the group consisting of: an insulin-sensitizing medication, a diabetes medication, a medication or therapeutic for the metabolic syndromes, and a weight-loss medication as part of a combinatorial regimen.

In various embodiments, the compound of the invention is one of Formulas I-X as described below in the detailed description of the invention.

In various embodiments, the compound of the invention is one of the following eight compounds as described in more detail hereinafter: compound 9, compound 15-3, compound 12, compound 10-1, compound 15-1, compound 14-3, compound 5 and compound 7-1.

In further embodiments, the compound of the invention is one of the following fifteen compounds as described in more detail hereinafter: compound 13-3-1, compound 13-3-2, compound 13-3-3, compound 13-3-5, compound 13-3-6, compound 13-3-7, compound 13-3-10, compound 13-3-11, compound 001, compound 004, compound 006, compound 013, compound 132, compound 133, and compound 134.

In yet another aspect, the invention generally relates to a pharmaceutical composition comprising a compound disclosed herein, or a pharmaceutically acceptable salt, solvate, ester or pro-drug thereof, and a pharmaceutically acceptable excipient, carrier, or diluent, as well as uses thereof.

In a feature, the invention generally relates to a method of reducing weight or preventing weight gain for a patient in need thereof using one or more compositions disclosed herein. Treatment may further comprise the additional step of evaluating the success of the treatment by evaluating the subject/patient before and during treatment.

BRIEF DESCRIPTION OF THE DRAWINGS

FIGS. 1A-1D present in vivo animal data on: (1A) change in body weight during Compound 14-3 treatment; (1B) body weight at the time of euthanasia; (1C) daily normalized caloric intake during Compound 14-3 treatment; and (1D) daily normalized water intake during Compound 14-3 treatment.

FIGS. 2A-2C present in vivo animal data on: (2A) fecal triglyceride content; (2B) gene expression levels of molecular mediators of appetite regulation; and (2C) gene expression levels of markers for brown adipose tissue activation.

FIGS. 3A-3D present in vivo animal data on: (3A) epididymal fat pad weights; (3B) epididymal fat/body weight ratio; (3C) unilateral inguinal fat pad weight; and (3D) Inguinal fat/body weight ratio.

FIGS. 6A-6E present in vivo animal data on the gene expression of: (6A) RAR-related orphan receptor alpha (RORA); (6B) Acyl-Coenzyme A dehydrogenase, C-4 to C-12 straight chain (ACADM); (6C) Peroxisomal acyl-coenzyme A oxidase 1 (ACOX1); (6D) Malonyl CoA decarboxylase (MLYCD); and (6E) Phosphoenolpyruvate carboxykinase (PEPCK).

FIGS. 7A-7C present in vivo animal data on: (7A) serum FGF21 levels; (7B) gene expression of FGF21; and (7C) serum leptin levels.

FIGS. 9A-9E present in vivo animal data on: (9A) blood glucose levels during oral glucose tolerance test (OGTT); (9B) area under curve during OGTT; (9C) blood glucose levels at 120 min during OGTT; (9D) blood glucose levels during intraperitoneal insulin tolerance test (ITT); and (9E) area under curve during ITT.

FIGS. 10A-10C show quantification data on accumulation of intracellular triglyceride when various embodiments of the compound of the invention are each used in a given sample: Compound 14-3 (*: DMSO vs Compound 14-3 in corresponding culture media; #: control medium (left two columns) vs. palmitoleic acid (POA) medium (right two columns); p<0.05) (FIG. 10A); effects from nine other embodiments in POA medium compared to that of Compound 14-3 (FIG. 10B); effects from seven different embodiments in POA medium compared to that of Compound 14-3 (FIG. 10C).

DEFINITIONS

Figures 1C, 1D:
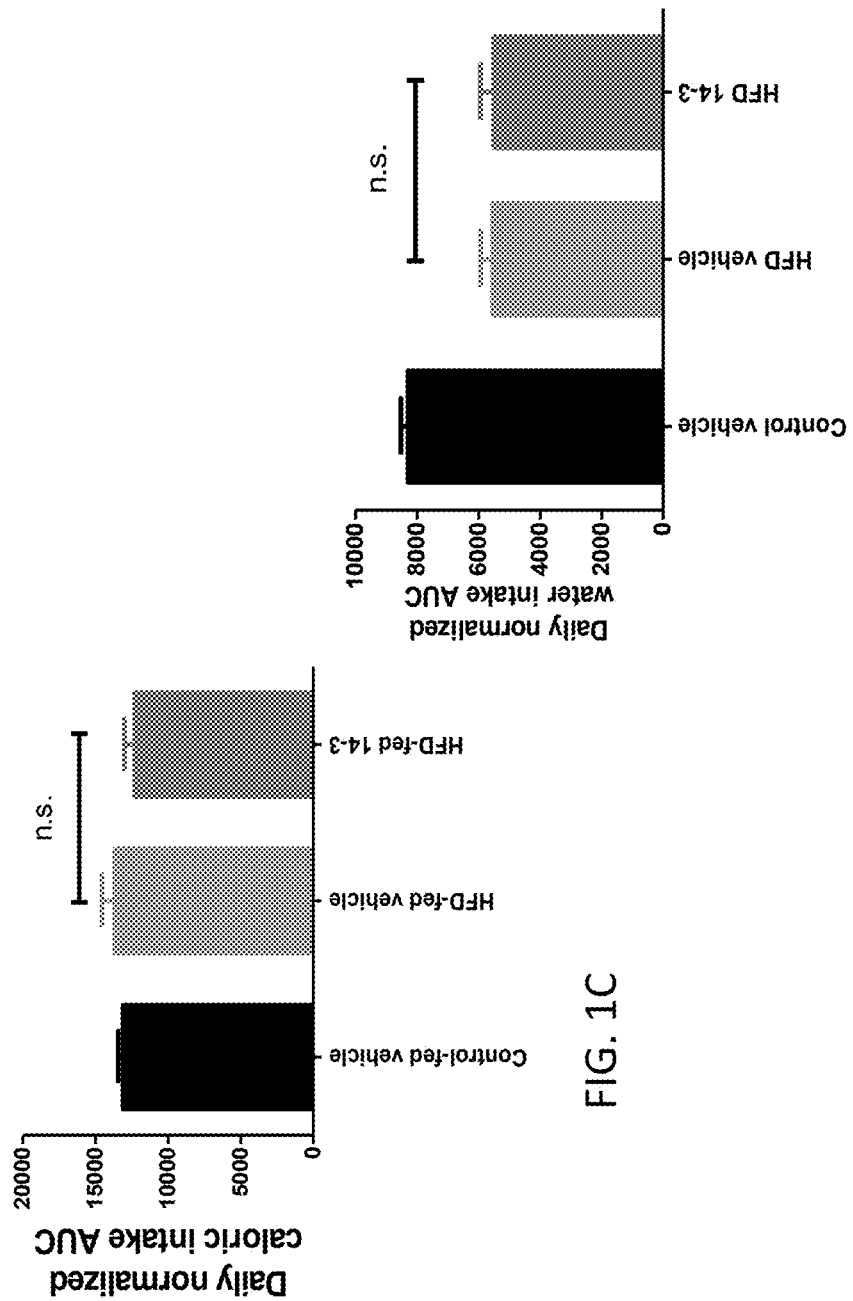

As used in the specification and claims, the singular form "a", "an", or "the" includes plural references unless the context clearly dictates otherwise. For example, the term "a cell" includes a plurality of cells including mixtures thereof.

As used herein, the term "about" or "approximately" when used in conjunction with a number refers to any number within 5, 10 or 15% of the referenced number.

As used herein, the term "subject" refers to any animal (e.g., a mammal), including, but not limited to humans, non-human primates, rodents, canines, and the like, which is to be the recipient of a particular treatment. Typically, the terms "subject" and "patient" are used interchangeably herein in reference to a human subject.

As used herein, the term "obesity" refers to a medical condition where body fat has accumulated such that it will likely or has already negatively affected the subject's health. One commonly used threshold for obesity is a body mass index (BMI), calculated by dividing a person's weight by the square of that person's height, that is no less than 30 kg/m$^2$, except in the Asia-Oceania Region and WHO Western Pacific Region, a value no less than 25 kg/m$^2$ may be used (Kanazawa et al., World Review of Nutrition and Dietetics. 94: 1-12 (2005)). In areas outside the Asia-Oceania Region and WHO Western Pacific Region, a BMI in the range of 25-30 kg/m$^2$ is considered "overweight."

As used herein, the term "metabolic syndrome" or "insulin resistance syndrome" refers to having at least three of the five following medical conditions: abdominal (central) obesity, elevated blood pressure, elevated fasting plasma glucose, high serum triglycerides, and low high-density lipoprotein (HDL) levels. While the exact causes of the syndrome are still being researched, the following risk factors are considered as likely contributing to the onset of the syndrome: high-sugar or high-caloric diet, obesity, insulin resistance, sedentary lifestyle, stress, and aging. Various diagnostic criteria have been proposed by different organizations where the main difference appears to be the measure for central obesity. In an attempt to unify the diagnostic criteria, several major organizations agreed that three abnormal findings out of five measurements should result in a clinical diagnosis of the metabolic syndrome, while waist measurement would continue to be a useful preliminary screening tool but not obligatory (Alberti et al. *Circulation* 2009 Oct. 20; 120(16):1640-1645). An exemplary set of diagnostic cut points are: for elevated waist circumference: population- and country-specific definitions; for elevated triglycerides (or drug treatment therefor): ≥150 mg/dL (1.7 mmol/L); for reduced high-density lipoprotein cholesterol (HDL-C) (or drug treatment therefor): <40 mg/dL (1.0 mmol/L) in males; <50 mg/dL (1.3 mmol/L) in females; for elevated blood pressure triglycerides (or drug treatment therefor): systolic BP≥130 and/or diastolic BP≥85 mm Hg.; for elevated fasting glucose triglycerides (or drug treatment therefor): <100 mg/dL.

As used herein, the terms "treat", "treating", and "treatment" have their ordinary and customary meanings, and include one or more of: blocking, ameliorating, or decreasing in severity, frequency and/or progression of a symptom of a disease or condition (e.g., diabetes) or inducing regression or stasis of the disorder or disease in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 95%, 90%, 80%, 70%, 60%, 50%, 40%, 30%, 20%, 10%, or 5% versus a subject in which the methods of the present invention have not been practiced. Treatment can be for an existing condition or prophylactically for future conditions.

As used herein, the terms "inhibiting", "to inhibit" and their grammatical equivalents, when used in the context of a bioactivity, refer to a down-regulation of the bioactivity, which may reduce or eliminate the targeted function, such as the production of a protein or the phosphorylation of a molecule. In particular embodiments, inhibition may refer to a reduction of about 20%, 30%, 40%, 50%, 60%, 70%, 80%, 90% or 95% of the targeted activity. When used in the context of a disorder or disease, the terms refer to success at preventing or significantly delaying the onset of symptoms, alleviating symptoms, or eliminating the disease, condition or disorder.

As used herein the terms "administration," "administering," or the like, when used in the context of providing a pharmaceutical composition to a subject generally refers to providing to the subject one or more pharmaceutical compositions comprising the compound of the invention in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intraperitoneal, transdermal, or buccal routes of delivery.

Definitions of specific functional groups and chemical terms are described in more detail below. General principles of organic chemistry, as well as specific functional moieties and reactivity, are described in "*Organic Chemistry*", by Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in "*Protective Groups in Organic Synthesis*," Third Ed. Greene, T. W. and Wuts, P. G., Eds., John Wiley & Sons, New York: 1999.

It will be appreciated that the compounds, as described herein, may be substituted with any number of substituents or functional moieties. Throughout the specifications, groups and substituents thereof may be chosen to provide stable moieties and compounds.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the term "pharmaceutically acceptable salt" refers to either a pharmaceutical acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

The compounds of the present invention may form salts that are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps that may be employed during preparation. Salts of the compounds of the present invention may be formed, for example, by reacting a compound I, II or III with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention that contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable ester," refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

As used herein, the term "prodrug" refers to a pharmacological derivative of a parent drug molecule that requires biotransformation, either spontaneous or enzymatic, within the organism to release the active drug. For example, prodrugs are variations or derivatives of the compounds of Formula I that have groups cleavable under certain metabolic conditions, which when cleaved, become the compounds of Formula I. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form.

Prodrug forms often offer advantages of solubility, tissue compatibility, or delayed release in the mammalian organism (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substituents disclosed herein.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, "$C_x$-$C_y$" refers in general to groups that have from x to y (inclusive) carbon atoms. Therefore, for example, "$C_1$-$C_6$" refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. "$C_1$-$C_{20}$" and the likes similarly encompass the various combinations between 1 and 20 (inclusive) carbon atoms, such as $C_1$-$C_6$, $C_1$-$C_{12}$ and $C_3$-$C_{12}$.

As used herein, the terms "alkyl" refers to a straight or branched chain alkane (hydrocarbon) radical. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. "Substituted alkyl" refers to an alkyl group substituted with one or more substituents, preferably 1 to 4 substituents, at any available point of attachment. Exemplary substituents include, but are not limited to, one or more of the following groups: hydrogen, halogen (e.g., a single halogen substituent or multiple halo substituents forming, in the latter case, groups such as $CF_3$ or an alkyl group bearing $Cl_3$), cyano, nitro, $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle or substituted heterocycle; and $R_e$ is alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle and aryl can themselves be optionally substituted. As used herein, the term "$C_x$-$C_y$ alkyl" refers to a saturated linear or branched free radical consisting essentially of x to y carbon atoms, wherein x is an integer from 1 to about 10 and y is an integer from about 2 to about 20. Exemplary $C_x$-$C_y$ alkyl groups include "$C_1$-$C_{20}$ alkyl," which refers to a saturated linear or branched free radical consisting essentially of 1 to 20 carbon atoms and a corresponding number of hydrogen atoms. Exemplary $C_1$-$C_{20}$ alkyl groups include methyl, ethyl, n-propyl, isopropyl, n-butyl, isobutyl, dodecanyl, etc. Of course, other $C_1$-$C_{20}$ alkyl groups will be readily apparent to those of skill in the art given the benefit of the present disclosure. The term "alkyl" is $C_1$-$C_{20}$, preferably $C_1$-$C_{10}$, more preferably $C_1$-$C_6$, further preferably $C_1$-$C_6$.

As used herein, the term "alkenyl" refers to a straight or branched chain hydrocarbon radical having at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substituents can themselves be optionally substituted. The term "alkenyl" is $C_2$-$C_{20}$, preferably $C_2$-$C_{10}$, more preferably $C_2$-$C_6$.

As used herein, the term "alkynyl" refers to a straight or branched chain hydrocarbon radical having at least one carbon-to-carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substituents can themselves be optionally substituted. The term "alkynyl" is $C_2$-$C_{20}$, preferably $C_2$-$C_{10}$, more preferably $C_2$-$C_6$.

As used herein, the term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" or "Substituted phenyl" refers to an aryl or a phenyl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. The exemplary substituents can themselves be optionally substituted. Exemplary substituents also include fused cyclic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

As used herein, the term "cycloalkyl" refers to a fully saturated cyclic hydrocarbon group having from 1 to 4 rings and 3 to 10 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted. The term "cycloalkyl" is $C_3$-$C_{10}$, preferably $C_3$-$C_8$, more preferably $C_3$-$C_6$.

As used herein, the term "cycloalkenyl" refers to a partially unsaturated cyclic hydrocarbon group containing 1 to 4 rings and 3 to 10 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted. The term "cycloalkenyl" is $C_3$-$C_{10}$, preferably $C_3$-$C_8$, more preferably $C_3$-$C_6$.

As used herein, the terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) that have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

As used herein, "substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, heterocyclic or substituted heterocyclic, aryl or substituted aryl, as well as those groups recited above as exemplary alkyl substituents. The exemplary substituents can themselves be optionally substituted. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

As used herein, the term "halogen" refers to fluorine (F), chlorine (Cl), bromine (Br), or iodine (I).

The term "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, preferably 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents. The exemplary substituents can themselves be optionally substituted.

Unless otherwise indicated, any heteroatom with unsatisfied valences is assumed to have hydrogen atoms sufficient to satisfy the valences.

Isotopically labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^1H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. See, WO 2007/005643, WO 2007/005644, WO 2007/016361, and WO 2007/016431.

The term "hydrogen" refers to all hydrogen isotopes including protium and deuterium. In a given composition, the hydrogen molecules can be all protium, all deuterium, or a mixture of both, unless specified otherwise.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

The compounds, salts, esters, prodrugs, hydrates, and solvates presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Atropisomers are also within the scope of the present disclosure. Atropisomers refer to compounds that can be separated into rotationally restricted isomers.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates of the compounds of the invention are also contemplated herein. Solvates of the compounds of the present invention include, for example, hydrates.

DETAILED DESCRIPTION OF THE INVENTION

The invention provides compounds as well as pharmaceutical compositions containing such compounds described herein, or an enantiomer, diastereomer, tautomer, or pharmaceutically acceptable salt, solvate, ester or pro-drug thereof, and uses thereof in the treatment and prevention of obesity or overweight and diseases and disorders closely associated therewith, e.g., type II diabetes and the metabolic syndrome, in a mammalian subject.

Specifically, the present invention provides a pharmaceutical composition comprising any compound of the invention described herein, or a pharmaceutically acceptable salt, solvate, ester or pro-drug thereof, and a pharmaceutically acceptable excipient, carrier, or diluent.

The invention also provides method for treating or preventing obesity or overweight, and diseases and disorders closely associated therewith, e.g., type II diabetes and the metabolic syndrome, in a mammalian subject including a human, comprising administering to a mammalian subject in need thereof: a therapeutically effective amount of a pharmaceutical composition comprising any of the compound of the invention described herein, or an enantiomer, diastereomer, tautomer, or pharmaceutically acceptable salt, solvate, ester or pro-drug thereof that is effective in the treatment or prevention of obesity or overweight, and diseases and disorders closely associated therewith, e.g., type II diabetes and the metabolic syndrome, in a mammal including a human, and a pharmaceutically acceptable excipient, carrier, or diluent.

In one feature, the invention provides a method that produces one or more of the following health benefits from successfully treating or preventing obesity or overweight and possibly their comorbidities: a decrease in body weight and BMI; an improvement in insulin sensitivity; an improvement in liver function; and an improvement in at least one of the five diagnostic criteria for the metabolic syndrome.

In some embodiments, the invention generally relates to the use of a compound of Formula I,

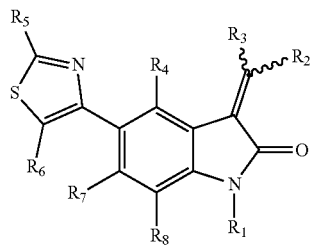

(I)

or an enantiomer, diastereomer, tautomer, or pharmaceutically acceptable salt or solvate thereof, for treating, therapeutically or prophylactically, obesity or overweight, and comorbidities closely associated therewith, including type II diabetes and the metabolic syndrome, wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_d$, or $C(=O)NR_bR_c$;

$R_2$ is heterocycle or substituted heterocycle, aryl or substituted aryl;

$R_3$ is hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl, amino or substituted amino;

$R_6$ is hydrogen, halogen, cyano, nitro, $CF_3$, $OCF_3$, alkyl or substituted alkyl, heterocycle or substituted heterocycle, aryl or substituted aryl, or $OR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula II,

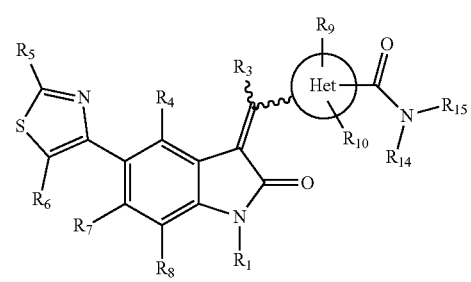

(II)

or an enantiomer, diastereomer, tautomer, or pharmaceutically acceptable salt or solvate thereof, for treating, therapeutically or prophylactically, obesity or overweight, and comorbidities closely associated therewith, including type II diabetes and the metabolic syndrome, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

R$_3$ and R$_{10}$ are each independently hydrogen, alkyl or substituted alkyl, cycloalkyl or substituted cycloalkyl, heterocycle or substituted heterocycle, aryl or substituted aryl;

R$_4$, R$_7$, and R$_8$ are each independently hydrogen, halogen, cyano, nitro, CF$_3$, OCF$_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$ R$_e$;

R$_5$ is alkyl or substituted alkyl, heterocycle or substituted heterocycle, aryl or substituted aryl amino or substituted amino;

R$_6$ and R$_9$ are each independently hydrogen, halogen, cyano, nitro, CF3, OCF3, alkyl or substituted alkyl, heterocycle or substituted heterocycle, aryl or substituted aryl, or ORa;

R$_{14}$ and R$_{15}$ are independently hydrogen, alkyl or substituted alkyl, cycloalkyl or substituted cycloalkyl, heterocycle or substituted heterocycle, or aryl or substituted aryl, or said R$_{14}$ and R$_{15}$ together with the N to which they are bonded optionally form a heterocycle or substituted heterocycle;

Ra is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula III,

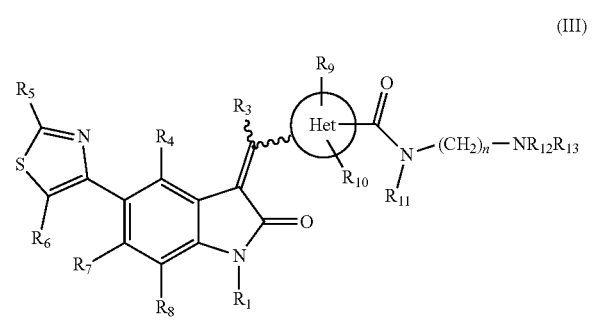

(III)

or an enantiomer, diastereomer, tautomer, or pharmaceutically acceptable salt or solvate thereof, for treating, therapeutically or prophylactically, obesity or overweight, and comorbidities closely associated therewith, including type II diabetes and the metabolic syndrome, wherein the symbols have the following meanings and are, for each occurrence, independently selected:

Het is a 5- or 6-membered aromatic ring containing at least one heteroatom selected from N, O and S;

R$_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$;

R$_3$ and R$_{10}$ are each independently hydrogen, alkyl or substituted alkyl, cycloalkyl or substituted cycloalkyl, heterocycle or substituted heterocycle, aryl or substituted aryl;

R$_4$, R$_7$, and R$_8$ are each independently hydrogen, halogen, cyano, nitro, CF$_3$, OCF$_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$ R$_e$;

R$_5$ is alkyl or substituted alkyl, heterocycle or substituted heterocycle, aryl or substituted aryl amino or substituted amino;

R$_6$ and R$_9$ are each independently hydrogen, halogen, cyano, nitro, CF$_3$, OCF$_3$, alkyl or substituted alkyl, heterocycle or substituted heterocycle, aryl or substituted aryl, or OR$_a$;

R$_{11}$ is hydrogen or C$_{1-4}$ alkyl;

R$_{12}$ and R$_{13}$ are independently hydrogen, alkyl or substituted alkyl, cycloalkyl or substituted cycloalkyl, heterocycle or substituted heterocycle, or aryl or substituted aryl, or said R$_{12}$ and R$_{13}$ together with the N to which they are bonded optionally form a heterocycle or substituted heterocycle;

n is an integer selected from 2, 3, 4, 5 and 6;

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula IV,

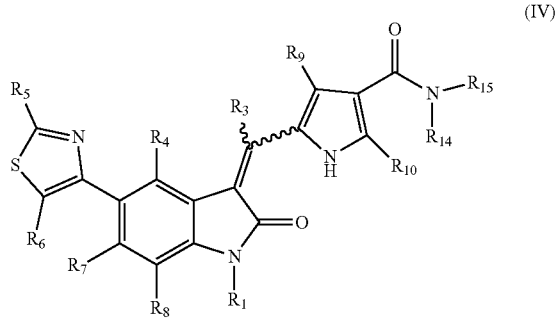

(IV)

or an enantiomer, diastereomer, tautomer, or pharmaceutically acceptable salt or solvate thereof, for treating, therapeutically or prophylactically, obesity or overweight, and comorbidities closely associated therewith, including type II diabetes and the metabolic syndrome, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl amino or substituted amino;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{14}$ and $R_{15}$ are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula V,

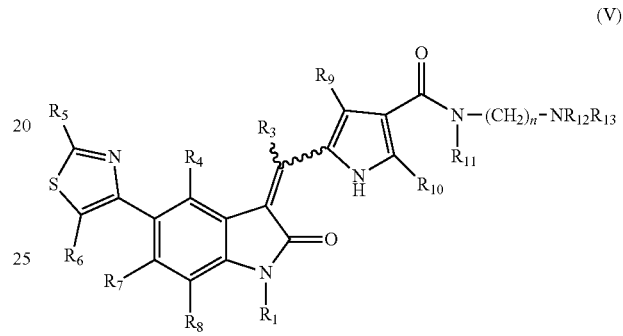

(V)

or an enantiomer, diastereomer, tautomer, or pharmaceutically acceptable salt or solvate thereof, for treating, therapeutically or prophylactically, obesity or overweight, and comorbidities closely associated therewith, including type II diabetes and the metabolic syndrome, wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is substituted alkyl, heterocycle or substituted heterocycle, aryl or substituted aryl amino or substituted amino;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{11}$ is hydrogen or $C_{1-4}$ alkyl;

$R_{12}$ and $R_{13}$ are independently hydrogen, alkyl or substituted alkyl, cycloalkyl or substituted cycloalkyl, heterocycle or substituted heterocycle, or aryl or substituted aryl, or said $R_{12}$ and $R_{13}$ together with the N to which they are bonded optionally form a heterocycle or substituted heterocycle;

n is an integer selected from 2, 3, 4, 5 and 6;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In various embodiments, the compound of the invention is one of the following eight compounds:

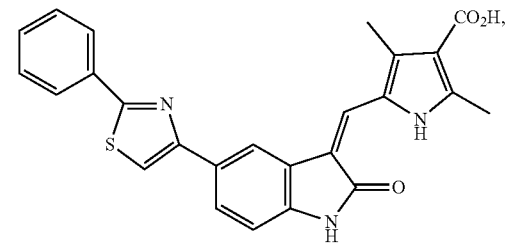
(9)

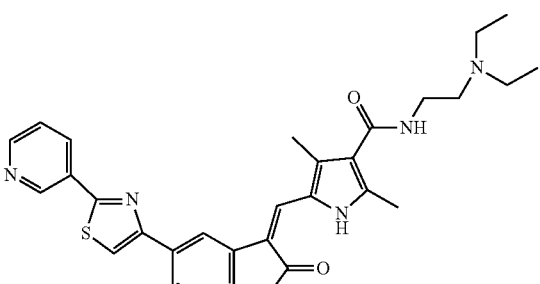
(15-3)

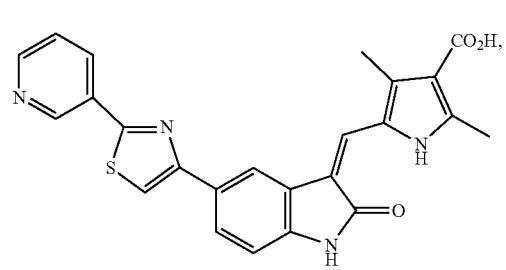
(12)

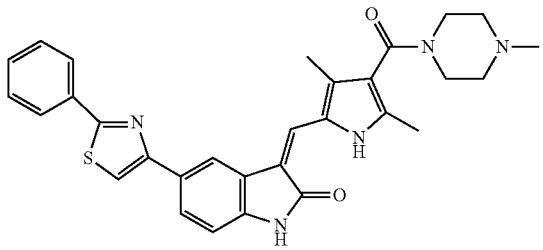
(10-1)

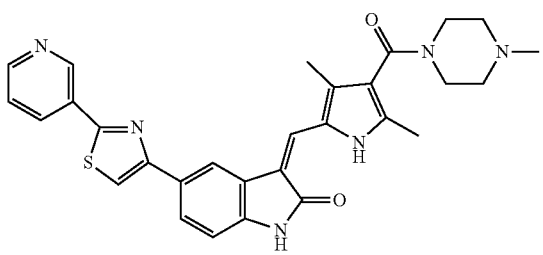
(15-1)

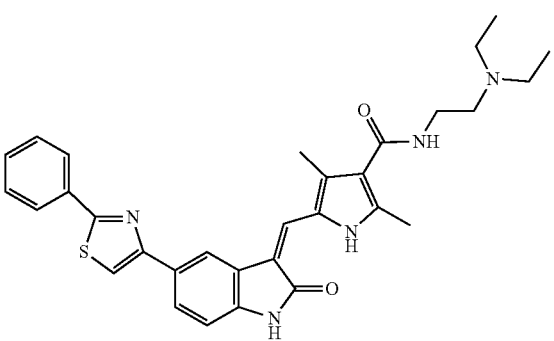
(14-3)

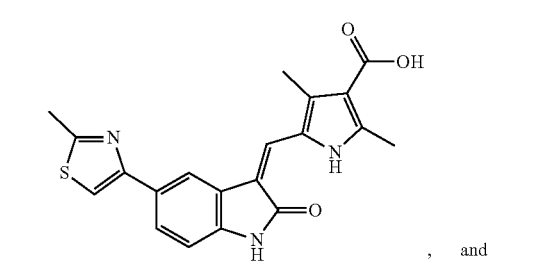
(5)

and

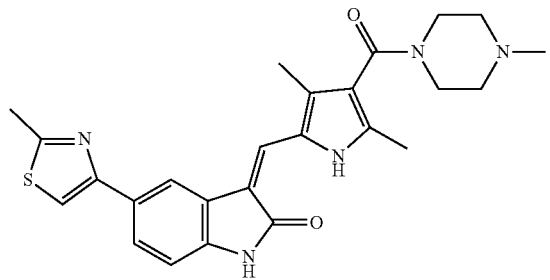
(7-1)

Item 1. In one aspect, the invention generally relates to the use of a compound of Formula VI,

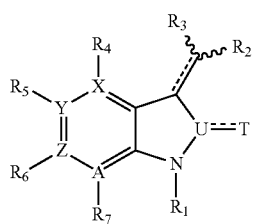

(VI)

or an enantiomer, diastereomer, tautomer, or pharmaceutically acceptable salt or solvate thereof, for treating, therapeutically or prophylactically, obesity or overweight, and comorbidities closely associated therewith, including type II diabetes and the metabolic syndrome, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_2$ is monocyclic or bicyclic heterocycle or substituted heterocycle, aryl or substituted aryl;

$R_3$ is hydrogen, alkyl or substituted alkyl, cycloalkyl or substituted cycloalkyl, heterocycle or substituted heterocycle, aryl or substituted aryl, halogen, $-OR_a$, $-C(O)R_a$, $-C(O)OR_a$, $-NR_aR_b$, or $S(O)_2NR_aR_b$;

$R_4$, $R_5$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

T is O, S or $R_a$;

U, V, and W are each independently a carbon, N, O, or S;

X, Y, Z, and A are each independently a carbon or N, with the proviso that the ring in which X, Y, Z, and A exist is aromatic;

with the provision that
one of $R_4$, $R_5$, $R_6$, and $R_7$ is substituted heterocycle or substituted aryl, and
$R_4$, $R_5$, $R_6$, or $R_7$ is absent if X, Y, Z, or A, respectively, is a heteroatom;

wherein
substituted heterocycle and substituted aryl in $R_4$, $R_5$, $R_6$, and $R_7$ is the following group:

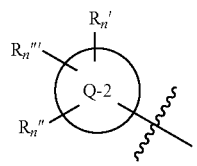

wherein

Q-2 is heterocycle, $C(=O)NR_bR_c$, or aryl;

$R_{n'}$, $R_{n''}$ and $R_{n'''}$ are each independently hydrogen, halogen, cyano, nitro, trihalomethyl, $OCF_3$, alkyl or substituted alkyl, $OR_a$, $SR_a$, $C(=O)R_a$, $C(=O)OR_a$, $NH_2$, $S(O)_2NH_2$, $NR_bR_c$, heterocycle or substituted heterocycle, or aryl or substituted aryl;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

Item 2. The compound of Item 1, wherein T is O or S,

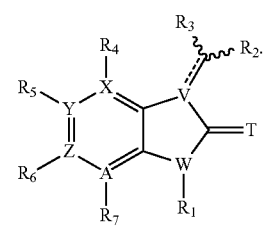

(VI-a)

Item 3. The compound of Item 2, wherein T is O,

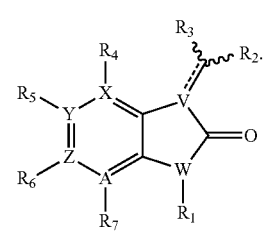

(VI-b)

Item 4. The compound of Item 2, V is carbon,

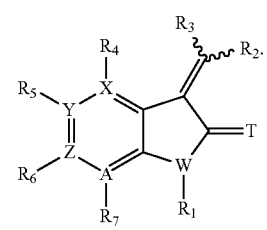

(VI-c)

Item 5. The compound of Item 2, W is N,

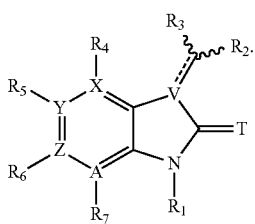
(VI-d)

Item 6. The compound of Item 5, T is O and W is N,

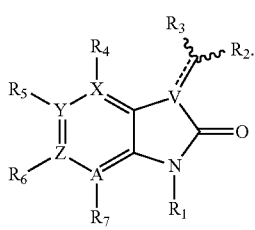
(VI-e)

Item 7. The compound of Item 4, T is O and V is carbon,

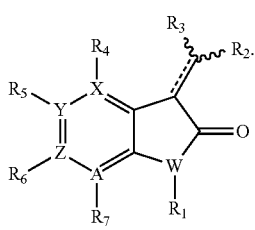
(VI-f)

Item 8. The compound of Item 1, U is carbon, V is carbon, W is N, and T is O,

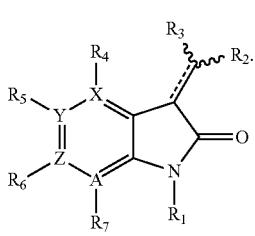
(VI-g)

Item 9. The compound of any one of Item 1 to Item 8, each of X, Y, Z, and A is carbon.

Item 10. The compound of any one of Item 1 to Item 9, $R_1$ is hydrogen.

Item 11. The compound of any one of Item 1 to Item 10, $R_2$ is

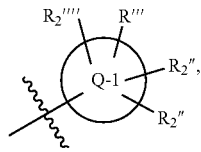

wherein

Q-1 is heterocycle or aryl;

$R_{2'}$, $R_{2''}$, $R_{2'''}$, and $R_{2''''}$, are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$.

Item 12. The compound of Item 10 or Item 11, one of X, Y, Z, and A is a heteroatom.

Item 13. The compound of any one of Items 10-12, Q-1 is heteroaryl.

Item 13'. The compound of any one of Items 10-12, Q-1 is phenyl.

Item 14. The compound of any one of Item 13, Q-1 is selected from the group consisting of pyrrole, furan, thiophene, pyridine, pyrimidine, pyrazine, pyridazine, imidazole, indole, pyrrolopyridinone, pyridone, pyrrolidine, piridinone, piperidine, and pyrroloazepinone.

Item 15. The compound of Item 14, Q-1 is selected from the group consisting of pyrrole, furan, thiophene, pyridine, pyrimidine, pyrazine, pyridazine, imidazole, indole, pyrrolopyridinone.

Item 16. The compound of Item 15, Q-1 is pyrrole.

Item 17. The compound of Item 13, Q-1 is pyridone, pyrrolidine, pyridinone, or piperidine.

Item 18. The compound of Item 17, Q-1 is pyridone or pyridinone.

Item 19. The compound of any one of item 11 to Item 18, $R_{2'}$, $R_{2''}$, $R_{2'''}$, and $R_{2''''}$ are independently absent, hydrogen, alkyl, substituted alkyl, substituted heterocycle, substituted aryl, $C(=O)OR_e$, or $C(=O)NR_bR_c$, wherein $R_b$ and $R_c$, are independently hydrogen, alkyl, substituted alkyl, substituted heterocycle, or said $R_b$ and $R_c$ together with the N to which they are bonded optionally form a heterocycle or substituted heterocycle, and $R_e$ is hydrogen.

Item 20. The compound of Item 19, one of $R_{2'}$, $R_{2''}$, $R_{2'''}$, and $R_{2''''}$ is $C(=O)NR_bR_c$, wherein $R_b$ is hydrogen, and $R_c$ is alkyl substituted with $NR_{bn}R_{cn}$ (wherein $R_{bn}$ and $R_{cn}$ are alkyl, or said $R_{bn}$ and $R_{cn}$ together with the N to which they are bonded optionally form a substituted heterocycle (wherein said heterocycle is piperidine, or morpholine)), or $R_b$ and $R_c$ together with the N to which they are bonded optionally form a substituted heterocycle (wherein said heterocycle is piperidine, or morpholine), and two of $R_{2'}$, $R_{2''}$, $R_{2'''}$, and $R_{2''''}$ are independently alkyl, and the other is hydrogen.

Item 21. The compound of Item 20, one of $R_{2'}$, $R_{2''}$, $R_{2'''}$, and $R_{2''''}$ is $C(=O)NR_bR_c$, wherein $NR_bR_c$ is 2-(di-ethyl amino) ethyl amino, 2-pyrrolidino ethyl amino, 4-methyl piperazinyl, or morpholino.

Item 21'. The compound of Item 16, Q-1 is pyrrole, one of $R_{2'}$, $R_{2''}$, $R_{2'''}$, and $R_{2''''}$ is absent, two of $R_{2'}$, $R_{2''}$, $R_{2'''}$, and $R_{2''''}$ are alkyl (e.g., methyl), and one of $R_{2'}$, $R_{2''}$, $R_{2'''}$, and $R_{2''''}$ is $C(=O)NR_bR_c$.

Item 21''. The compound of Item 21', wherein $R_b$ is hydrogen, and $R_c$ is alkyl substituted with $NR_{bn}R_{cn}$ (wherein $R_{bn}$ and $R_{cn}$ are alkyl, or said $R_{bn}$ and $R_{cn}$ together with the N to which they are bonded optionally form a substituted heterocycle (wherein said heterocycle is piperidine, or morpholine)).

Item 21'''. The compound of Item 21'', wherein $NR_bR_c$ is 2-(di-ethyl amino) ethyl amino, or 2-pyrrolidino ethyl amino.

Item 21''''. The compound of Item 21', wherein $R_b$ and $R_c$ together with the N to which they are bonded optionally form a heterocycle or substituted heterocycle.

Item 21'''''. The compound of Item 21'''', wherein $NR_bR_c$ is 4-methyl piperazinyl, or morpholino.

Item 22. The compound of any one of Item 1 to Item 21, $R_4$, $R_5$, $R_6$, and $R_7$ are each independently hydrogen, halogen, cyano, nitro, alkyl or substituted alkyl, $OR_a$, $NR_bR_c$, $C(=O)OR_e$, $C(=O)R_a$, $C(=O)NR_bR_c$, or

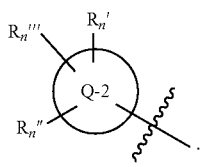

Item 23. The compound of any one of Item 1 to Item 22, $R_4$, $R_5$, $R_6$, and $R_7$ are each independently hydrogen, halogen, cyano, nitro, alkyl, $OR_a$, $NR_bR_c$, $C(=O)OR_e$, $C(=O)R_a$, $C(=O)NR_bR_c$, (wherein $R_a$ is hydrogen, or alkyl or substituted alkyl, $R_b$ and $R_c$ are independently hydrogen, or alkyl or substituted alkyl, and $R_e$ is alkyl or substituted alkyl (substituted alkyl is optionally substituted with one or more substituent(s) selected from the group consisting of hydroxy, amino, nitro, cyano, halogen, alkoxy, alkylcarbonyl, alkoxycarbonyl, aminocarbonyl, aryl, cycloalkyl, and heterocycle.)), and

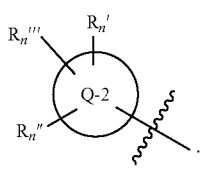

Item 24. The compound of any one of Item 23, one of $R_4$, $R_5$, $R_6$, and $R_7$ is

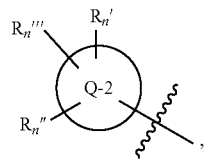

the others of $R_4$, $R_5$, $R_6$, and $R_7$ are each independently hydrogen.

Item 25. The compound of Item 24, Q-2 is selected from the group consisting of pyrrole, furan, thiophene, imidazole, pyrazole, oxazole, isoxazole, thiazole, isothiazole, triazole, thiadiazole, oxadiazole, pyrrolidine, piperidine, azepane, tetrahydrofuran, oxane, oxepane, indole, indolinone, indazole, benzothiazole, quinoline, quinazoline, quinoxaline, imidazopyridine, imidazopyridazine, pyrazolopyridine, pyrazolopyrimidine, phthalazinone, and phenyl.

Item 26. The compound of Item 25, Q-2 is selected from the group consisting of pyrrole, furan, thiophene, imidazole, pyrazole, oxazole, isoxazole, thiazole, isothiazole, triazole, thiadiazole, oxadiazole, pyrrolidine, piperidine, azepane, tetrahydrofuran, oxane, oxepane, indole, indolinone, indazole, benzothiazole, quinoline, quinazoline, quinoxaline, imidazopyridine, imidazopyridazine, pyrazolopyridine, pyrazolopyrimidine, and phthalazinone.

Item 27. The compound of Item 26, Q-2 is selected from the group consisting of thiophene, imidazole, oxazole, thiazole, thiadiazole, piperidine, and pyrazole.

Item 27'. The compound of Item 26, Q-2 is selected from the group consisting of indole, indolinone, indazole, benzothiazole, quinoline, quinazoline, quinoxaline, imidazopyridine, imidazopyridazine, pyrazolopyridine, pyrazolopyrimidine, and phthalazinone.

Item 28. The compound of Item 27, Q-2 is thiazole.
Item 29. The compound of Item 27, Q-2 is imidazole.
Item 30. The compound of Item 27, Q-2 is piperidine.
Item 31. The compound of Item 27, Q-2 is pyrazole.

Item 32. The compound of any one of Item 22 to 25, $R_{n'}$ is pyrrolidinyl, piperidinyl, azepanyl, tetrahydrofuranyl, oxanyl, oxepanyl, pyranyl, phenyl, thiophenyl, pyrazinyl, pyrimidinyl, pyridazinyl, or pyridyl (said piperidinyl, pyranyl, phenyl, thiophenyl, pyrazinyl, pyrimidinyl, pyridazinyl, and pyridyl are optionally substituted with halogen, cyano, nitro, alkyl or substituted alkyl, $OR_a$, $NR_bR_c$, $C(=O)OR_e$, $C(=O)R_a$, or $C(=O)NR_bR_c$ (wherein $R_a$ is hydrogen, or alkyl or substituted alkyl, $R_b$ and $R_c$ are independently hydrogen, or alkyl or substituted alkyl, and $R_e$ is alkyl or substituted alkyl (substituted alkyl is optionally substituted with one or more substituent(s) selected from the group consisting of hydroxy, amino, nitro, cyano, halogen, alkoxy, alkylcarbonyl, alkoxycarbonyl, aminocarbonyl, aryl, cycloalkyl, and heterocycle.)), and $R_{n''}$ and $R_{n'''}$ are independently hydrogen, or alkyl or substituted alkyl (substituted alkyl is optionally substituted with one or more substituent(s) selected from the group consisting of hydroxy, amino, nitro, cyano, halogen, alkoxy, alkylcarbonyl, alkoxycarbonyl, aminocarbonyl, aryl, cycloalkyl, and heterocycle).

Item 32'. The compound of any one of Item 22 to 25, $R_{n'}$, $R_{n''}$ and $R_{n'''}$ are independently hydrogen, alkyl, or methoxy.

Item 32". The compound of any one of Item 22 to 25, $R_{n'}$, $R_{n''}$ and $R_{n'''}$ are each hydrogen.

Item 33. The compound of Item 32, $R_{n'}$ is pyrrolidinyl, piperidinyl, tetrahydrofuranyl, pyranyl, phenyl, pyrazinyl, pyrimidinyl, or pyridyl (said piperidinyl, pyranyl, phenyl, pyrazinyl, pyrimidinyl, and pyridyl are optionally substituted with halogen, cyano, alkyl or substituted alkyl, $OR_a$, or $C(=O)OR_e$ (wherein $R_a$ is hydrogen, or alkyl or substituted alkyl, and $R_e$ is alkyl or substituted alkyl (substituted alkyl is optionally substituted with one or more substituent(s) selected from the group consisting of hydroxy, amino, nitro, cyano, halogen, alkoxy, alkylcarbonyl, alkoxycarbonyl, aminocarbonyl, aryl, cycloalkyl, and heterocycle.)), and $R_{n''}$ and $R_{n'''}$ are independently hydrogen, alkyl, or amino.

Item 33'. The compound of Item 33, $R_{n'}$ is phenyl or substituted phenyl, and $R_{n''}$ and $R_{n'''}$ are independently hydrogen, or alkyl, or amino.

Item 34. The compound of Item 33, $R_{n''}$ and $R_{n'''}$ are independently hydrogen or alkyl.

Item 35. The compound of Item 32 or 33, Q-2 is selected from the group consisting of the following group:

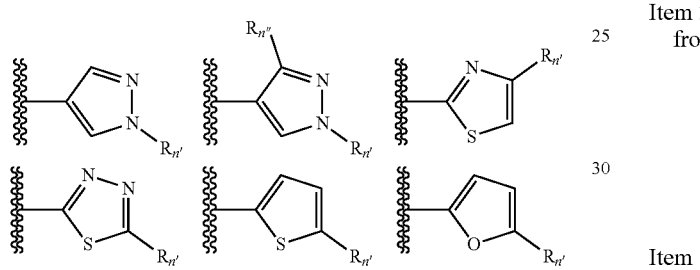

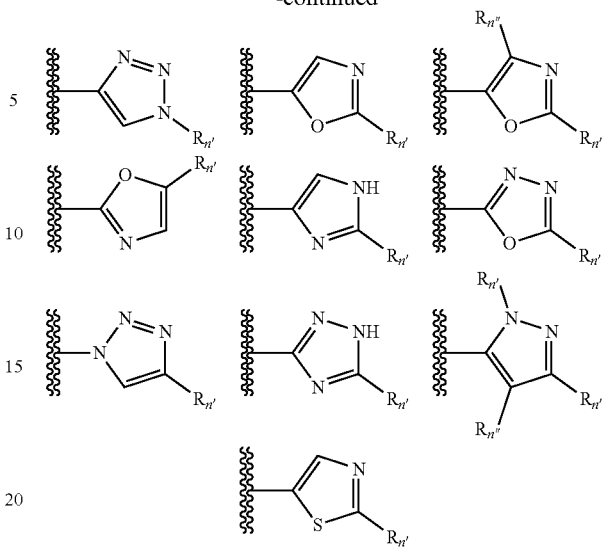

Item 36. The compound of Item 32 or 33, Q-2 is selected from the group consisting of the following group:

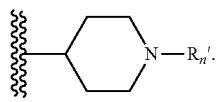

Item 37. The compound of any one of Item 1, selected from the group consisting of:

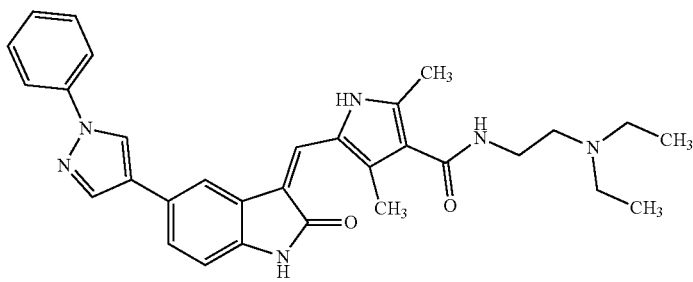

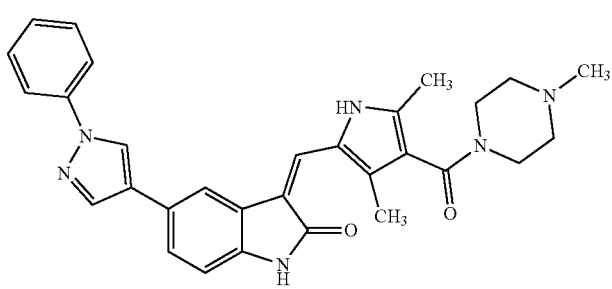

-continued
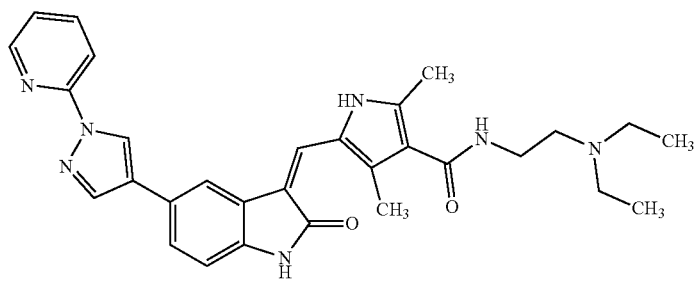
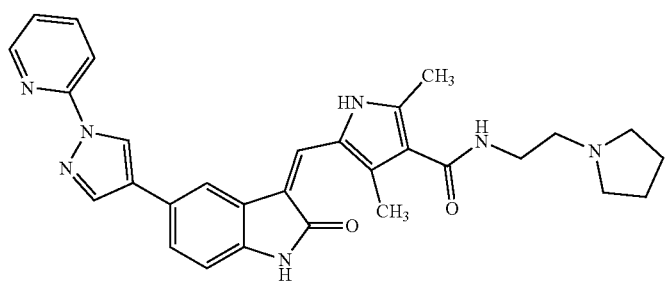
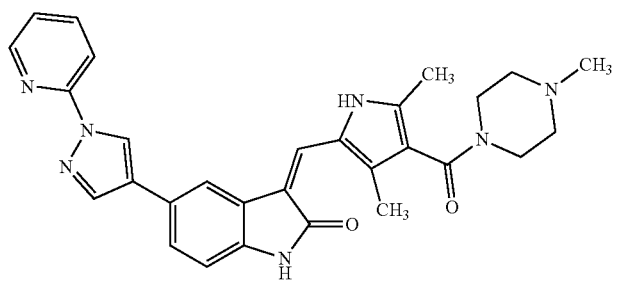
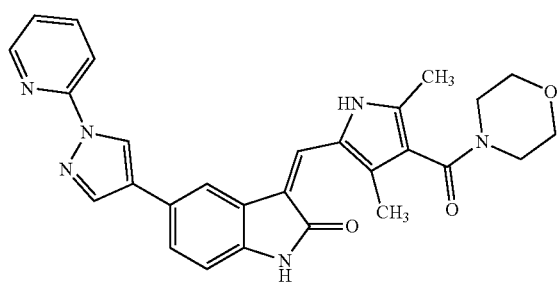
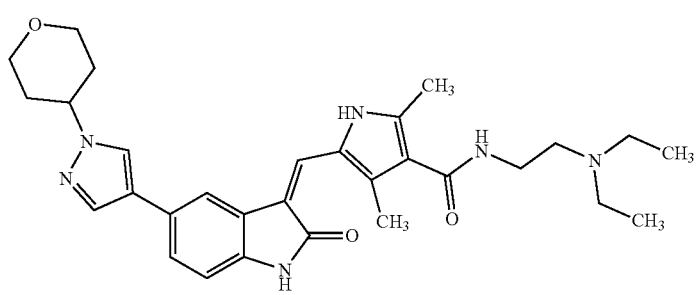
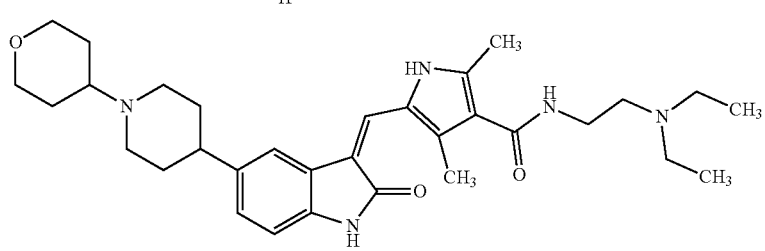

-continued
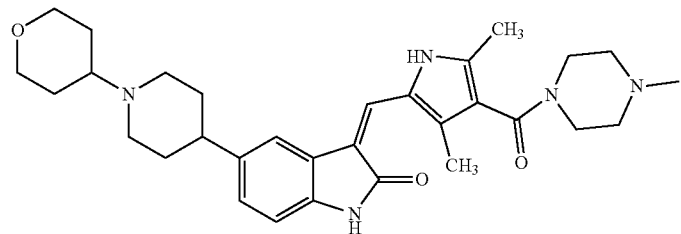
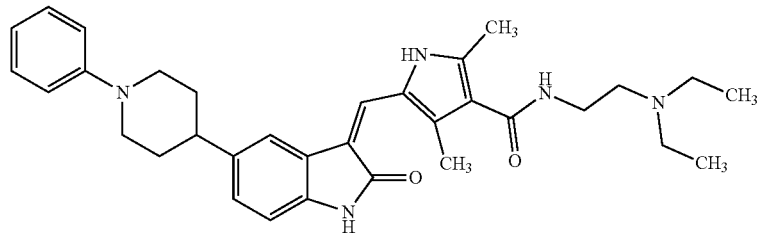
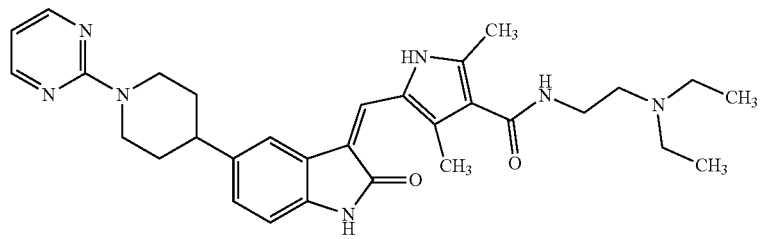
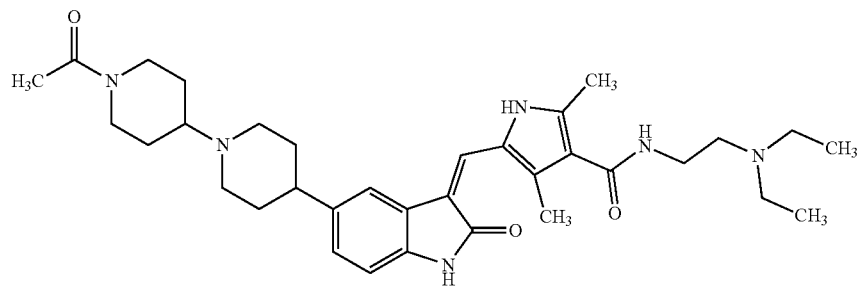
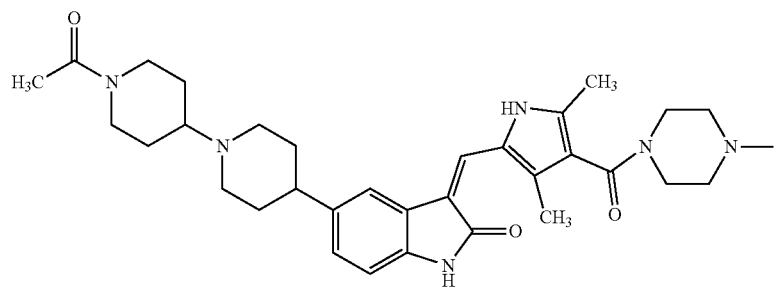
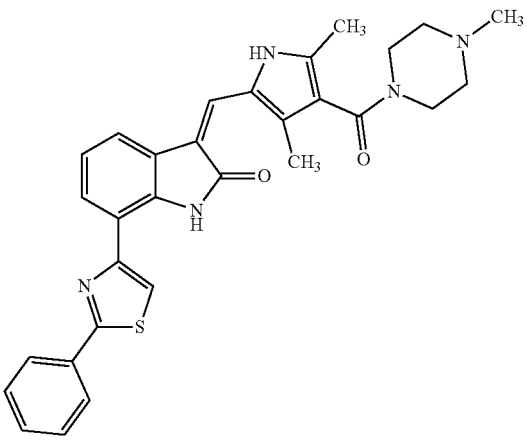

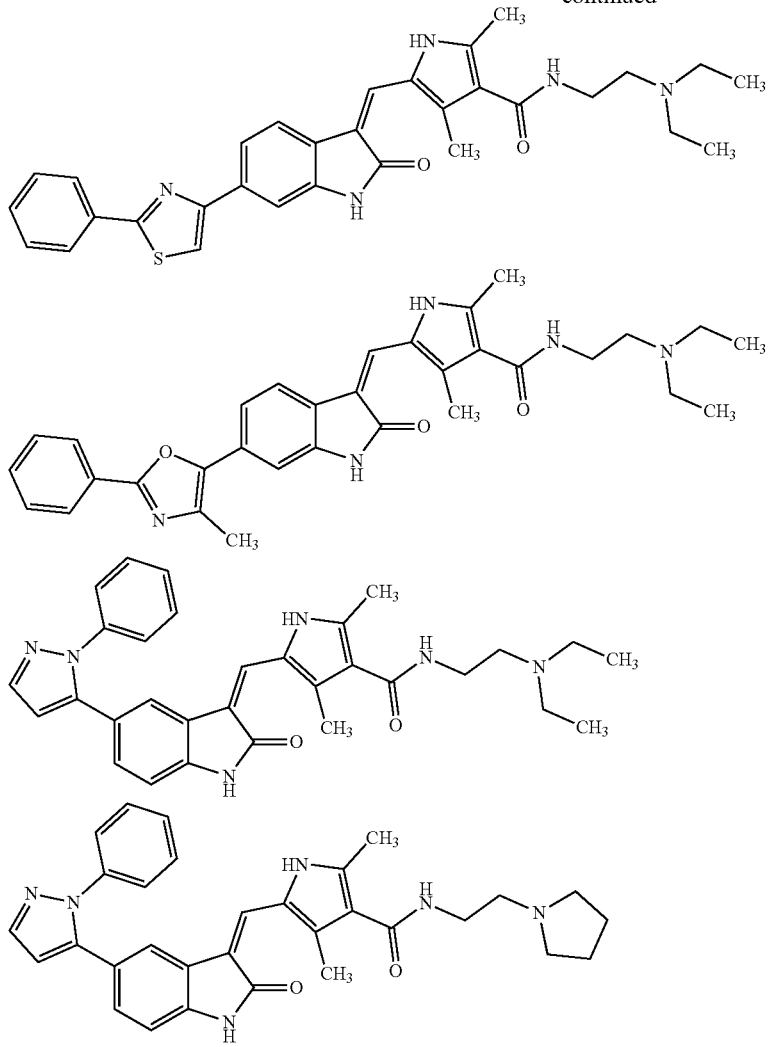

In another aspect, the invention generally relates to the use of a compound of Formula VII,

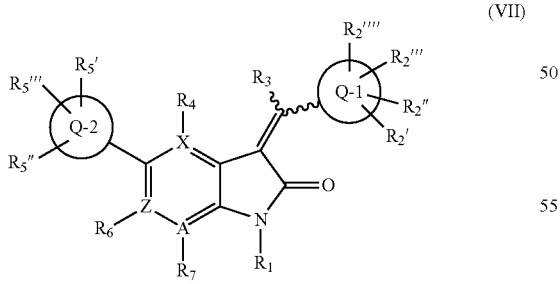

or an enantiomer, diastereomer, tautomer, or pharmaceutically acceptable salt or solvate thereof, for treating, therapeutically or prophylactically, obesity or overweight, and comorbidities closely associated therewith, including type II diabetes and the metabolic syndrome, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2 R_e$, $S(=O)_2 OR_e$, $C(=O)OR_d$, $C(=O)R_a$, or $C(=O) NR_b R_c$;

$R_3$ is hydrogen, alkyl or substituted alkyl, cycloalkyl or substituted cycloalkyl, heterocycle or substituted heterocycle, aryl or substituted aryl, halogen, $-OR_a$, $-C(O)R_a$, $-C(O)OR_a$, $-NR_a R_b$, or $S(O)_2 NR_a R_b$;

$R_4$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2 R_e$, $P(=O)_2 R_e$, $S(=O)_2 OR_e$, $P(=O)_2 OR_e$, $NR_b R_c$, $NR_b S(=O)_2 R_e$, $NR_b P(=O)_2 R_e$, $S(=O)_2 NR_b R_c$, $P(=O)_2 NR_b R_c$, $C(=O)OR_e$, $C(=O) R_a$, $C(=O)NR_b R_c$, $OC(=O)R_a$, $OC(=O)NR_b R_c$, $NR_b C(=O)OR_e$, $NR_d C(=O)NR_b R_c$, $NR_d S(=O)_2 NR_b R_c$, $NR_d P(=O)_2 NR_b R_c$, $NR_b C(=O)R_a$, or $NR_b P(=O)_2 R_e$;

X, Z, and A are each independently a carbon or N, with the proviso that the ring in which X, Z, and A exist is aromatic;

Q-1 and Q-2 are independently heterocycle, C(=O)NR$_b$R$_c$ or aryl;

R$_2'$, R$_2''$, R$_2'''$ and R$_2''''$ are each independently absent, hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, R$_5'$, R$_5''$ and R$_5'''$ are each independently hydrogen, halogen, cyano, nitro, CF$_3$, OCF$_3$, alkyl or substituted alkyl, OR$_a$, SR$_a$, C(=O)R$_a$, C(=O)OR$_a$, NH$_2$, S(O)$_2$NH$_2$, NR$_b$R$_c$, heterocycle or substituted heterocycle, or aryl or substituted aryl;

wherein

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the compound of formula (VII), wherein each of X, Z, and A is carbon. In some embodiments, the compound of formula (VII), wherein one of X, Z, and A is a heteroatom.

In some embodiments, the compound of formula (VII) has the formula (VII-a)

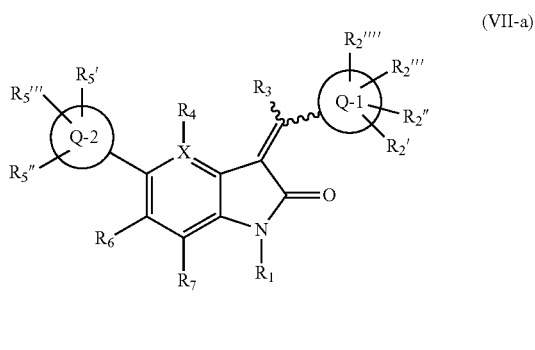

(VII-a)

wherein R$_1$, R$_2'$, R$_2''$, R$_2'''$, R$_2''''$, R$_3$, R$_4$, R$_5'$, R$_5''$, R$_5'''$, R$_6$, R$_7$, X, Q-1, and Q-2 are the same as the above definitions.

In some embodiments, the compound of formula (VII) has the formula (VII-b)

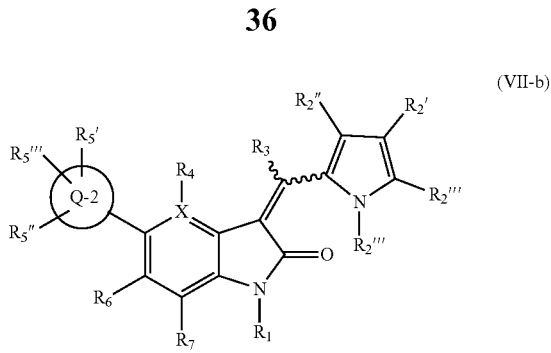

(VII-b)

wherein

R$_2'$, R$_2''$, R$_2'''$ are each independently absent, hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, and R$_2''''$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, C(=O)NR$_b$R$_c$, R$_1$, R$_3$, R$_4$, R$_5'$, R$_5''$, R$_5'''$, R$_6$, R$_7$, X, and Q-2 are the same as the above definitions.

In some embodiments, the compound of formula (VII-b), wherein X is C. In some embodiments, the compound of formula (VII-b), wherein X is N. In some embodiments, the compound of formula (VII-b), wherein R$_2''''$ is H. In some embodiments, the compound of formula (VII-b), wherein R$_2''$ and R$_2'''$ are each independently hydrogen. In some embodiments, the compound of formula (VII-b), wherein R$_2''$ and R$_2'''$ are each independently methyl.

In some embodiments, the compound of formula (VII) has the formula (VII-c)

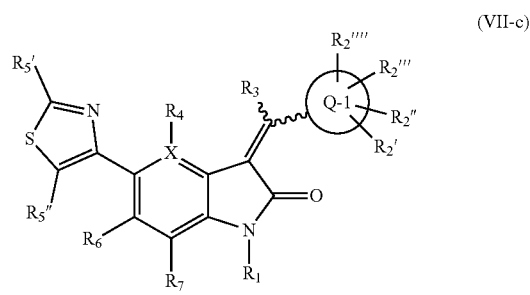

(VII-c)

wherein

R$_1$, R$_2'$, R$_2''$, R$_2'''$, R$_2''''$, R$_3$, R$_4$, R$_5'$, R$_5''$, R$_6$, R$_7$, X, and Q-1 are the same as the above definitions.

In some embodiments, the compound of formula (VII) has the formula (VII-d)

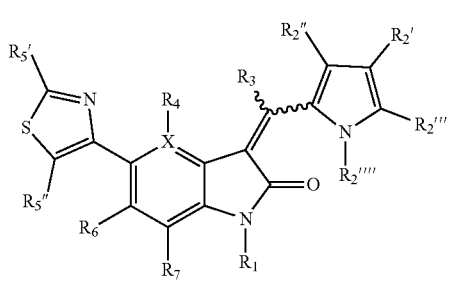

(VII-d)

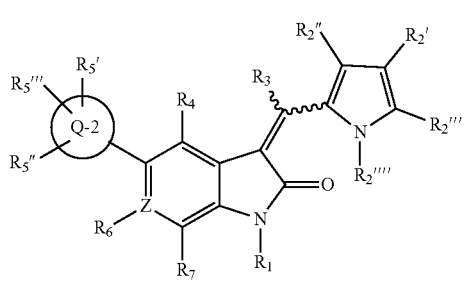

(VII-f)

wherein

X is C or N, $R_{2'}$, $R_{2''}$, $R_{2'''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2 R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, $C(=O)NR_bR_c$, and $R_1$, $R_3$, $R_4$, $R_{5'}$, $R_{5''}$, $R_6$, and $R_7$, are the same as the above definitions.

In some embodiments, the compound of formula (VII) has the formula (VII-e)

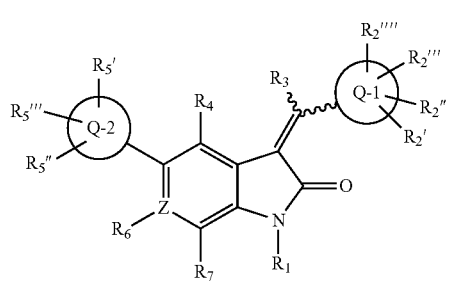

(VII-e)

wherein

Z is C or N, $R_1$, $R_{2'}$, $R_{2''}$, $R_{2'''}$, $R_{2''''}$, $R_3$, $R_4$, $R_{5'}$, $R_{5''}$, $R_{5'''}$, $R_6$, $R_7$, Q-1, and Q-2 are the same as the above definitions.

In some embodiments, the compound of formula (VII) has the formula (VII-f)

wherein

Z is C or N, $R_{2'}$, $R_{2''}$, $R_{2'''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2 R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, $C(=O)NR_bR_c$, and $R_1$, $R_3$, $R_4$, $R_{5'}$, $R_{5''}$, $R_{5'''}$, $R_6$, $R_7$, and Q-2 are the same as the above definitions.

In some embodiments, the compound of formula (VII-f), wherein Z is C. In some embodiments, the compound of formula (VII-f), wherein Z is N. In some embodiments, the compound of formula (VII-f), wherein $R_{2''''}$ is H. In some embodiments, the compound of formula (VII-f), wherein $R_{2''}$ and $R_{2'''}$ are each independently hydrogen. In some embodiments, the compound of formula (VII-f), wherein $R_{2''}$ and $R_{2'''}$ are each independently methyl.

In some embodiments, the compound of formula (VII) has the formula (VII-g)

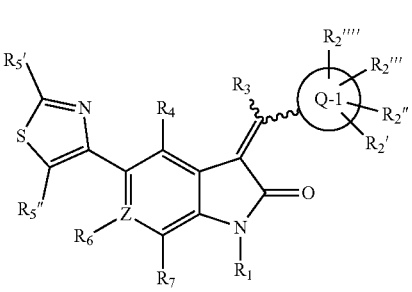

(VII-g)

wherein

Z is C or N, $R_1$, $R_{2'}$, $R_{2''}$, $R_{2'''}$, $R_{2''''}$, $R_3$, $R_4$, $R_{5'}$, $R_{5''}$, $R_6$, $R_7$, and Q-1 are the same as the above definitions.

In some embodiments, the compound of formula (VII) has the formula (VII-h)

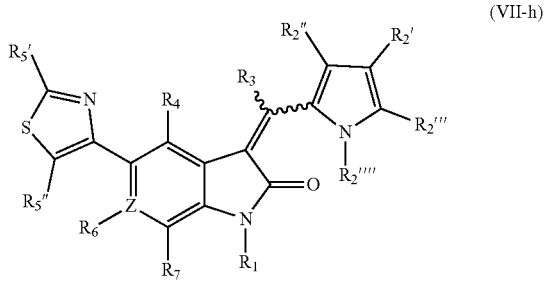

(VII-h)

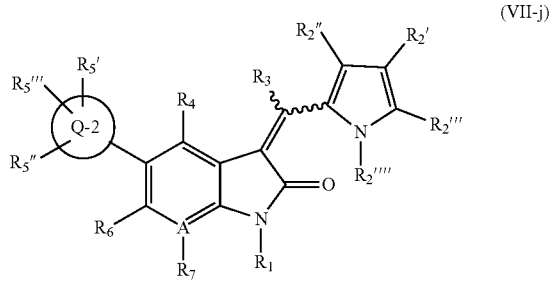

(VII-j)

wherein

Z is C or N,

R$_2$', R$_2$'', R$_2$''' are each independently absent, hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$ R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, and R$_2$'''' is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, C(=O)NR$_b$R$_c$, and R$_1$, R$_3$, R$_4$, R$_5$', R$_5$'', R$_6$, and R$_7$, are the same as the above definitions.

In some embodiments, the compound of formula (VII) has the formula (VII-i)

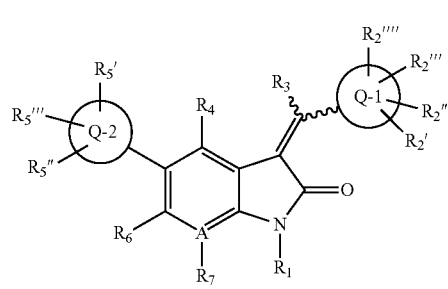

(VII-i)

wherein

A is C or N,

R$_1$, R$_2$', R$_2$'', R$_2$''', R$_2$'''', R$_3$, R$_4$, R$_5$', R$_5$'', R$_5$''', R$_6$, R$_7$, Q-1, and Q-2 are the same as the above definitions.

In some embodiments, the compound of formula (VII) has the formula (VII-j)

wherein

A is C or N,

R$_2$', R$_2$'', R$_2$''' are each independently absent, hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$ R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, and R$_2$'''' is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, C(=O)NR$_b$R$_c$, and R$_1$, R$_3$, R$_4$, R$_5$', R$_5$'', R$_5$''', R$_6$, R$_7$, and Q-2 are the same as the above definitions.

In some embodiments, the compound of formula (VII-j), wherein A is C. In some embodiments, the compound of formula (VII-j), wherein A is N. In some embodiments, the compound of formula (VII-j), wherein R$_2$'''' is H. In some embodiments, the compound of formula (VII-j), wherein R$_2$'' and R$_2$''' are each independently hydrogen. In some embodiments, the compound of formula (VII-j), wherein R$_2$'' and R$_2$''' are each independently methyl.

In some embodiments, the compound of formula (VII) has the formula (VII-k)

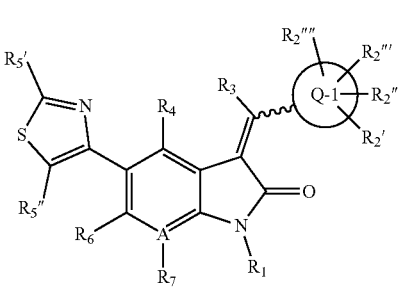

(VII-k)

wherein

A is C or N,

R$_1$, R$_2$', R$_2$'', R$_2$''', R$_2$'''', R$_3$, R$_4$, R$_5$', R$_5$'', R$_6$, R$_7$, and Q-1 are the same as the above definitions.

In some embodiments, the compound of formula (VII) has the formula (VII-1)

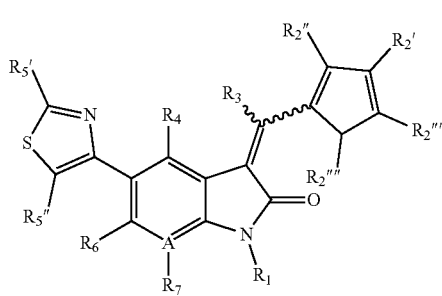

(VII-l)

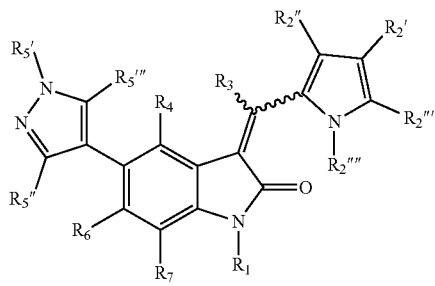

(VII-n)

wherein

A is C or N, $R_{2'}$, $R_{2''}$, $R_{2'''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, $C(=O)NR_bR_c$, and $R_1$, $R_3$, $R_4$, $R_{5'}$, $R_{5''}$, $R_6$, and $R_7$, are the same as the above definitions.

In some embodiments, the compound of formula (VII) has the formula (VII-m)

(VII-m)

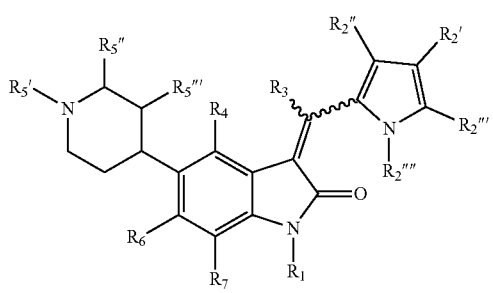

wherein $R_1$, $R_{2'}$, $R_{2''}$, $R_{2'''}$, $R_{2''''}$, $R_3$, $R_4$, $R_{5'}$, $R_{5''}$, $R_{5'''}$, $R_6$, and $R_7$, are the same as the above definitions.

In some embodiments, the compound of formula (VII) has the formula (VII-n)

wherein $R_1$, $R_{2'}$, $R_{2''}$, $R_{2'''}$, $R_{2''''}$, $R_3$, $R_4$, $R_{5'}$, $R_{5''}$, $R_{5'''}$, $R_6$, and $R_7$, are the same as the above definitions.

In some embodiments, the compound of formula (VII) has the formula (VII-o)

(VII-o)

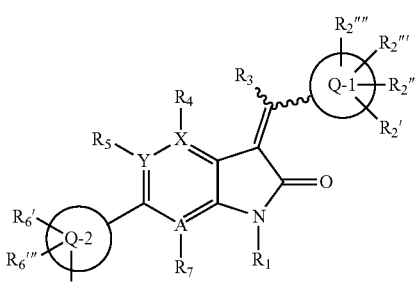

wherein $R_1$, $R_{2'}$, $R_{2''}$, $R_{2'''}$, $R_{2''''}$, $R_3$, $R_4$, $R_{5'}$, $R_{5''}$, $R_{5'''}$, $R_6$, and $R_7$, are the same as the above definitions.

In some embodiments, the invention generally relates to the use of a compound of Formula VIII, (VIII)

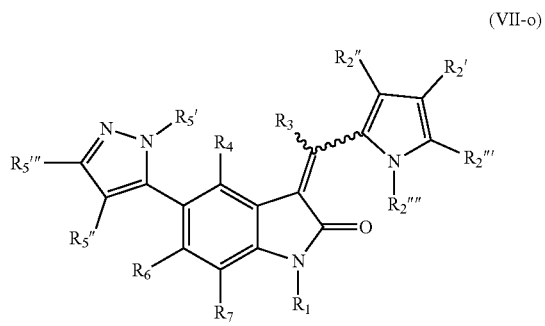

or an enantiomer, diastereomer, tautomer, or pharmaceutically acceptable salt or solvate thereof, for treating, therapeutically or prophylactically, obesity or overweight, and comorbidities closely associated therewith, including type II diabetes and metabolic syndrome, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

43

R₃ is hydrogen, alkyl or substituted alkyl, cycloalkyl or substituted cycloalkyl, heterocycle or substituted heterocycle, aryl or substituted aryl, halogen, —OR$_a$, —C(O)R$_a$, —C(O)OR$_a$, —NR$_a$R$_b$, or S(O)$_2$NR$_a$R$_b$;

R₄, R₅, and R₇ are each independently hydrogen, halogen, cyano, nitro, trihalomethyl, OCF₃, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$;

X, Y, and A are each independently a carbon or N, with the proviso that the ring in which X, Y, and A exist is aromatic;

Q-1 and Q-2 are each independently heterocycle, C(=O)NR$_b$R$_c$ or aryl;

R$_2$', R$_2$'', R$_2$''' and R$_2$'''' are each independently absent, hydrogen, halogen, cyano, nitro, trihalomethyl, OCF₃, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, R$_6$', R$_6$'' and R$_6$''' are each independently hydrogen, halogen, cyano, nitro, trihalomethyl, OCF₃, alkyl or substituted alkyl, OR$_a$, SR$_a$, C(=O)R$_a$, C(=O)OR$_a$, NH₂, S(O)$_2$NH₂, heterocycle or substituted heterocycle, or aryl or substituted aryl;

wherein

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula IX,

44

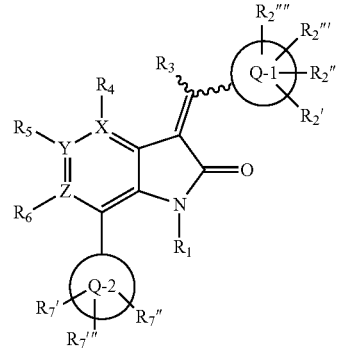

(IX)

or an enantiomer, diastereomer, tautomer, or pharmaceutically acceptable salt or solvate thereof, for treating, therapeutically or prophylactically, obesity or overweight, and comorbidities closely associated therewith, including type II diabetes and the metabolic syndrome, wherein R₁ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$;

R₃ is hydrogen, alkyl or substituted alkyl, cycloalkyl or substituted cycloalkyl, heterocycle or substituted heterocycle, aryl or substituted aryl, halogen, —OR$_a$, —C(O)R$_a$, —C(O)OR$_a$, —NR$_a$R$_b$, or S(O)$_2$NR$_a$R$_b$;

R₄, R₅, and R₆ are each independently hydrogen, halogen, cyano, nitro, trihalomethyl, OCF₃, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$;

X, Y, and Z are each independently a carbon or N, with the proviso that the ring in which X, Y, and Z exist is aromatic;

Q-1 and Q-2 are each independently heterocycle, C(=O)NR$_b$R$_c$ or aryl;

R$_2$', R$_2$'', R$_2$''' and R$_2$'''' are each independently absent, hydrogen, halogen, cyano, nitro, trihalomethyl, OCF₃, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, R$_7$', R$_7$'' and R$_7$''' are each independently hydrogen, halogen, cyano, nitro, trihalomethyl, OCF₃, alkyl or substituted alkyl, OR$_a$, SR$_a$, C(=O)R$_a$, C(=O)OR$_a$, NH₂, S(O)$_2$NH₂, heterocycle or substituted heterocycle, or aryl or substituted aryl;

wherein
R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula X

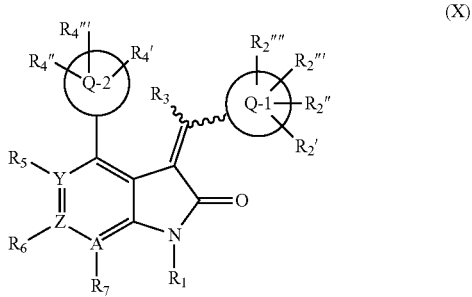

(X)

or an enantiomer, diastereomer, tautomer, or pharmaceutically acceptable salt or solvate thereof, for treating, therapeutically or prophylactically, obesity or overweight, and comorbidities closely associated therewith, including type II diabetes and the metabolic syndrome, wherein
R$_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$;

R$_3$ is hydrogen, alkyl or substituted alkyl, cycloalkyl or substituted cycloalkyl, heterocycle or substituted heterocycle, aryl or substituted aryl, halogen, —OR$_a$, —C(O)R$_a$, —C(O)OR$_a$, —NR$_a$R$_b$, or S(O)$_2$NR$_a$R$_b$;

R$_5$, R$_6$, and R$_7$ are each independently hydrogen, halogen, cyano, nitro, trihalomethyl, OCF$_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$;

Y, Z and A are each independently a carbon or N, with the proviso that the ring in which Y, Z and A exist is aromatic;

Q-1 and Q-2 are each independently heterocycle, C(=O)NR$_b$R$_c$ or aryl;

R$_2'$, R$_2''$, R$_2'''$, and R$_2''''$ are each independently absent, hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, R$_4'$, R$_4''$ and R$_4'''$ are each independently hydrogen, halogen, cyano, nitro, trihalomethyl, OCF$_3$, alkyl or substituted alkyl, OR$_a$, SR$_a$, C(=O)R$_a$, C(=O)OR$_a$, NH$_2$, S(O)$_2$NH$_2$, heterocycle or substituted heterocycle, or aryl or substituted aryl;

wherein
R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In various embodiments, the compound of the invention is one of the following fifteen compounds:

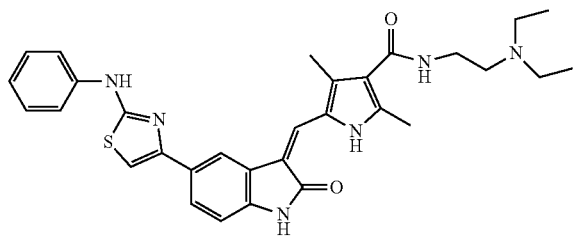

(13-3-1)

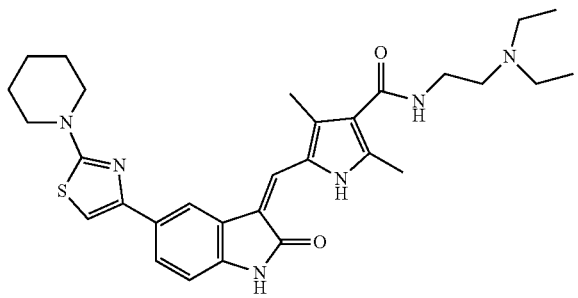

(13-3-2)

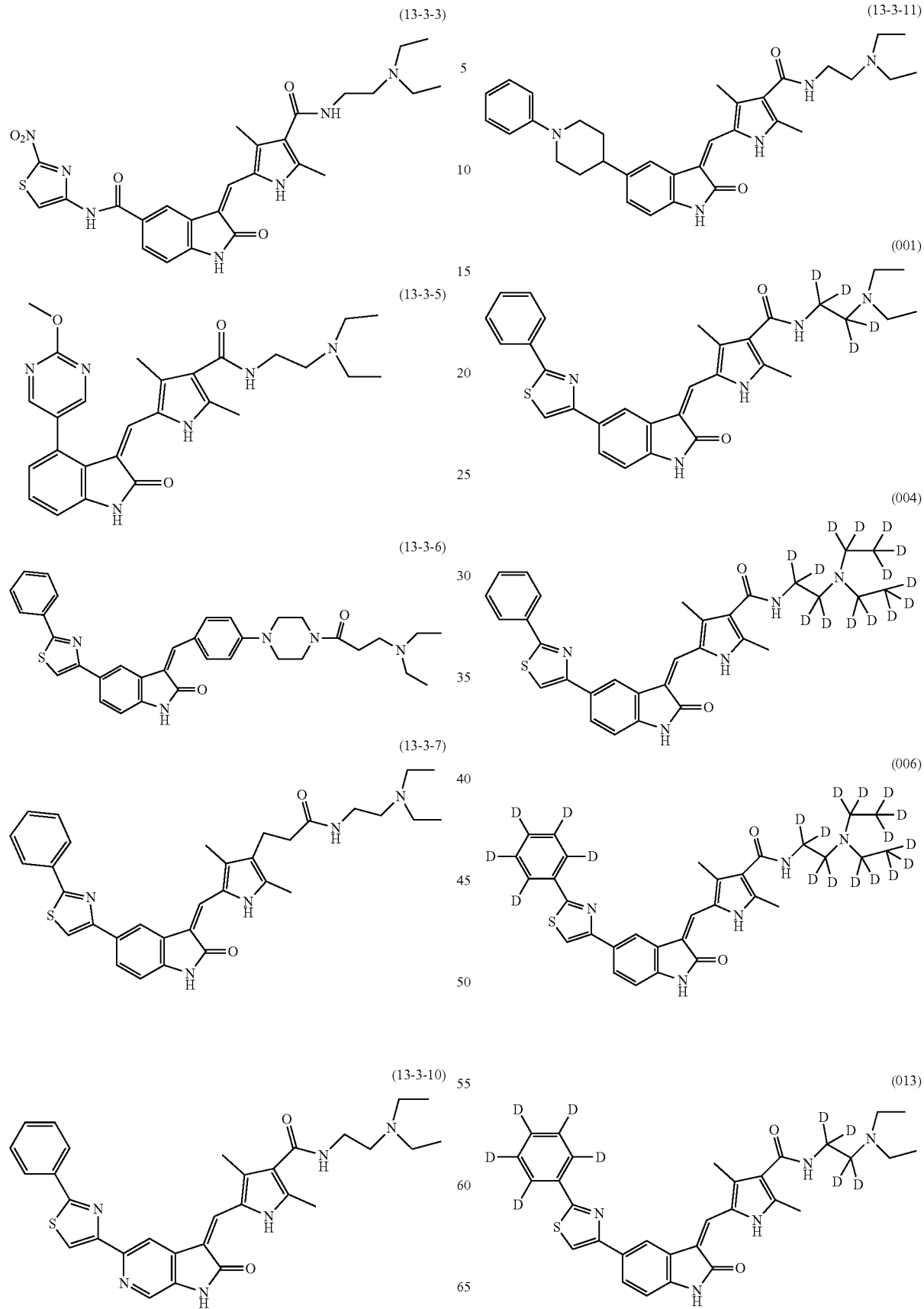

-continued

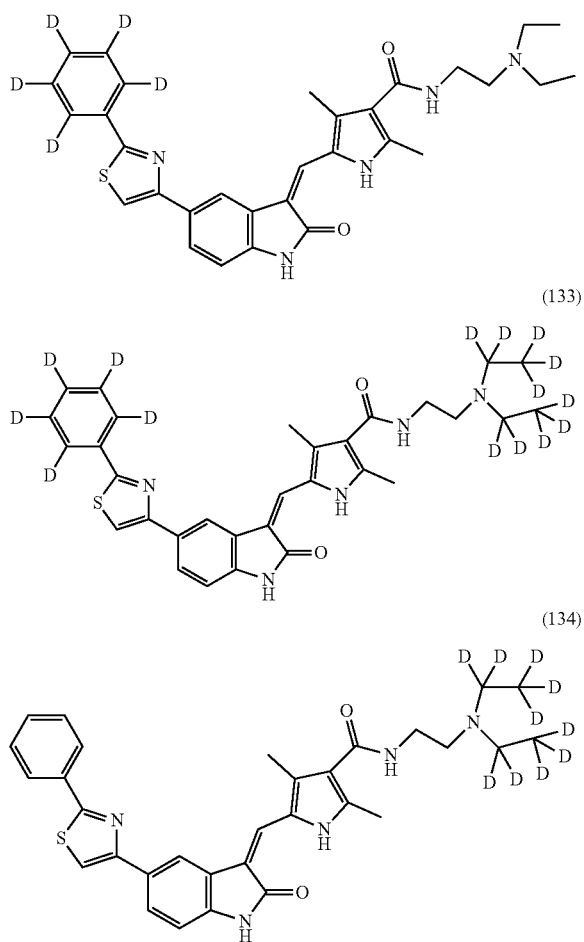

Synthesis

Exemplary methods for preparing compounds of the invention are provided in later sections, but the present invention is not intended to be limited thereto.

In the following exemplary methods for chemically synthesizing compounds of the invention, the starting materials and the intermediates of the reaction may be isolated and purified if desired using conventional techniques, including but not limited to filtration, distillation, crystallization, chromatography and the like.

The materials of invention can be characterized by using conventional means including but not limited to physical constants and spectral data. The reactions are performed in solvents appropriate to the reagents and materials employed and are suitable for transformations being effected. The representative examples include, but are not limited to, tetrahyrdofuran, dimethylforamide, methanol, ethanol, water, dimethylforamide, chloroform, dichloromethane, hexane, toluene, 1,4-dioxane or ethyl acetate.

Unless specified, the reactions described herein were performed at atmospheric pressure over a temperature range from about −78° C. to about 150° C.

For heating, any methods can be used which depends on reagent and target material. The representative examples include, but are not limited to, water bath, oil bath, water bath, or microwave reactor.

The compound of Formula VI in the present invention may be prepared from known compounds by optionally combining the method of the following Preparation methods I to II, similar methods to the following Preparation methods, or synthetic known to a skilled person.

Methods of Preparation

A compound of Formula VI may be synthesized by the following method.

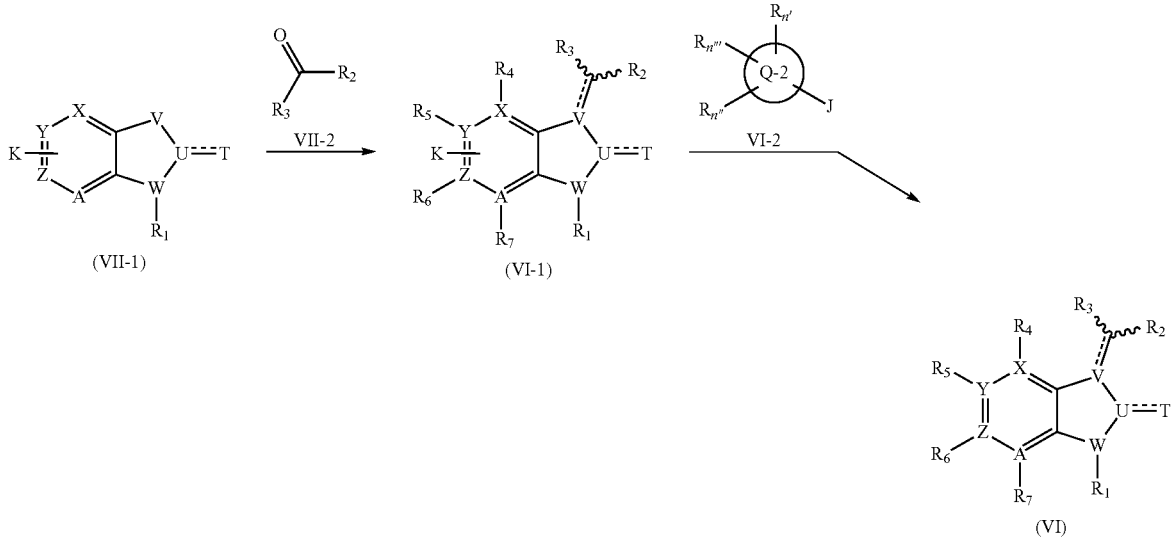

Scheme 1

-continued

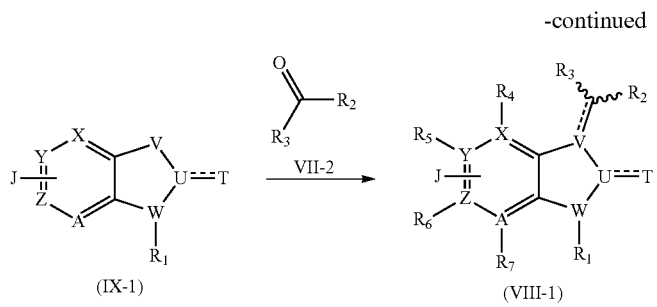

(IX-1)　　　(VIII-1)　　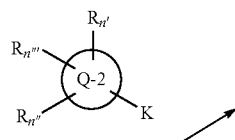

In the scheme, $R_1$, $R_2$, $R_3$, $R_4$, $R_5$, $R_6$, $R_7$, T, U, V, W, X, Y, Z, A, $R_{n'}$, $R_{n''}$, $R_{n'''}$ and Q-2 are as defined in the above Formula V1, except that in VI-1 and VIII-1, $R_4$, $R_5$, $R_6$, and $R_7$ are not

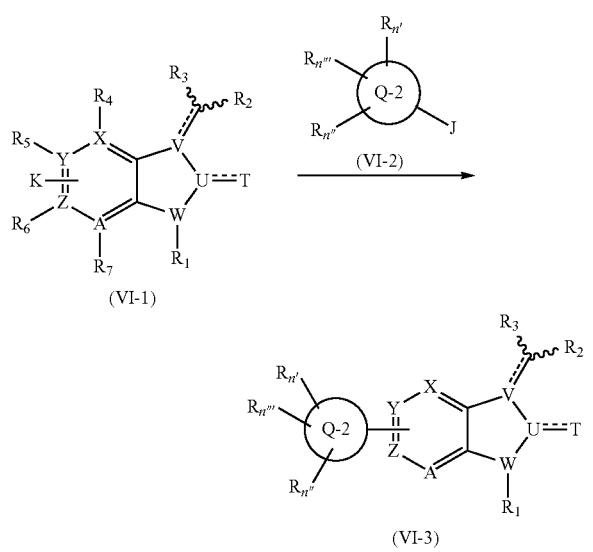

J is metal containing group such as boronic acid, boronic acid pinacol ester, trifluoro boran, organic tin, zinc halide, magnesium halide, organic silicon, and organic lithium. K is leaving group such as Cl, Br, I, and OTf.

Preparation Method I

A compound of the invention may be synthesized by the following method.

Among a compound of Formula VI, Compound VI-3 or a pharmaceutically acceptable salt thereof is prepared by a method as follow:

Scheme 2

(VI-1)

(VI-3)

In the scheme, the symbols have the same meaning as defined above.

A compound of formula VI-1 can react with a compound of formula VI-2 in the presence of transition metal catalyst (representative examples include, but are not limited to tetrakis(triphenylphosphine)palladium(0), [1,1'-bis(diphenylphosphino)ferrocene]palladium(II) dichloride, palladium carbon, dichlorobis(triphenylphosphine)nickel(II), or bis(triphenylphosphine)palladium(II) dichloride.), alkali metal carbonate (representative examples include, but are not limited to potassium carbonate, sodium carbonate, or cesium carbonate.) or other alkali metal salt (sodium hydroxide, potassium hydroxide, sodium ethoxide, sodium methoxide, sodium tert-butoxide, potassium tert-butoxide, sodium hydride, sodium phosphate, potassium phosphate.) and appropriate solvent or without solvent to give a compound of formula VI-3.

Preparation Method II

A compound VI-1 may be prepared from a compound VII-2.

Scheme 3

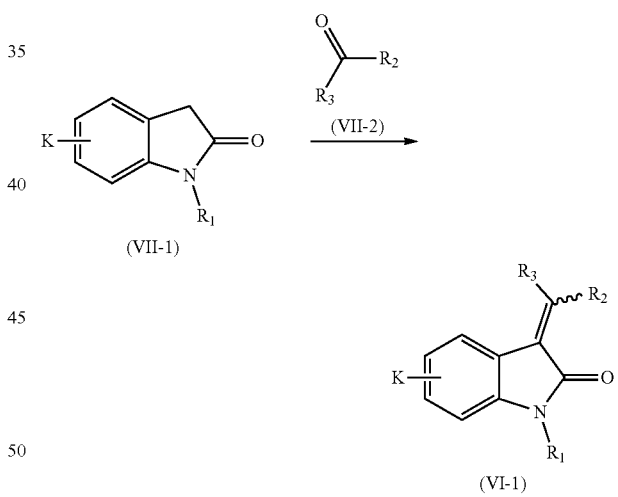

(VII-1)

(VI-1)

In the scheme, the symbols have the same meaning as defined above.

A compound of formula VII-1 can react with a compound of formula VII-2 in the presence of a base (representative examples include, but are not limited to pyrrolidine and piperidine) or an acid (representative examples include, but are not limited to hydrochloric acid, acetic acid, trifluoroacetic acid), and appropriate solvent or without solvent to give a compound of formula VI-1.

Presently disclosed pharmaceutical compositions can be used in an animal or human. A presently disclosed compound can be formulated as a pharmaceutical composition for oral, buccal, parenteral (e.g., intravenous, intramuscular or subcutaneous), topical, rectal or intranasal administration or in a form suitable for administration by inhalation or insufflation. The compounds presently disclosed may also be formulated for sustained delivery according to methods well known to those of ordinary skill in the art. Examples of such formulations can be found in U.S. Pat. Nos. 3,119,742; 3,492,397; 3,538,214; 4,060,598; and 4,173,626.

The formulations may conveniently be presented in unit dosage form and may be prepared by any methods well known in the art of pharmacy. The amount of active ingredient that can be combined with a carrier material to produce a single dosage form will vary depending upon the mammal being treated and the particular mode of administration. The amount of active ingredient, which can be combined with a carrier material to produce a single dosage form, will generally be that amount of the compound that produces a therapeutic effect. Generally, out of 100%, this amount will range, for example, from about 0.1% to about 25% (e.g., 1%, 2%, 5%, 10%, 15%, 20%) of active ingredient.

Therapeutic compositions or formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the alcohol or inhibitor according to the invention is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethyl-cellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents. Suspensions, in addition to the alcohols or inhibitors according to the invention, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more alcohols or inhibitors according to the invention, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention. Formulations of the present invention which are suitable for vaginal administration also include pessaries, tampons, creams, gels, pastes, foams or spray formulations containing such carriers as are known in the art to be appropriate.

Dosage forms for the topical or transdermal administration of an alcohol or other inhibitor according to the invention include powders, sprays, ointments, pastes, creams, lotions, gels, solutions, patches and inhalants. The active compound may be mixed under sterile conditions with a pharmaceutically acceptable excipient, carrier, or diluent, including any preservatives, buffers, or propellants which may be required.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

The ointments, pastes, creams and gels may contain, in addition to an alcohol or other inhibitor according to the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more alcohols or inhibitors according to the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of the alcohol or inhibitor according to the invention, it is desirable to slow the absorption of the alcohol or inhibitor from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered composition is accomplished by dissolving or suspending the alcohol or inhibitor in an oil vehicle. One strategy for depot injections includes the use of polyethylene oxide-polypropylene oxide copolymers wherein the vehicle is fluid at room temperature and solidifies at body temperature.

The pharmaceutical compounds of this invention may be administered alone, or simultaneously, subsequently or sequentially with one or more active agents, other pharmaceutical agents, or with other agents commonly prescribed or used to treat a obesity/overweight symptoms or those of its comorbidities, as well as in combination with a pharmaceutically acceptable excipient, carrier, or diluent as described above.

The amount of pharmacological agent in the oral unit dosage form, with as a single or multiple dosage, is an amount that is effective for treating a neurological disorder. As one of skill in the art will recognize, the precise dose to be employed will depend on a variety of factors, examples of which include the condition itself, the seriousness of the condition being treated, the particular composition used, as well as various physical factors related to the individual being treated. In vitro or in vivo assays can optionally be employed to help identify optimal dosage ranges.

A proposed dose of a presently disclosed compound for oral, parenteral or buccal administration to the average adult human for the treatment or prevention of a disease state herein relevant is about 0.1 mg to about 2000 mg. In certain embodiments, the proposed dose is from about 0.1 mg to about 200 mg (e.g., 1 mg, 5 mg, 10 mg, 20 mg, 50 mg, 75 mg, 100 mg, 150 mg) of the active ingredient per unit dose. Irrespective of the amount of the proposed dose, administration of the compound can occur, for example, 1, 2, 3, or 4 times per day, or 1, 2, 3, 4 or 5 times a week.

Aerosol formulations for the treatment or prevention of the conditions referred to herein the average adult human are preferably arranged so that each metered dose or "puff" of aerosol contains about 20 µg to about 10,000 µg, preferably, about 20 µg to about 1000 µg (e.g., 25 µg, 50 µg, 100 µg, 200 µg, 500 µg, 750 µg) of a presently disclosed compound. The overall daily dose with an aerosol will be within the range from about 100 µg to about 100 mg (e.g., 200 µg, 500 µg, 1 mg, 2 mg, 5 mg, 10 mg, 25 mg, 50 mg, 75 mg). In certain embodiments, the overall daily dose with an aerosol generally will be within the range from about 100 µg to about 10 mg (e.g., 200 µg, 500 µg, 1 mg, 2 mg, 5 mg, 7.5 mg). Administration may be several times daily, for example 1, 2, 3, 4, 5 or 8 times, giving for example, 1, 2 or 3 doses each time.

The compounds of the present invention can be prepared using the methods described below, together with synthetic methods known to one skilled in the art of organic synthesis, medicinal chemistry and related fields, or variations thereon. The reactions are performed in solvents where appropriate to the reagents and materials employed and are suitable for transformations being effected. The starting materials for the examples contained herein are either commercially available or are readily prepared by standard methods from known materials. For example, the following reactions are illustrations but not limitations of the preparation of some of the starting materials and examples used herein.

EXAMPLES

Synthetic Method Examples

Scheme A for making Compound 10-1

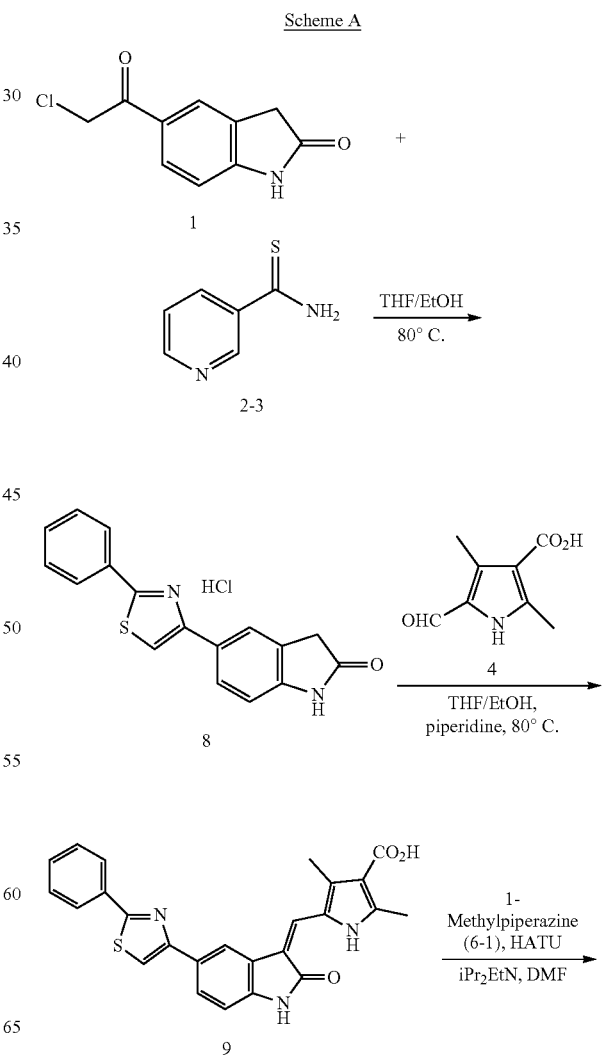

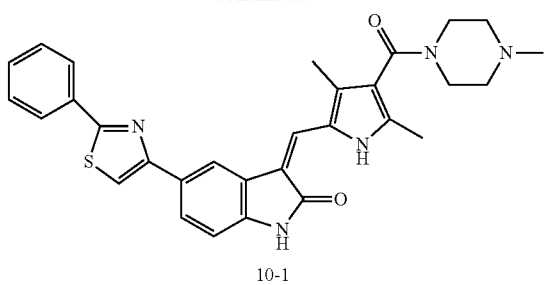

10-1

To a suspension of 5-chloroacetyloxindole 1 (820 mg, 4 mmol) in EtOH/THF (20 mL/20 mL) was added thiobenzamide 2-2 (550 mg, 4 mmol). The mixture was heated at 80° C. for 16 h before cooled down. The solution was concentrated in vacuo to get an orange solid 8. MS m/z 293.20 (M+H).

To this solid 8 was added EtOH/THF (20 mL/20 mL) (or use the above reaction mixture), 5-formyl-2,4-dimethyl-1H-pyrrole-3-carboxylic acid 4 (668 mg, 4 mmol) and piperidine (400 mL). The mixture was heated at 80° C. for 5 hours. After cooled down to room temperature, the reaction mixture was filtrated and washed with EtOH (1 mL) to get the orange solid 9. $^1$H NMR (300 MHz, DMSO-d6) δ 13.80 (s, 1H), 12.40 (s, 1H), 11.10 (s, 1H), 8.47 (s, 1H), 8.07-8.12 (m, 3H), 7.94 (d, 1H, J=8.00 Hz), 7.86 (s, 1H), 7.55-7.6 (m, 3H), 7.01 (d, 1H, J=8.10 Hz), 2.59 (s, 3H), 2.57 (s, 3H); MS m/z 442.20 (M+H).

To a solution of 9 (34 mg, 0.077 mmol) in DMF (1.5 mL) was added HATU (35 mg, 0.092 mmol), diisopropylethylamine (30 mL, 0.168 mmol), and 1-methylpiperazine 6-1 (15 mL, 0.13 mmol). The mixture was stirred at room temperature for 16 hours then concentrated in vacuo. The residue was added CH$_2$Cl$_2$ (2 mL) and extracted with H$_2$O (3×1.5 mL). The organic layer was dried over Na$_2$SO$_4$ and concentrated in vacuo. The residue was purified by column chromatography (CH$_2$Cl$_2$/MeOH/Et$_3$N) to get a yellow solid 10-1. $^1$H NMR (300 MHz, DMSO-d6) d 13.68 (s, 1H), 11.10 (s, 1H), 8.44 (s, 1H), 8.07-8.10 (m, 3H), 7.91 (d, 1H, J=8.00 Hz), 7.80 (s, 1H), 7.68-7.76 (m, 2H), 7.52-7.58 (m, 1H), 7.01 (d, 1H, J=8.10 Hz), 3.02-3.15 (m, 4H), 2.52-2.58 (m, 4H), 2.5 (s, 3H), 2.35 (s, 3H), 2.33 (s, 3H); MS m/z 524.20 (M+H).

Scheme B for Making Compound 7-1

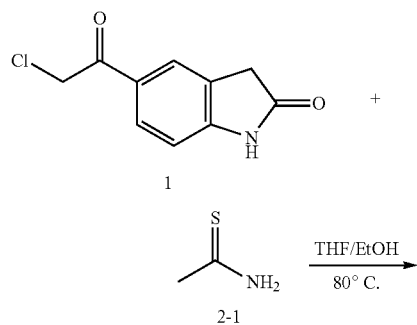

Scheme B

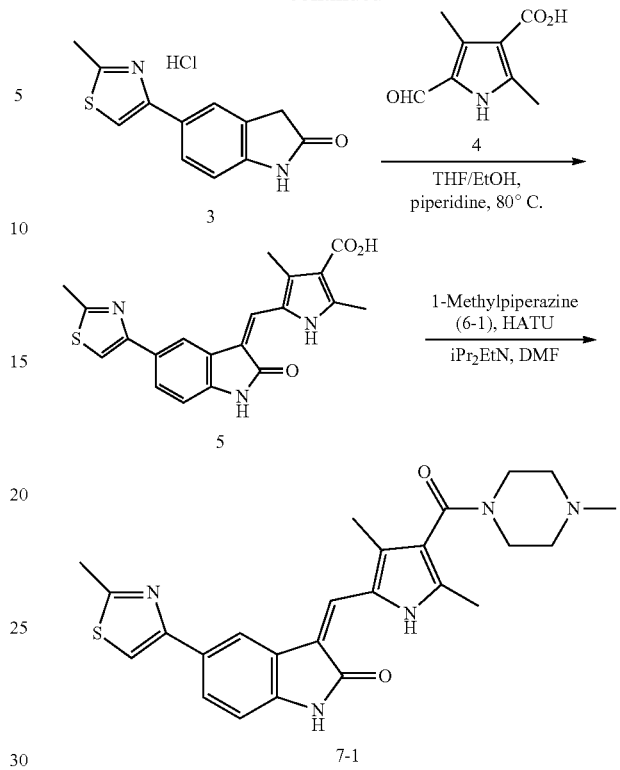

7-1

To a suspension of 5-chloroacetyloxindole 1 (42 mg, 0.2 mmol) in EtOH/THF (2 mL/1 mL) was added thioacetamide 2-1 (15 mg, 0.2 mmol). The mixture was heated at 80° C. for 16 h before cooled down. The solution was concentrated in vacuo to get an orange solid 3. $^1$H NMR (300 MHz, DMSO-d6) δ 10.50 (br. S, 1H), 7.72-7.80 (m, 2H), 7.33 (s, 1H), 7.16 (s, 1H), 6.86 (d, 1H, J=8.63 Hz), 3.42-4.54 (m, 2H); MS m/z 231.10 (M+H).

To a solution of 3 (53 mg, 0.2 mmol) in EtOH/THF (2 mL/1 mL) (or use the above reaction mixture in EtOH/THF (2 mL/1 mL) solution) was added 5-formyl-2,4-dimethyl-1H-pyrrole-3-carboxylic acid 4 (33.4 mg, 0.2 mmol) and piperidine (21.8 mL). The mixture was heated at 80° C. for 2 hours. After cooled down to room temperature, the reaction mixture was filtrated and washed with EtOH (1 mL) to get the reddish solid 5. $^1$H NMR (300 MHz, DMSO-d6) d 13.80 (s, 1H), 12.10 (br.s, 1H), 11.08 (s, 1H), 8.35 (s, 1H), 7.85 (s, 1H), 7.78-7.81 (m, 2H), 6.94 (d, 1H, J=8.11 Hz), 2.74 (s, 3H), 2.56 (s, 3H), 2.52 (s, 3H); MS m/z 380.21 (M+H).

To a solution of 5 (20 mg, 0.052 mmol) in DMF (1.5 mL) was added HATU (24 mg, 0.063 mmol), diisopropylethylamine (30 mL, 0.168 mmol), and 1-methylpiperazine 6-1 (10 mL, 0.090 mmol). The mixture was stirred at room temperature for 16 hours then concentrated in vacuo. The residue was added CH$_2$Cl$_2$ (2 mL) and extracted with H$_2$O (3×1.5 mL). The organic layer was dried over Na$_2$SO$_4$ and concentrated in vacuo. The residue was purified by column chromatography (CH$_2$Cl$_2$/MeOH/Et$_3$N) to get a yellow solid 7-1. $^1$H NMR (300 MHz, DMSO-d6) d 11.00 (s, 1H), 8.30 (s, 1H), 7.83 (s, 1H), 7.65-7.78 (m, 2H), 6.94 (d, 1H, J=8.18 Hz), 3.02-3.20 (m, 4H), 2.74 (s, 3H), 2.5-2.58 (m, 4H), 2.5 (s, 6H), 2.3 (s, 3H); MS m/z 462.20 (M+H).

Scheme C for making Compound 14-3

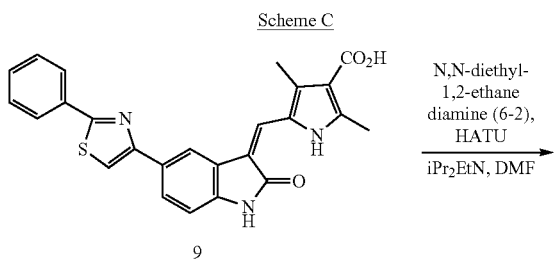

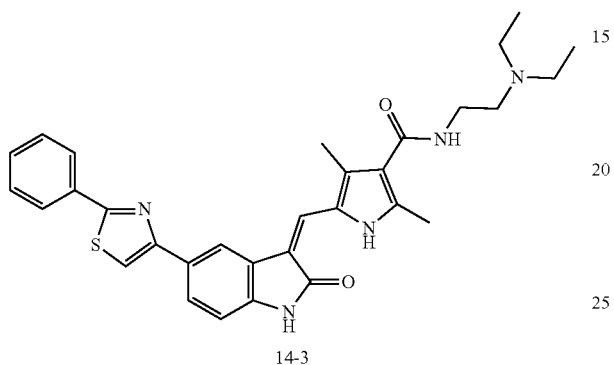

To a solution of 9 (1.55 g, 3.5 mmol) in DMF (130 mL) was added HATU (1.6 g, 4.2 mmol), diisopropylethylamine (1.6 mL, 9.2 mmol), and N,N-diethyl-1,2-ethanediamine 6-2 (0.6 mL, 4.2 mmol). The mixture was stirred at room temperature for 16 hours then concentrated in vacuo. The residue was added $CH_2Cl_2$ (800 mL) and extracted with $H_2O$ (200 mL), saturated $NaHCO_3$ (200 mL), $H_2O$ (2×200 mL), and brine (200 mL). The organic layer was dried over $Na_2SO_4$ and concentrated in vacuo. The residue was added small amount of MeOH and filtration to get a yellow solid 14-3. $^1$H NMR (300 MHz, DMSO-d6) δ 13.70 (s, 1H), 11.10 (s, 1H), 8.44 (s, 1H), 8.07-8.10 (m, 3H), 7.92 (d, 1H, J=8.10 Hz), 7.81 (s, 1H), 7.3-7.6 (m, 3H), 7.00 (d, 1H, J=8.10 Hz), 3.2-3.3 (m, 2H), 2.5-2.6 (m, 6H), 2.51 (s, 3H), 2.48 (s, 3H), 1.00 (t, 6H, J=6.90 Hz); MS m/z 540.20 (M+H).

Scheme D for making Compound 15-1

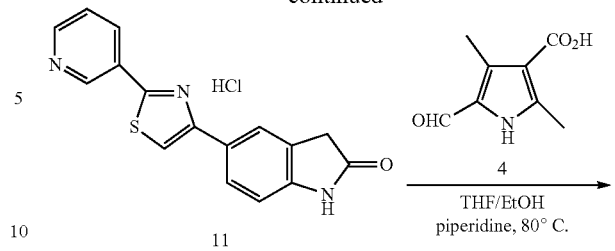

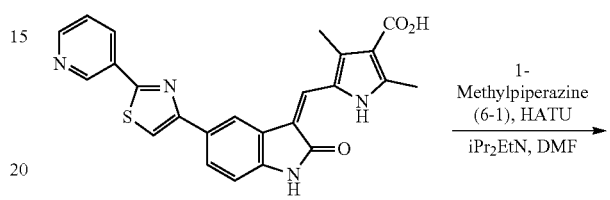

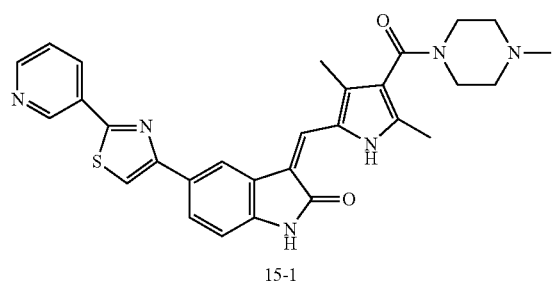

To a suspension of 5-chloroacetyloxindole 1 (42 mg, 0.2 mmol) in EtOH/THF (1 mL/1 mL) was added thionicotinamide 2-3 (27.8 mg, 0.2 mmol). The mixture was heated at 80° C. for 16 h before cooled down. The solution was concentrated in vacuo to get an orange solid 11. MS m/z 294.20 (M+H).

To this solid 11 was added EtOH/THF (1 mL/1 mL), 5-formyl-2,4-dimethyl-1H-pyrrole-3-carboxylic acid (33.4 mg, 0.2 mmol) and piperidine (21.8 mL). The mixture was heated at 80° C. for 2 hours. After cooled down to room temperature, the reaction mixture was concentrated and filtrated to get the orange solid 12. MS m/z 443.20 (M+H).

To a solution of the solid 12 (44 mg, 0.10 mmol) in DMF (1.5 mL) was added HATU (35 mg, 0.12 mmol), diisopropylethylamine (50 mL, 0.33 mmol), and 1-methylpiperazine 6-1 (30 mL, 0.26 mmol). The mixture was stirred at room temperature for 16 hours then concentrated in vacuo. The residue was added $CH_2Cl_2$ (2 mL) and extracted with $H_2O$ (1.5 mL). The organic layer was dried over $Na_2SO_4$ and concentrated in vacuo. The residue was purified by column chromatography ($CH_2Cl_2$/MeOH/$Et_3N$) to get a yellow solid 15-1. $^1$H NMR (400 MHz, DMSO-d6) δ 13.55 (s, 1H), 11.00 (s, 1H), 9.20 (d, 1H, J=1.60 Hz), 8.64 (dd, 1H, J=4.70, 1.60 Hz), 8.35-8.37 (m, 2H), 8.10 (s, 1H), 7.84 (dd, 1H, J=8.00, 1.60 Hz), 7.71 (s, 1H), 7.52 (ddd, J=8.00, 4.70, 0.70 Hz, 1H), 6.92 (d, 1H, J=8.00 Hz), 3.07-3.2 (m, 4H), 2.26 (s, 3H), 2.24 (s, 3H), 2.24-2.3 (m, 4H), 2.13 (s, 3H); MS m/z 525.20 (M+H).

Scheme E for making Compound 15-3

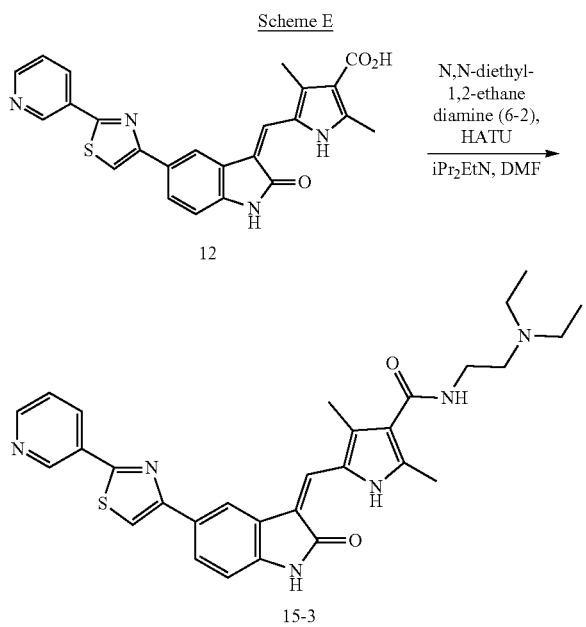

To a solution of the solid 12 (44 mg, 0.10 mmol) in DMF (1.5 mL) was added HATU (35 mg, 0.12 mmol), diisopropylethylamine (50 mL, 0.33 mmol), and N,N-diethyl-1,2-ethanediamine 6-2 (23 mL, 0.2 mmol). The mixture was stirred at room temperature for 16 hours then concentrated in vacuo. The residue was added $CH_2Cl_2$ (2 mL) and extracted with $H_2O$ (1.5 mL). The organic layer was dried over $Na_2SO_4$ and concentrated in vacuo. The residue was purified by column chromatography ($CH_2Cl_2$/MeOH/$Et_3$N) to get a yellow solid 15-3. $^1$H NMR (400 MHz, DMSO-d6) δ 13.60 (s, 1H), 11.00 (s, 1H), 9.18 (d, 1H, J=1.60 Hz), 8.64 (dd, 1H, J=4.80, 1.60 Hz), 8.33-8.37 (m, 2H), 8.09 (s, 1H), 7.83 (dd, 1H, J=8.00, 1.60 Hz), 7.71 (s, 1H), 7.50 (dd, J=8.00, 4.80 Hz, 1H), 7.36-7.39 (m, 1H), 6.91 (d, 1H, J=8.00 Hz), 3.20 (q, J=7.10 Hz, 4H), 2.4-2.6 (m, 4H), 0.90 (t, J=7.10 Hz, 6H); MS m/z 525.20 (M+H). MS m/z 541.20 (M+H).

Compound 15-3 can be prepared from compound 12 and N,N-diethyl-1,2-ethanediamine 6-2 using a method analogous to that used for the preparation of compound 15-1.

Biomedical Assays

Example 1: Compound 14-3 Decreases Body Weight in Obese Mice Without Curbing Daily Caloric or Water Intake In order to assess the in vivo efficacy of Compound 14-3, a preferred embodiment of the compound of the invention, in treating and ameliorating obesity and related diseases like the metabolic syndrome, a previously used modified high-fat diet (HFD) was employed to induce obesity and severe fatty liver disease in mice (Derdak et al. *J of Hepatology* 2013; 58(4):785-91).

Five-week-old male, C57B1/6J mice (12-18 per group, Jackson Laboratory, Bar Harbor, ME) were fed ad libitum with a modified high-fat or control diet (Bioserv, Frenchtown, NJ) for 15 weeks. The calorie profile of the modified HFD (60% of calories from fat) resembled the composition of a previously published diet that effectively induced obesity, steatosis and insulin resistance in this mouse strain (Cong et al. *Life Sci* 2008; 82:983-990). We had verified the efficacy of this diet to induce obesity in various pilot studies. At the end of the 15-week long feeding regimen, this diet caused substantial weight gain in these mice.

After 15 weeks on the modified HFD, the mice were put on a Compound 14-3 (or control vehicle) dosing regimen, in which the introductory 5 mg/kg (p.o., t.i.w. for the first 3 weeks) dose was followed by the administration of 10 mg/kg (p.o., t.i.w. for an additional 5 weeks) therapeutic dose. During the course of the drug treatment, the animals were monitored daily for changes in body weight, food/water intake, and any adverse effects.

As shown in FIG. 1A, the Compound 14-3 treatment not only prevented additional weight gain in the mice on HFD, but also triggered a gradual weight loss. As FIG. 1B demonstrates, there was a marked (~20%) difference in body weight between the Compound 14-3-treated and control-vehicle-treated mice on HFD at the time of euthanasia. Moreover, the Compound 14-3-induced weight loss in HFD-fed mice was not linked to decreased food intake (FIG. 1C) or water intake (FIG. 1D), indicating that a pharmaceutical composition comprising the compound of the invention should be very safe without any detectable side effects other than temporary, self-resolving, mild diarrhea seen in a couple of mice at the initiation of drug treatment. No changes in behaviors or activities were observed in mice.

Example 2: Compound 14-3 Treatment Does Not Affect Intestinal Fat Absorption, Molecular Mediators of Appetite, or Energy Expenditure in Brown Adipose Tissue The markedly lower body weight of the Compound-treated HFD-fed mice in contrast to their vehicle-treated HFD-fed controls promoted further investigations.

Figure 2A:
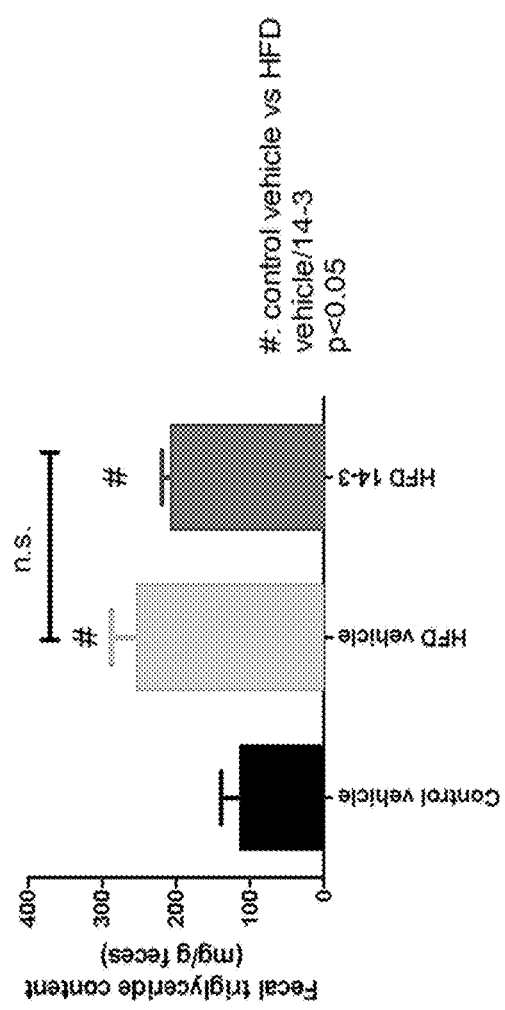

Referring to FIG. 2A, the fecal triglyceride content was assessed using a standard biochemical kit (Biovision, Mountain View, CA). Fecal samples were collected on the 5$^{th}$ week of the treatment over the course of three days. The fecal triglyceride content was normalized to fecal mass. HFD naturally increased the fecal triglyceride abundance, however as shown here, there was little difference between the vehicle- and Compound-14-3-treated mice, indicating that the compound of the invention does not alter intestinal fat absorption. Therefore, this mechanism cannot explain the observed significant weight loss in the drug-treated mice.

Referring now to FIG. 2B, hypothalamic molecular mediators of hunger and satiety signaling in hypothalamus were analyzed using quantitative real-time PCR with commercially available probes (Thermo Fisher Scientific Inc., Waltham, MA). AgRP and NPY are hunger-inducing signals, while POMC is powerful satiety-inducing signal in the hypothalamus. There was no significant difference in the expression of appetite-inducing genes between vehicle- and Compound-14-3-treated animals fed with the HFD. This was in agreement with the food intake information that we collected over the course of the experiment. Additionally, there was a significant decrease in satiety-inducing POMC expression in the HFD-fed, Compound 14-3-treated mice compared to its corresponding control group. Therefore, it was concluded that the expression levels of hypothalamic hunger or satiety genes cannot explain the marked weight loss of the Compound-14-3-treated mice on HFD and that decrease in satiety was secondary to prolonged negative energy balance in the same group.

Finally, the recruitment of brown adipose tissue (BAT) was examined. BAT is a well-know site for dissipating excess energy to prevent weight gain by inducing thermogenesis. Importantly, the expression levels of the two investigated markers of thermogenic BAT activation—UCP1 and DIO2—were not different in the two HFD-fed groups when measured by quantitative real-time PCR (FIG. 2C), indicating similar levels of BAT activation in response to HFD. These findings led us to conclude that for the weigh loss seen in the Compound 14-3-treated HFD-fed mice, other mechanisms are probably responsible.

Example 3: Compound 14-3 Treatment Induces Favorable Changes in Body Composition In agreement with effects of Compound 14-3 seen in the above examples, favorable changes in the body composition of Compound 14-3-treated and HFD-fed mice were also observed at the time of euthanasia through gross examination.

Most importantly, Compound 14-3 markedly decreased the epididymal fat pad weights and fat/body weight ratio (FIGS. 3A and 3B) as well as unilateral fat pad weights and inguinal fat/body weight ratio (FIGS. 3C and 3D). The former anatomical site represents visceral fat depos, while the latter belongs to subcutaneous fat depo from the perspective of human health. Both of these changes were considered very substantial and beneficial in the anti-obesity effect profile of the compound of the invention.

Figure 4A:
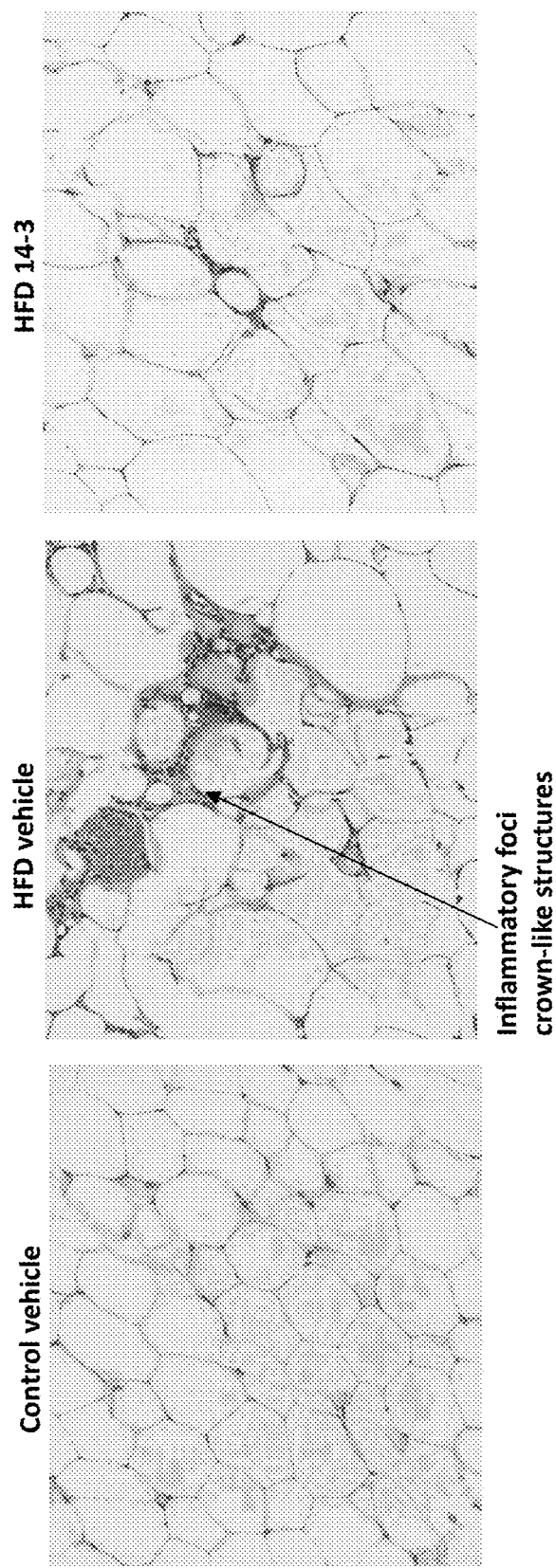
FIGS. 4A-4C present in vivo animal data on: (4A) eWAT visceral tissue; (4B) total number of adipose cells in X200 field; and (4C) TGF$_\beta$ gene expression in eWAT.
Figure 4C:
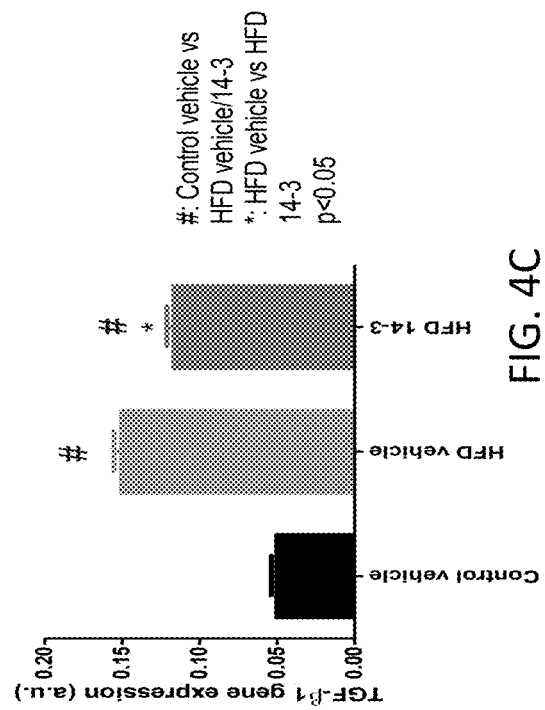
Figure 4B:
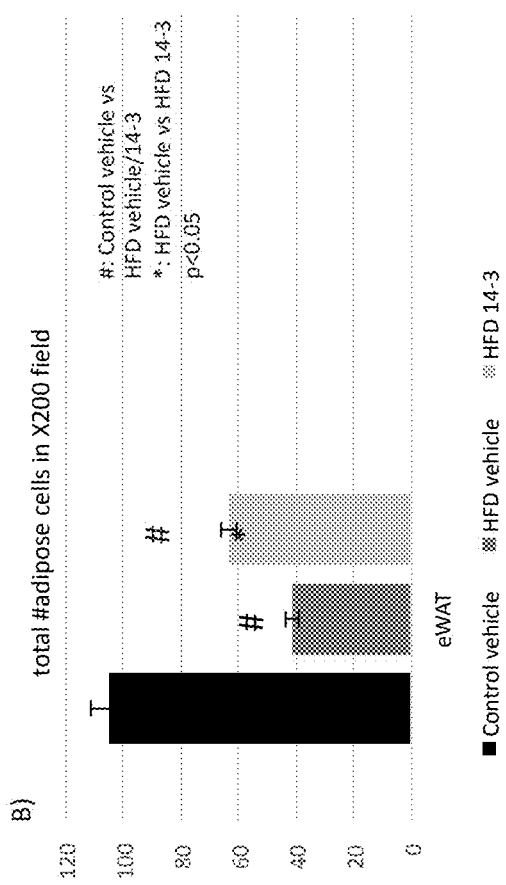

Example 4: Compound 14-3 Treatment Induces Favorable Changes in the Morphology of eWAT Adipocytes and TGF-β Gene Expression Further insights in eWAT morphological changes assessed by H & E staining of eWAT revealed that the decrease in the size of adipocytes in the Compound-14-3-treated, HFD-fed mice (FIG. 4A) was due to overall less fat content in these cells (FIG. 4B).

Since obesity has been linked to low-grade inflammation in the adipose tissue, we consequently observed increased TGF-β expression in the epididymal fat pads of the HFD-fed mice. More importantly, the Compound-14-3-treatment decreased the abundance of TGF-β in eWAT, indicating that Compound 14-3 harbors anti-inflammatory properties (FIG. 4C).

Figure 5A:
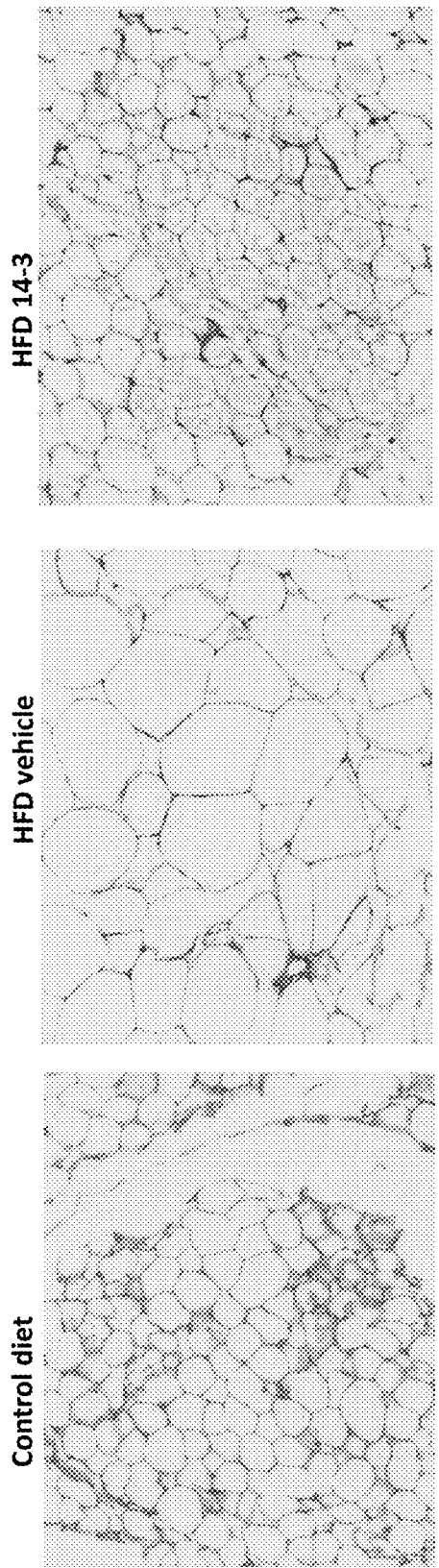
FIGS. 5A-5B present in vivo animal data on: (5A) iWAT visceral tissue; and (5B) total number of adipose cells in X200 field.
Figure 5B:
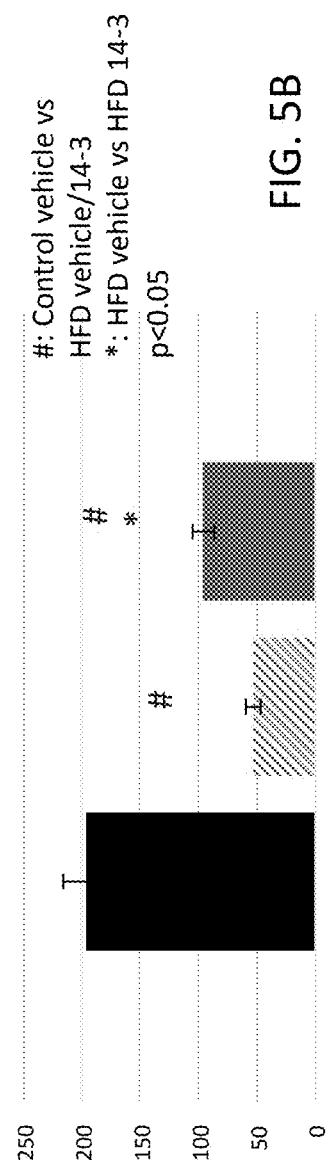

Example 5: Compound 14-3 Treatment Induces Favorable Changes in The Morphology of iWAT Adipocytes Similar pattern of morphological changes was observed by analysis of inguinal (subcutaneous) white adipose tissue (iWAT) assessed by H & E staining followed by morphometry: a decrease in size of adipocytes in the Compound 14-3-treated HFD-fed group (FIG. 5A) was due to overall less fat content in the iWAT adipocytes (FIG. 5B).

Example 6: Compound 14-3 Treatment Induces Favorable Changes in Gene Expressions in eWAT To get a more detailed insight into the metabolic changes caused by the Compound 14-3 treatment in the visceral fat (eWAT), the expression of genes involved in lipid transport and degradation, beta-oxidation, de novo lipogenesis, and insulin sensitivity were examined.

As FIG. 6 demonstrates, the Compound 14-3 treatment induced catabolic events in visceral white adipocytes. For example, the expression of RAR-related orphan receptor alpha (RORA, FIG. 6A), a nuclear receptor with anti-fat and anti-inflammatory properties has been significantly increased in the eWAT of HFD-fed Compound-14-3-treated mice. Acyl-Coenzyme A dehydrogenase, C-4 to C-12 straight chain (ACADM, FIG. 6B) is known to be important for the degradation of medium chain fatty acids. Increased gene expression of ACADM has found in the Compound 14-3-treated group, suggesting that Compound 14-3 has catabolic properties.

Furthermore, we have found that the expression of peroxisomal acyl-coenzyme A oxidase 1 (ACOX1, FIG. 6C) has been increased by the Compound 14-3-treatment, highlighting the "fat burning" properties of compounds of the invention. Similarly, malonyl CoA decarboxylase (MLYCD, FIG. 6D) has been induced by the Compound 14-3 treatment. This event is linked to decreased malonyl CoA synthesis and the suppression of de novo lipogenesis by Compound 14-3. Finally, the gene expression of phosphoenolpyruvate carboxykinase (PEPCK, FIG. 6E) in the eWAT of HFD-fed Compound 14-3-treated mice was comparable to that of the control-fed mice, suggesting that Compound 14-3 may have a role in prevention of insulin resistance.

Example 7: Compound 14-3 Treatment Increases the Expression of Mediators of Fatty Acid Oxidation, and Improves Leptin Resistance in HFD-fed Mice Many of the beneficial metabolic effect are linked to FGF21, and FGF21 itself may further enhance fatty acid oxidation (Xu J, et al. *Diabetes* (2009) 58(1):250-259; Li H, et al. *Diabetes* (2012) 61(4):797-806). We, therefore, also measured serum levels of FGF21 using a commercially available ELISA kit. As shown in FIG. 7A, treatment of HFD-fed mice with Compound-14-3 increased serum FGF21 levels and gene expression (FIG. 7B). These data suggest that FGF21 activity seemed to be specifically induced by Compound-14-3 treatment. Accordingly, in an aspect of the invention, Compound 14-3 treatment is utilized to increase fatty acid oxidation, resulting in decreased fat content in iWAT and eWAT, and decreased body weight in a subject.

Since crosstalk between leptin and FGF21 has been proposed in connection with the anti-obesity effects of FGF21 and a suppressive effect of exogenous FGF21 on circulating leptin levels has been previously observed in non-human primates, we also measured serum leptin levels using a commercially available ELISA kit. As expected, changes in fat content in the Compound 14-3-treated HFD group were followed by decrease in serum levels of fat-derived 'satiety' hormone leptin, indicating improved leptin resistance resulting from treatment using a compound of the invention (FIG. 7C). Thus, lower circulation levels of leptin were most likely due to drug-induced reductions in the masses of fat depos. This finding can explain decrease in POMC gene expression in the hypothalamus, as leptin is capable to directly modulate hypothalamic melanocortin system by changing the activity of POMC neurons.

Figures 8A, 8B:
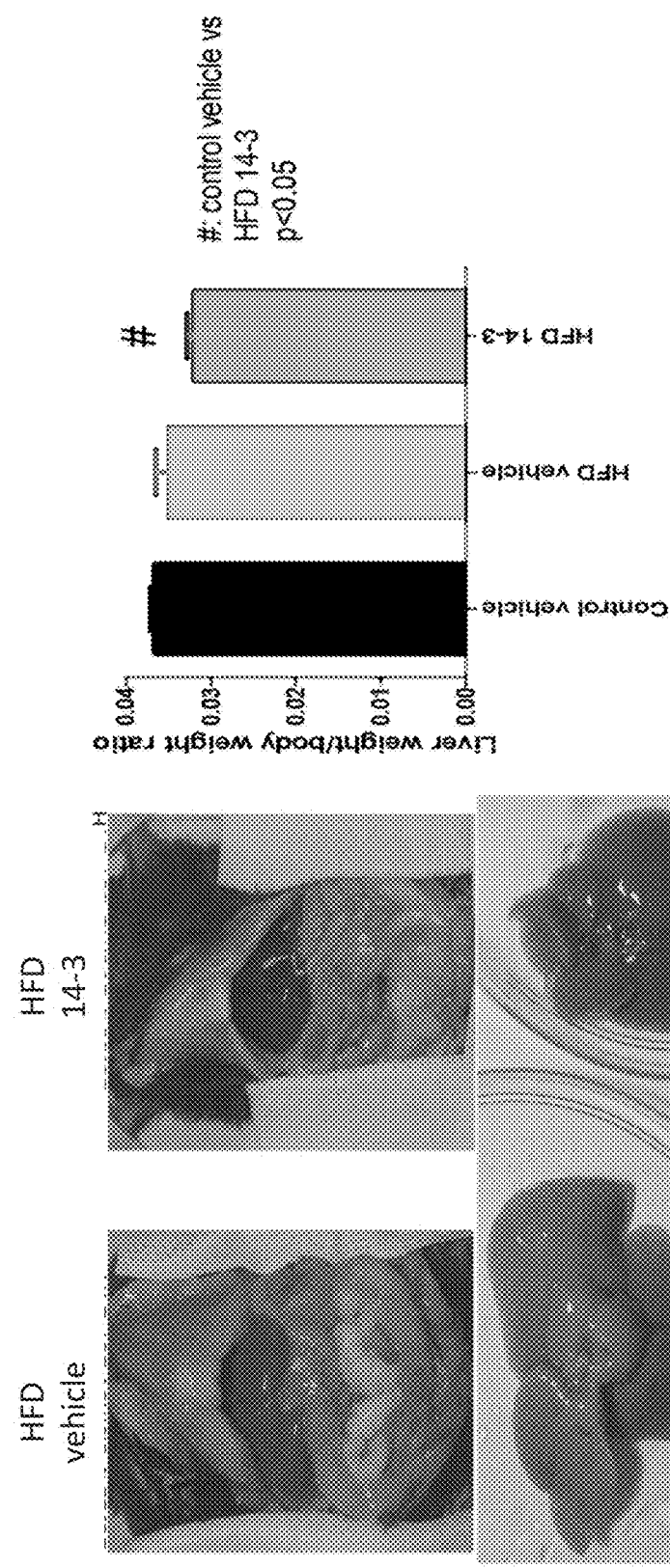
FIGS. 8A-8B present in vivo animal data on: (8A) marked improvement of NAFLD after treatment with compound of the invention (Compound 14-3); and (8B) lower liver/body weight ratio after treatment with Compound 14-3.

Example 8: Compound 14-3 Treatment Induces Favorable Changes in Body Composition With Respect To Liver Too Favorable changes in body composition were observed in liver as well (FIGS. 8A and 8B): HFD feeding in the vehicle-treated mice promoted liver enlargement due to ectopic fat accumulation in this organ. The enlarged liver appeared pale yellow consistent with fatty metamorphosis. On the other hand, Compound 14-3 markedly decreased the size of the liver in the HFD-fed mice and helped to maintain a healthier, darker brown appearance (right side in FIG. 8A). The beneficial effect on liver size and appearance was consistent as a part of overall improvement in metabolic properties after Compound 14-3 treatment.

Example 9: Compound 14-3-Induced Changes in Body Composition Were Linked To Better Glucose Tolerance And Whole Body Insulin Sensitivity Having in mind that successful anti-obesity drug needs to have not only clinically significant weight loss results (>5%) but also needs to delay or prevent the development of type II diabetes, we assessed the anti-diabetic properties of Compound 14-3.

The described beneficial changes in body composition improved all aspects of the metabolic syndrome, including the underlying insulin resistance. Therefore, to fully characterize this animal model, we also assessed insulin signaling on live animals on the $5^{th}$ week of Compound 14-3-treatment by conducting oral glucose tolerance test (OGTT, FIGS. 9A-C) and intraperitoneal insulin tolerance test (ITT, FIGS. 9D-E).

Both the OGTT and ITT tests were carried out on mice that have been starved for 6 hours before the procedure to eliminate the effect of the last meal on the blood glucose level. In both tests, we measured fasting glucose levels 30 min before the start of the assay to define baseline conditions. In the OGTT assay, the mice had been gavaged with 2 g/kg glucose, dissolved in water. After administration of the glucose, blood glucose level was measured via tail vein nicking using a commercially available glucometer. The obtained data was plotted against time (FIG. 9A) and the area under curve (AUC) calculations were carried out (FIG. 9B). Additionally, the blood glucose level measured at 120 min after gavage was used to describe the overall glucose tolerance of the mice (FIG. 9C). As the data suggest, Compound 14-3 treatment markedly improved glucose tolerance in the HFD-fed mice, as evidenced by the smaller AUC and decreased 120-min glucose levels when compared to their vehicle-treated littermates.

In the ITT test, we have intraperitoneally administered 0.75 g/kg human recombinant insulin (Humulin N, Eli Lilly, Cambridge, MA) at the start of the assay and blood glucose was similarly measured for 120 min. The steeper drop in blood glucose levels in response to insulin and the smaller AUC in the ITT test indicated that the Compound 14-3-treated mice were more sensitive to the effects of insulin than their HFD-fed and vehicle-treated littermates. These data collectively indicate that Compound 14-3 may not only promote weight loss but also improve overall glucose homeostasis and insulin sensitivity in HFD-fed mice. Improved insulin resistance and better glucose tolerance are very desirable clinical effects in the treatment of obesity, type II diabetes, the metabolic syndrome, and NAFLD.

Example 10: Compounds of the Invention Prevent Excess Triglyceride Accumulation in Human Liver Cells The preferred embodiments of the compounds of the invention were evaluated for their ability to inhibit fat buildup, here in cell culture, in order to see if they can be used in treating and ameliorating obesity and related diseases like non-alcoholic fatty liver disease (NAFLD).

Figures 10A, 10B:
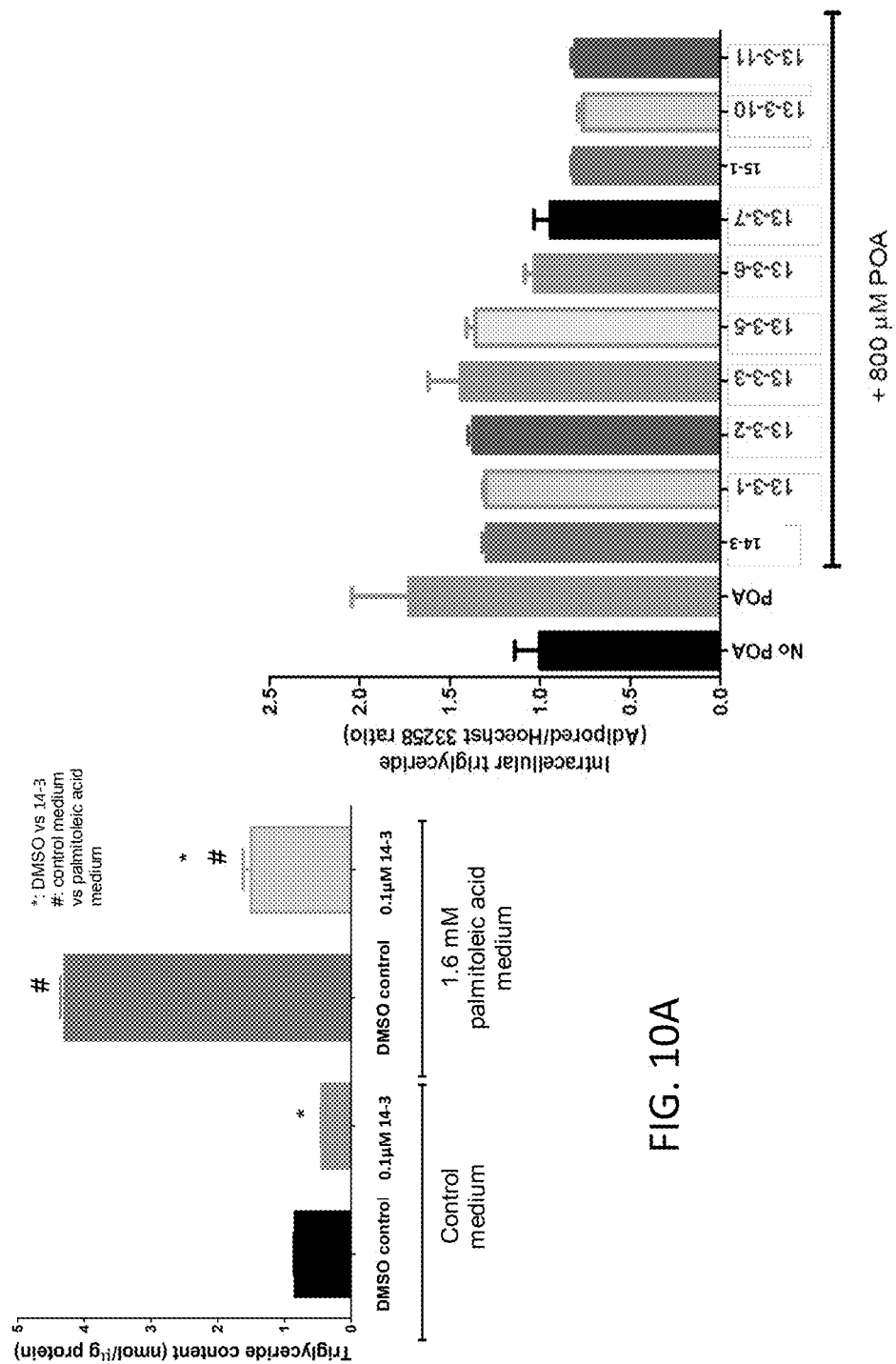
FIGS. 10A-10C present data on tests designed to see if compounds of the invention had any effect on triglyceride accumulation in human liver cell culture.

A series of in vitro experiments were first carried out with various human hepatocyte cultures. For example, human HepG2 liver cells were incubated with 1.6 mM palmitoleic acid in EMEM medium for 48 hours in the presence of 0.1 µM Compound 14-3 or control vehicle, DMSO. After 48 hours, cells were collected and the intracellular triglyceride content was measured by a biochemical kit (Biovision, Mountain View, CA) as described in Derdak et al. *J Hepatol.* 2013; 58(4):785-91. As shown in the figure (FIG. 10A), the palmitoleic acid treatment substantially increased the intracellular triglyceride content in the HepG2 cells, yet this event was markedly suppressed by Compound 14-3, showing a strong inhibitory effect on fat accumulation in human liver cells.

The effects of Compound 13-3-1, Compound 13-3-2, Compound 13-3-3, Compound 13-3-5, Compound 13-3-6, Compound 13-3-7, Compound 15-1, Compound 13-3-10 and Compound 13-3-11, as exemplary compounds of the invention, were tested. Human HepG2 liver cells were incubated with 0.8 mM palmitoleic acid in EMEM medium for 24 hours in the presence of 0.1 µM compounds or control vehicle, DMSO. Subsequently, the cells were washed with PBS and the intracellular fat content was measured by AdipoRed/Hoechst 33258 double staining, which was assessed by flourometry. As shown in the figure (FIG. 10B), the palmitoleic acid treatment substantially increased the intracellular triglyceride content in the HepG2 cells, yet this event was markedly suppressed by each of these nine compounds respectively, showing a comparable or greater inhibitory effect on fat accumulation in human liver cells as compared to Compound 14-3.

Figure 10C:
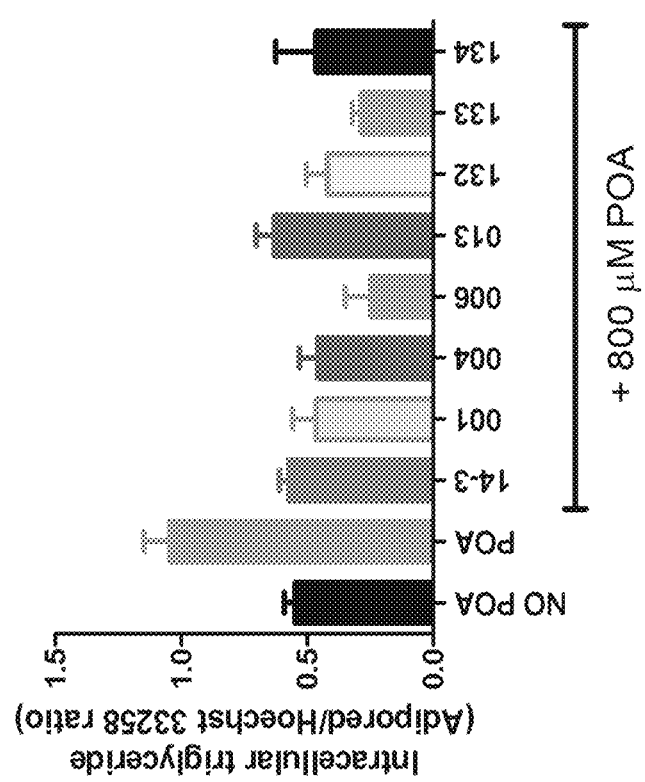

And the effects of Compound 001, Compound 004, Compound 006, Compound 013, Compound 132, Compound 133 and Compound 134, as further exemplary compounds of the invention, were also tested. Human HepG2 liver cells were incubated with 0.8 mM palmitoleic acid in EMEM medium for 48 hours in the presence of 0.1 µM compounds of the invention or control vehicle, DMSO. Subsequently, the cells were washed with PBS and the intracellular fat content was measured by AdipoRed/Hoechst 33258 double staining, which was assessed by flourometry. As shown in the figure (FIG. 10C), the palmitoleic acid treatment substantially increased the intracellular triglyceride content in the HepG2 cells, yet this event was markedly suppressed by these seven deuterides respectively, showing a comparable or greater inhibitory effect on fat accumulation in human liver cells as compared to Compound 14-3.

This observation led to a hypothesis that compounds of the invention may have an intrinsic hepatotropic effect; by directly affecting hepatic fatty acid metabolism, it may alleviate hepatic steatosis and subsequent liver injury in a murine model of NAFLD.

In conclusion, the compound of the invention, in a representative embodiment as Compound 14-3, is an attractive, novel agent in the treatment and prevention of obesity or overweight, as well as closely associated type II diabetes and the metabolic syndrome. The compound of the invention exhibits a well tolerated yet highly effective weight-reduction profile. Specifically, the compound of the invention showed the capacity for promoting fatty acid oxidation and inhibiting de novo fatty acid synthesis in a mouse model in vivo. The data indicated improved insulin sensitivity, reduction in inflammation, as well as less fatty acid deposit after treatment in a mouse model of diet-induced obesity. With regard to liver, the compound of the invention improved many aspects of NAFLD both in a mouse model in vivo and in human liver cell culture, suppressed liver injury and decreased hepatic triglyceride content. Furthermore, treatment by the compound of the invention does not appear to affect caloric intake or water intake, nor does it appear to induce satiety or suppress hunger—attractive to patients who would not want to make some or any of the lifestyle restrictions often associated with diet regimen or weight loss medications. The compound of the invention acts mostly on white adipose tissue (WAT) and liver, and ultimately decreases body weight. Therefore, it may be an ideal candidate in the treatment of obesity and associated co-morbidities.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes, to the full extent allowed by the law. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

The invention claimed is:

1. A method for treating a condition selected from the group consisting of obesity, overweight, type II diabetes and the metabolic syndrome in a mammal, comprising administering to a mammalian subject in need thereof:

(a) a therapeutically effective amount of a pharmaceutical composition comprising a compound of Formula I:

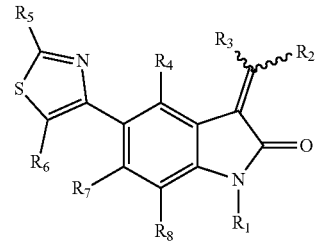

or an enantiomer, diastereomer, tautomer, or pharmaceutically acceptable salt, solvate thereof that is effective in the treatment or prevention of a condition selected from the group consisting of obesity, overweight, type II diabetes and the metabolic syndrome in a mammal, and wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_2$ is heterocycle or substituted heterocycle, aryl or substituted aryl;

$R_3$ is hydrogen, alkyl or substituted alkyl;

$R_4$, $R_7$, and $R_8$ are each independently hydrogen;

$R_5$ is alkyl or substituted alkyl, heterocycle or substituted heterocycle, aryl or substituted aryl, amino or substituted amino;

$R_6$ is hydrogen, halogen, cyano, nitro, $CF_3$, $OCF_3$, alkyl or substituted alkyl, or $OR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;

$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and (b) a pharmaceutically acceptable excipient, carrier, or diluent.

2. The method of claim 1, wherein the compound of Formula I is further a compound of Formula II:

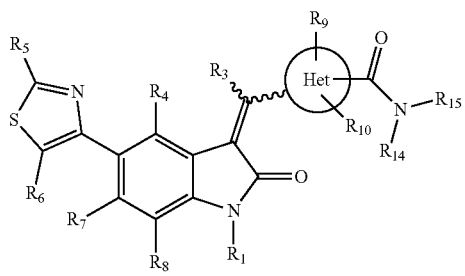

(II)

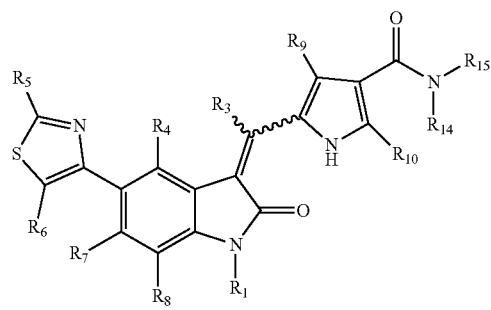

(IV)

or an enantiomer, diastereomer, tautomer, or pharmaceutically acceptable salt, solvate thereof that is effective in the treatment or prevention of a condition selected from the group consisting of obesity, overweight, type II diabetes and the metabolic syndrome in a mammal, and wherein the symbols have the following meanings and are, for each occurrence, independently selected:

Het is a 5- or 6-membered aromatic ring containing at least one heteroatom selected from N, O and S;

$R_9$ and $R_{10}$ are each independently hydrogen, alkyl or substituted alkyl, heterocycle or substituted heterocycle, aryl or substituted aryl;

$R_{14}$ and $R_{15}$ are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle.

3. The method of claim 2, wherein the compound of Formula II is further a compound of Formula III:

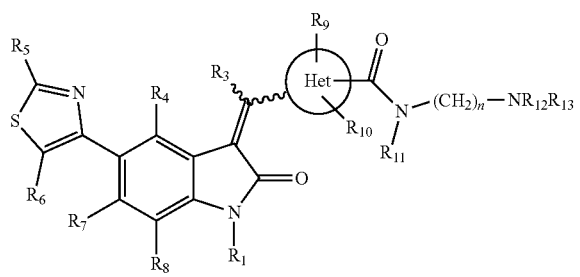

(III)

or an enantiomer, diastereomer, tautomer, or pharmaceutically acceptable salt, solvate thereof that is effective in the treatment or prevention of a condition selected from the group consisting of obesity, overweight, type II diabetes and the metabolic syndrome in a mammal, and wherein the symbols have the following meanings and are, for each occurrence, independently selected:

$R_{11}$ is hydrogen or $C_{1-4}$alkyl;

$R_{12}$ and $R_{13}$ are independently hydrogen, alkyl or substituted alkyl, cycloalkyl or substituted cycloalkyl, heterocycle or substituted heterocycle, or aryl or substituted aryl, or said $R_{12}$ and $R_{13}$ together with the N to which they are bonded optionally form a heterocycle or substituted heterocycle; and n is an integer selected from 2, 3, 4, 5 and 6.

4. The method of claim 2, wherein the compound of Formula II is further a compound of Formula IV:

or an enantiomer, diastereomer, tautomer, or pharmaceutically acceptable salt, solvate thereof that is effective in the treatment or prevention of a condition selected from the group consisting of obesity, overweight, type II diabetes and the metabolic syndrome in a mammal.

5. The method of claim 3, wherein the compound of Formula III is further a compound of Formula V:

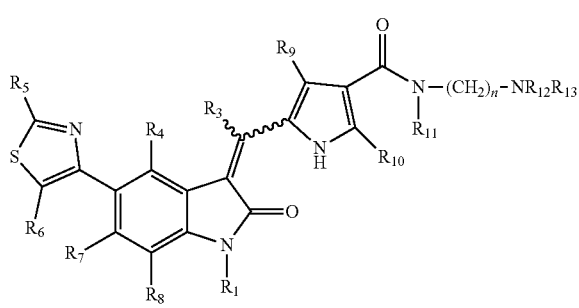

(V)

or an enantiomer, diastereomer, tautomer, or pharmaceutically acceptable salt, solvate thereof that is effective in the treatment or prevention of a condition selected from the group consisting of obesity, overweight, type II diabetes and the metabolic syndrome in a mammal.

6. The method of claim 1, further comprising administering an additional agent selected from the group consisting of: an insulin sensitizing medication, a diabetes medication, a therapeutic for the metabolic syndromes, and a weight-loss medication.

7. The method of claim 1, wherein the mammal is a human.

8. The method of claim 1, wherein the compound of Formula I is selected from the group consisting of:

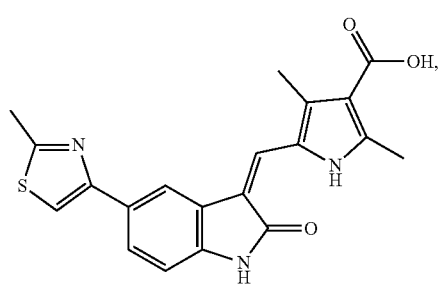

(1)

(2)
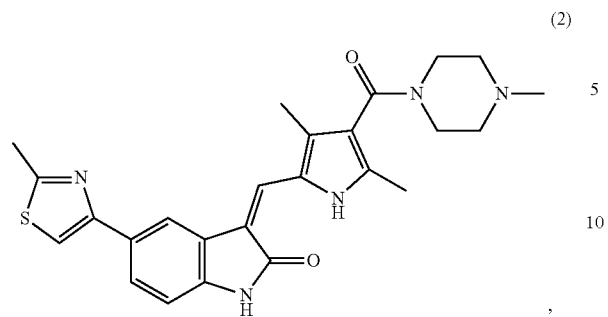
,
(3)
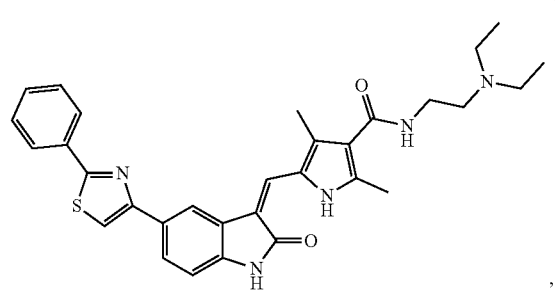
,
(4)
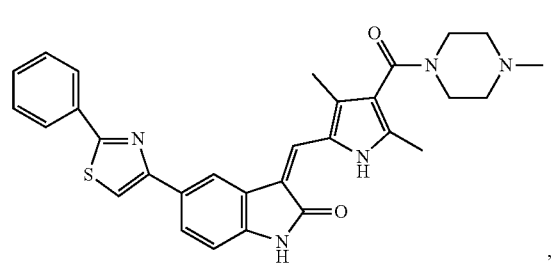
,
(5)
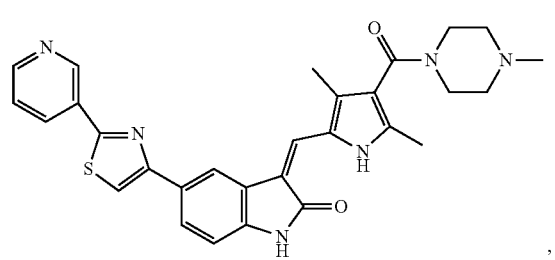
,
(6)
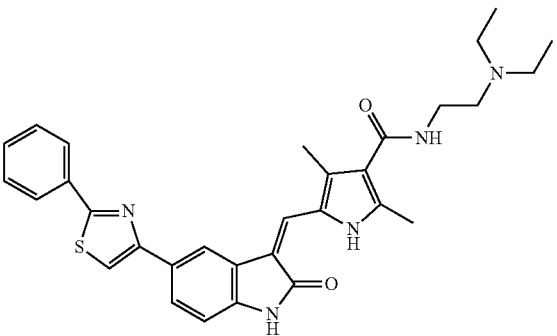
,
(7)
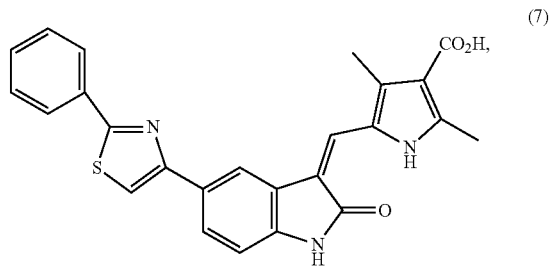
(8)
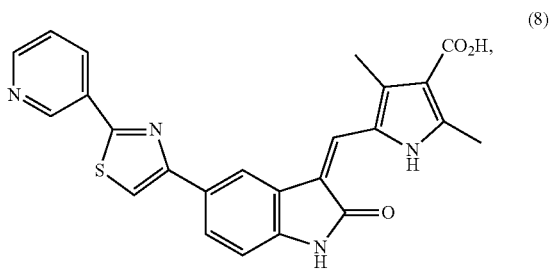
(9)
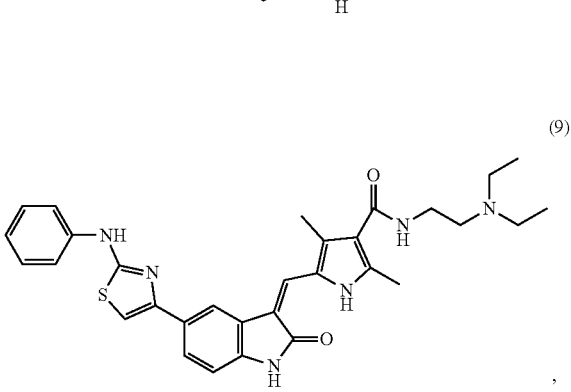
,
(10)
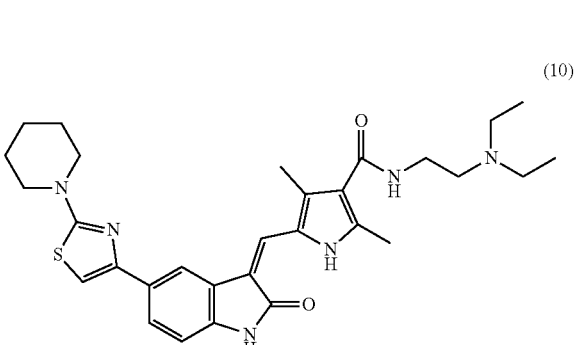
,
(11)
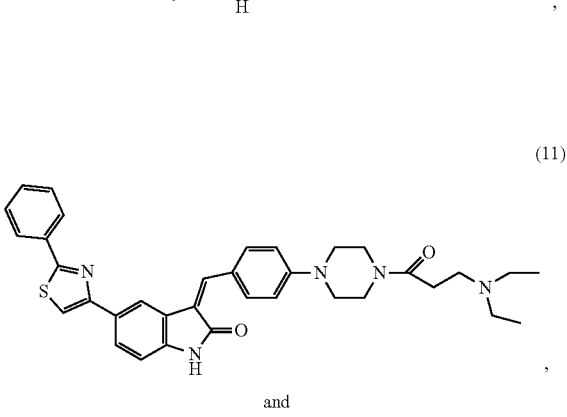
and (12)

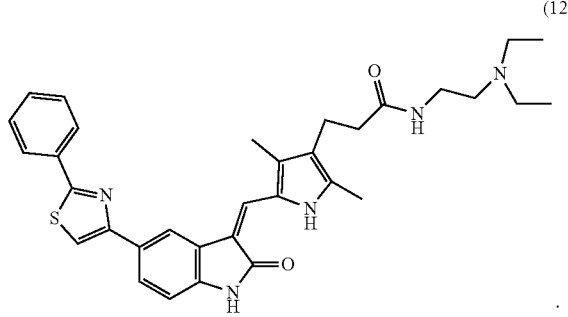

9. The method of claim 1, wherein the compound of Formula I comprises at least one deuterium, and is selected from the group consisting of:

(13)

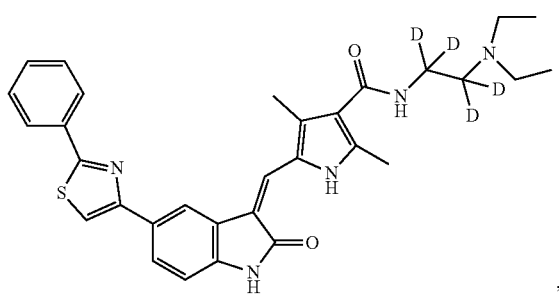

, (14)

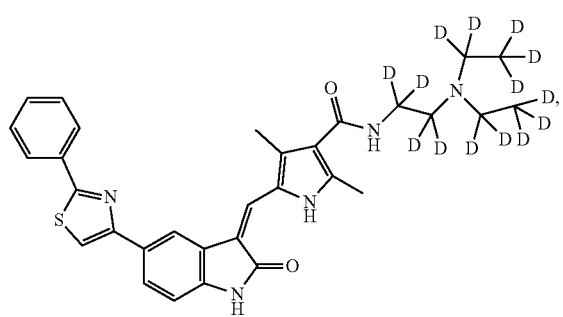

, (15)

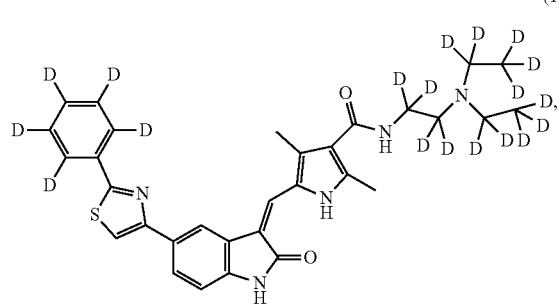

(16)

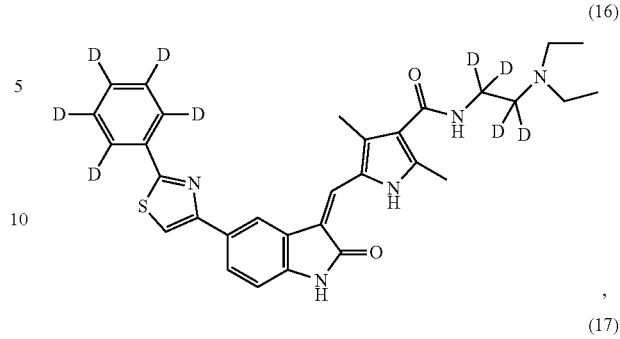

, (17)

(18)

(19)

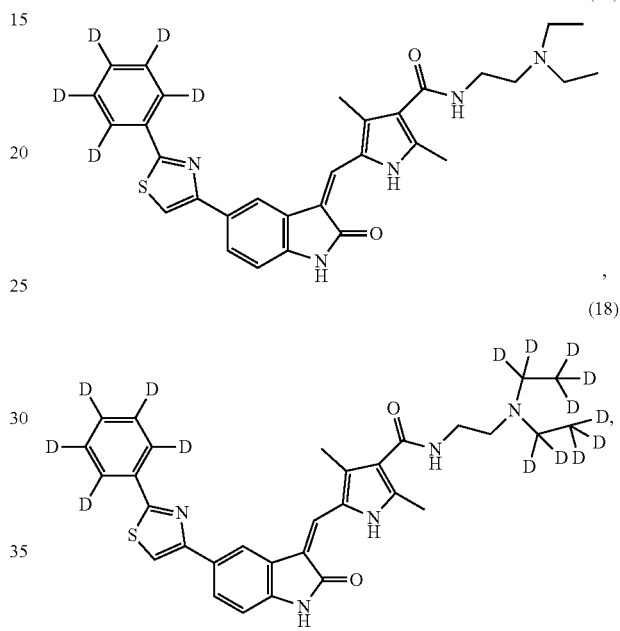

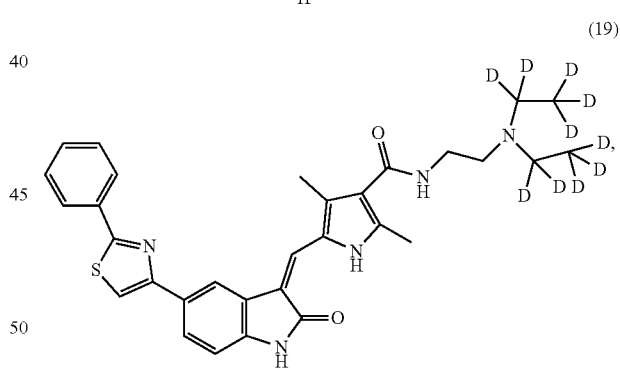

and an enantiomer, diastereomer, tautomer, or pharmaceutically acceptable salt, solvate.

10. The method of claim 1, whereby the method reduces or ameliorates at least one symptom or indication morbidity or mortality known to be associated with obesity, overweight, type II diabetes or the metabolic syndrome, wherein the at least one symptom or indication is selected from the group consisting of: excessive weight, excessive fat, a BMI>25 kg/m$^2$, insulin resistance, frequent urination, increased thirst, increased hunger, elevated blood pressure, elevated fasting plasma glucose, high serum triglycerides, low high-density lipoprotein (HDL) levels, and elevated waist circumference.

11. The method of claim 10, wherein the symptom or indication is a BMI≥30 kg/m².

\* \* \* \* \*